US007125988B2

(12) United States Patent
Takeuchi et al.

(10) Patent No.: US 7,125,988 B2
(45) Date of Patent: Oct. 24, 2006

(54) DYE-FORMING COUPLER AND SILVER HALIDE COLOR PHOTOGRAPHIC LIGHT-SENSITIVE MATERIAL

(75) Inventors: Kiyoshi Takeuchi, Minami-ashigara (JP); Nobuo Seto, Minami-ashigara (JP); Hiroyuki Yoneyama, Minami-ashigara (JP); Shigeki Uehira, Minami-ashigara (JP); Satoshi Sano, Minami-ashigara (JP); Yasuhiro Shimada, Minami-ashigara (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 89 days.

(21) Appl. No.: 10/669,414

(22) Filed: Sep. 25, 2003

(65) Prior Publication Data

US 2005/0079456 A1    Apr. 14, 2005

(30) Foreign Application Priority Data

Sep. 27, 2002 (JP) ............................. 2002-283780
Sep. 27, 2002 (JP) ............................. 2002-284156

(51) Int. Cl.
  *C07D 285/34* (2006.01)
  *G03C 1/06* (2006.01)
  *G03C 7/26* (2006.01)
  *G03C 7/32* (2006.01)

(52) U.S. Cl. ........................................ 544/12; 430/558
(58) Field of Classification Search .................. 544/12; 430/558
  See application file for complete search history.

(56) References Cited

U.S. PATENT DOCUMENTS

| 3,841,880 A | 10/1974 | Kertel |
| 5,021,330 A | 6/1991 | Bergthaller et al. |
| 5,024,930 A | 6/1991 | Kita et al. |
| 5,213,958 A | 5/1993 | Motoki et al. |
| 5,427,902 A | 6/1995 | Shimura et al. |
| 5,455,149 A | 10/1995 | Bergthaller |
| 6,043,017 A | 3/2000 | Bergthaller |
| 6,727,053 B1 | 4/2004 | Takeuchi et al. |
| 2004/0091825 A1* | 5/2004 | Yoneyama et al. ......... 430/557 |
| 2004/0234908 A1* | 11/2004 | Seto et al. ................. 430/570 |

FOREIGN PATENT DOCUMENTS

| DE | 196 01 142 A1 | 1/1997 |
| EP | 0 336 411 A2 | 11/1989 |
| EP | 0 953 870 A1 | 11/1999 |
| EP | 1 246 006 A2 | 10/2002 |
| JP | 52-82423 A | 7/1977 |
| JP | 58-111943 A | 7/1983 |
| JP | 4-78582 A | 3/1992 |

* cited by examiner

*Primary Examiner*—Fiona T. Powers
(74) *Attorney, Agent, or Firm*—Birch, Stewart, Kolasch and Birch, LLP

(57) ABSTRACT

A yellow dye-forming coupler represented by formula (I):

formula (I)

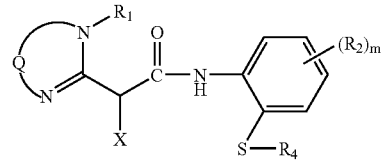

wherein Q represents a group of nonmetallic atoms that form a 5- to 7-membered ring in combination with the $-N=C-N(R_1)-$; $R_1$ and $R_2$ each represent a substituent; $R_4$ represents an alkyl group; m represents an integer of 0 to 4; and X represents a hydrogen atom, or a group capable of being split-off upon a coupling reaction with an oxidized product of a developing agent; and when $R_4$ represents a primary alkyl group, $R_1$ represents $-(CH_2)_3O-R_{101}$ in which $R_{101}$ is an alkyl group having 4 to 8 carbon atoms. A silver halide color photographic light-sensitive material having at least one yellow dye-forming coupler represented by formula (I) in at least one layer provided on a support.

15 Claims, No Drawings

DYE-FORMING COUPLER AND SILVER HALIDE COLOR PHOTOGRAPHIC LIGHT-SENSITIVE MATERIAL

This nonprovisional application claims priority under 35 U.S.C. § 119(a) on Patent Application No(s). 2002-283780 and 2002-284156 filed in JAPAN on Sep. 27, 2002, which is(are) herein incorporated by reference.

FIELD OF THE INVENTION

The present invention relates to a silver halide photographic light-sensitive material. Particularly, the present invention relates to a silver halide color photographic light-sensitive material that is excellent in color reproducibility and image storability (preservability).

BACKGROUND OF THE INVENTION

In a silver halide photographic light-sensitive material (hereinafter, also referred to simply as "a light-sensitive material") for subtractive color photography, a color image is formed by dyes of three primary colors of yellow, magenta, and cyan. In the color photography that uses current p-phenylenediamine-series color-developing agents, acylacetoanilide-series compounds are used as yellow couplers. However, the hue of the yellow dyes obtained from these yellow couplers is reddish, due to an inferior sharpness of a peak of the absorption curve at the longer wavelength side (that is, on the absorption curve, the peak in interest has subsidiary absorption at its foot portion at the longer wavelength side), which renders it difficult to obtain a yellow hue with high purity. Further, because the molecular extinction coefficient of the yellow dyes is low, it is necessary, to attain a desired color density, to use larger amounts of both the coupler and the silver halide. The use of such larger amounts of these components has a problem that the resulting increase in thickness of a light-sensitive material sometimes lowers the sharpness of the obtained color image. Further, the above-mentioned dyes are apt to decompose under conditions of high temperature and high humidity, or of irradiation by radiation, and have a weakness of image storability after development processing. Accordingly, it has been desired to improve these weak points.

In order to solve these problems, improvement of acyl groups and anilido groups were proposed on the couplers. Recently, as improved couplers of the conventional acylacetoanilide-series couplers, there were proposed, for example, 1-alkylcyclopropanecarbonyl acetoanilide-series compounds, (for example, JP-A-4-218042 ("JP-A" means unexamined published Japanese patent application)); cyclomalonic acid diamide-type couplers (for example, JP-A-5-11416); pyrrole-2- or 3-yl- or indole-2- or 3-yl-carbonylacetoanilide-series couplers (for example, European Patent Publication Nos. 953870A1,

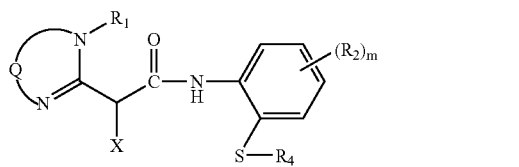

formula (I)

wherein Q represents a group of nonmetallic atoms that form a 5- to 7-membered ring in combination with the —N=C—N($R_1$)—; $R_1$ and $R_2$ each independently represents a substituent; $R_4$ represents an alkyl group; m represents an integer of 0 to 4; when m is 2 or more, the multiple $R_2$s may be the same or different, and the $R_2$s may bond each other to form a ring; and X represents a hydrogen atom, or a group capable of being split-off upon a coupling reaction with an oxidized product of a developing agent; and when $R_4$ represents a primary alkyl group, $R_1$ represents —$(CH_2)_3$O—$R_{101}$ in which $R_{101}$ is an alkyl group having 4 to 8 carbon atoms.

Further, the present invention is a silver halide color photographic light-sensitive material having at least one yellow dye-forming coupler represented by formula (I) in at least one layer provided on a support.

Other and further features and advantages of the invention will appear more fully from the following description.

DETAILED DESCRIPTION OF THE INVENTION

The inventors, having made investigations to solve the above-mentioned problems, have found out that, these problems can be solved by using a yellow dye-forming coupler represented by formula (I). Thus, the present invention has been made based on this finding.

According to the present invention, there is provided the following means:

(1) A yellow dye-forming coupler represented by formula (I) shown below;

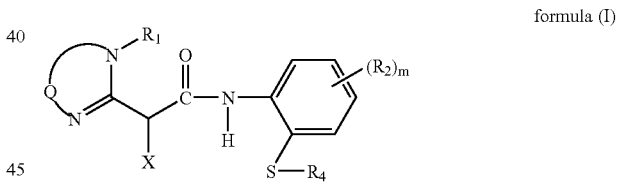

formula (I)

wherein Q represents a group of nonmetallic atoms that form a 5- to 7-membered ring in combination with the —N=C—N($R_1$)—; $R_1$ and $R_2$ each independently represents a substituent; $R_4$ represents an alkyl group; m represents an integer of 0 to 4; when m is 2 or more, the multiple $R_2$s may be the same or different, and the $R_2$s may bond each other to form a ring; and X represents a hydrogen atom, or a group capable of being split-off upon a coupling reaction with an oxidized product of a developing agent; and when $R_4$ represents a primary alkyl group, $R_1$ represents —$(CH_2)_3$O—$R_{101}$ in which $R_{101}$ is an alkyl group having 4 to 8 carbon atoms.

(2) A silver halide color photographic light-sensitive material comprising at least one yellow dye-forming coupler represented by formula (I) described in the above item (1) in at least one layer provided on a support.

(3) A yellow dye-forming coupler represented by formula (IA) shown below;

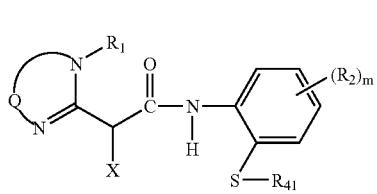

formula (IA)

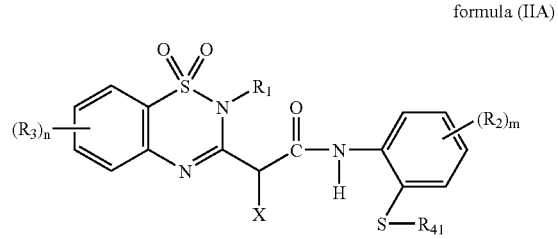

formula (IIA)

and 953871A1). The dyes formed from these couplers were improved in terms of both hue and molecular extinction coefficient of dyes formed, compared with the conventional ones. However, they were not satisfactory in image storability still. Further, owing to their complicated chemical structure, the synthesis route was longer, and consequently cost of the couplers was higher, causing a practical problem. In addition, there were proposed acetate ester-series and acetoanilide-series couplers to which 1,2,4-benzothiadiazine-1,1-dioxide is bonded (for example, U.S. Pat. No. 3,841,880, JP-A-52-82423 and JP-A-2-28645). However, these couplers were low in color-forming property, and they were inferior in sharpness of a peak of the absorption curve owing to the foot portion on the longer wavelength side. Therefore, improvement of these properties has been desired.

SUMMARY OF THE INVENTION

The present invention is a yellow dye-forming coupler represented by formula (I) shown below;

wherein Q represents a group of nonmetallic atoms that form a 5- to 7-membered ring in combination with the —N═C—N($R_1$)—; $R_1$ and $R_2$ each independently represents a substituent; $R_{41}$ represents a secondary or tertiary alkyl group; m represents an integer of 0 to 4; when m is 2 or more, the multiple $R_2$s may be the same or different, and the $R_2$s may bond each other to form a ring; and X represents a hydrogen atom, or a group capable of being split-off upon a coupling reaction with an oxidized product of a developing agent.

(4) A silver halide color photographic light-sensitive material comprising at least one yellow dye-forming coupler represented by formula (IA) according to the above item (3), in at least one layer provided on a support.

(5) The silver halide color photographic light-sensitive material according to the above item (4), wherein Q in the above-mentioned formula (IA) is a group represented by —C(—R11)═C(—R12)—$SO_2$— or —C(—R11)═C(—R12)—CO—, in which R11 and R12 are groups that bond with each other to form a 5- to 7-membered ring together with —C═C—, or they each independently represents a hydrogen atom or a substituent.

(6) The silver halide color photographic light-sensitive material according to the above item (4) or (5), wherein the yellow dye-forming coupler represented by formula (IA) is a yellow dye-forming coupler represented by formula (IIA):

wherein $R_1$ and $R_2$ each independently represents a substituent; $R_{41}$ represents a secondary or tertiary alkyl group; m represents an integer of 0 to 4; when m is 2 or more, the multiple $R_2$s may be the same or different, and the $R_2$s may bond each other to form a ring; $R_3$ represents a substituent; n represents an integer of 0 to 4; when n is 2 or more, the multiple $R_3$s may be the same or different, and the $R_3$s may bond each other to form a ring; and X represents a hydrogen atom, or a group capable of being split-off upon a coupling reaction with an oxidized product of a developing agent.

(Herein, the yellow dye-forming coupler and silver halide color photographic light-sensitive material described in the above items (3) to (6) may be collectively referred to as a first embodiment of the present invention.)

(7) A yellow dye-forming coupler represented by formula (IB) shown below;

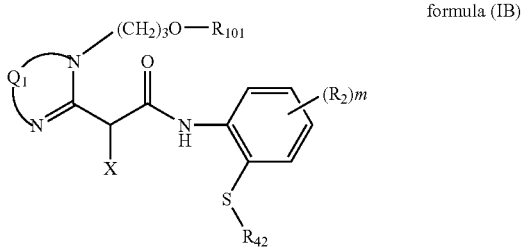

formula (IB)

wherein $Q_1$ represents a group of nonmetallic atoms that form a 5- to 7-membered ring in combination with the —N═C—N(($CH_2$)$_3$O—$R_{101}$)—; $R_{101}$ represents an alkyl group having 4 to 8 carbon atoms; $R_2$ represents a substituent; $R_{42}$ represents a primary alkyl group; m represents an integer of 0 to 4; when m is 2 or more, the multiple $R_2$s may be the same or different, and the $R_2$S may bond each other to form a ring; and X represents a hydrogen atom, or a group capable of being split-off upon a coupling reaction with an oxidized product of a developing agent.

(8) A silver halide color photographic light-sensitive material comprising at least one yellow dye-forming coupler represented by formula (IB) according to the above item (7), in at least one layer provided on a support.

(9) The silver halide color photographic light-sensitive material according to the above item (8), wherein $Q_1$ in the above-mentioned formula (IB) is a group represented by —C(—R11)═C(—R12)—$SO_2$— or —C(—R11)═C(—R12)—CO—, in which R11 and R12 are groups that bond with each other to form a 5- to 7-membered ring together with —C═C—, or they each independently represent a hydrogen atom or a substituent.

(10) The silver halide color photographic light-sensitive material according to the above item (8) or (9), wherein the yellow dye-forming coupler represented by formula (IB) is a yellow dye-forming coupler represented by formula (IIB):

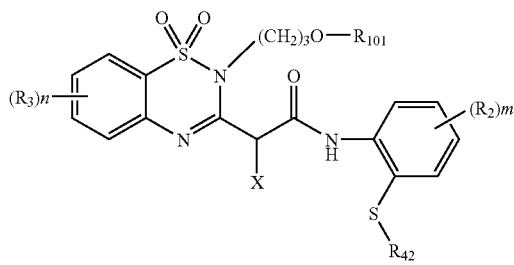

formula (IIB)

wherein $R_{101}$ represents an alkyl group having 4 to 8 carbon atoms; $R_2$ represents a substituent; $R_{42}$ represents a primary alkyl group; m represents an integer of 0 to 4; when m is 2 or more, the multiple $R_2$s may be the same or different, and the $R_2$s may bond each other to form a ring; $R_3$ represents a substituent; n represents an integer of 0 to 4; when n is 2 or more, the multiple $R_3$s may be the same or different, and the $R_3$s may bond each other to form a ring; and X represents a hydrogen atom, or a group capable of being split-off upon a coupling reaction with an oxidized product of a developing agent.

(11) The silver halide color photographic light-sensitive material according to one of the above items (8) to (10), wherein $R_2$ in formula (IB) or formula (IIB) represents a t-butyl group.

(Herein, the yellow dye-forming coupler and silver halide color photographic light-sensitive material described in the above items (7) to (11) may be collectively referred to as a second embodiment of the present invention.)

Herein, the present invention means to include both the first embodiment and the second embodiment, unless otherwise specified.

The present invention is explained below in detail.

The term "aliphatic group" used in the present specification means such groups, in which the aliphatic portion may be a saturated or unsaturated, straight chain, branched chain, or a cycle, and the aliphatic portion embraces, for example, an alkyl group, an alkenyl group, a cycloalkyl group, and a cycloalkenyl group; and these can be unsubstituted or substituted. Further, the term "aryl group" used herein means a substituted or unsubstituted, monocyclic or condensed ring. The term "heterocyclic group" used herein means such groups, in which the heterocycle portion contains a hetero atom(s) (such as nitrogen, sulfur and oxygen atoms) in the ring skeleton, and the heterocycle embraces a substituted or unsubstituted, saturated or unsaturated, and monocyclic or condensed ring.

The term "substituent" used in the present specification means any groups or atoms that are able to substitute for other groups or atoms; and embraces, for example, an aliphatic group, an aryl group, a heterocyclic group, an acyl group, an acyloxy group, an acylamino group, an aliphatic oxy group, an aryloxy group, a heterocyclic oxy group, an aliphatic oxycarbonyl group, an aryloxycarbonyl group, a heterocyclic oxycarbonyl group, a carbamoyl group, an aliphatic sulfonyl group, an arylsulfonyl group, a heterocyclic sulfonyl group, an aliphatic sulfonyloxy group, an arylsulfonyloxy group, a heterocyclic sulfonyloxy group, a sulfamoyl group, an aliphatic sulfonamido group, an aryl sulfonamido group, a heterocyclic sulfonamido group, an amino group, an aliphatic amino group, an arylamino group, a heterocyclic amino group, an aliphatic oxycarbonylamino group, an aryloxycarbonylamino group, a heterocyclic oxycarbonylamino group, an aliphatic sulfinyl group, an aryl sulfinyl group, an aliphatic thio group, an arylthio group, a hydroxy group, a cyano group, a sulfo group, a carboxyl group, an aliphatic oxyamino group, an aryloxyamino group, a carbamoylamino group, a sulfamoylamino group, a halogen atom, a sulfamoylcarbamoyl group, a carbamoylsulfamoyl group, a dialiphatic oxyphosphinyl group, and a diaryloxyphosphinyl group.

The dye-forming coupler of the present invention will be explained below, referring to the formulae (IA) and (IB), and these explanations, as they are, can also be applied to the formula (I) that includes said formulae (IA) and (IB).

First, the compound represented by formula (IA), which is the first embodiment of the compound represented by formula (I) of the present invention, is explained in detail. In the present specification, the compound is also referred to as a yellow dye-forming coupler.

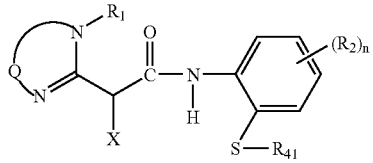

formula (IA)

In formula (IA), $R_1$ represents a substituent other than a hydrogen atom. Examples of the substituent include a halogen atom, an alkyl group, a cycloalkyl group (including a bicycloalkyl group), an alkenyl group, a cycloalkenyl group (including a bicycloalkenyl group), an alkynyl group, an aryl group, a heterocyclic group, a cyano group, a hydroxyl group, a nitro group, a carboxyl group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group (including an alkylamino group and an anilino group), an acylamino group, an aminocarbonylamino group, an alkoxycarbonylamino group, an aryloxycarbonylamino group, a sulfamoylamino group, an alkyl- or aryl-sulfonylamino group, a mercapto group, an alkylthio group, an arylthio group, a heterocyclic thio group, a sulfamoyl group, a sulfo group, an alkyl- or aryl-sulfinyl group, an alkyl- or aryl-sulfonyl group, an acyl group, an aryloxycarbonyl group, an alkoxycarbonyl group, a carbamoyl group, an arylazo group, a heterocyclic azo group, an imido group, a phosphino group, a phosphinyl group, a phosphinyloxy group, a phosphinylamino group, and a silyl group.

The above-mentioned substituent may be further substituted with another substituent. Examples of this another substituent are the same to the above-mentioned examples of the substituent.

$R_1$ is preferably a substituted or unsubstituted alkyl group. The total number of carbon atoms of $R_1$ is preferably in the range of 1 to 60, more preferably in the range of 4 to 50, and still more preferably in the range of 7 to 40. In the case that $R_1$ is a substituted alkyl group, examples of the substituent on the alkyl group include those atoms and groups exemplified as the substituent of the above-mentioned $R_1$.

In formula (IA), Q represents a group of nonmetallic atoms that forms a 5- to 7-membered ring in combination with the —N═C—N($R_1$)—. Preferably, the 5- to 7-membered ring thus formed is a substituted or unsubstituted, and monocyclic or condensed heterocycle. More preferably, the ring is one whose ring-forming atoms are selected from carbon, nitrogen and sulfur atoms. Still more preferably, Q represents a group represented by —C(—R11)═C(—R12)—SO$_2$— or —C(—R11)═C(—R12)—CO— (in the present specification, these expressions of the foregoing groups do not limit the bonding orientation of the groups in formula (IA), to the ones shown by these expressions). R11 and R12 are groups that bond each other to form a 5- to 7-membered ring together with the —C═C— moiety, or R11 and R12 each independently represents a hydrogen atom or a substituent. The 5- to 7-membered ring thus formed may be saturated or unsaturated, and the ring may be an alicyclic, aromatic or heterocyclic ring. Examples of the 5- to 7-membered ring include benzene, furan, thiophene, cyclopentane, and cyclohexane rings. These rings may further have a substituent. Examples of the substituent are the same as described as the examples of the above-mentioned substituent of $R_1$.

These substituents and the rings formed through bonding of multiple substituents may be further substituted with another substituent. Examples of this another substituent are the same as described as the examples of the above-mentioned substituent of $R_1$.

In formula (IA), $R_2$ represents a substituent other than a hydrogen atom. Examples of the substituent include those exemplified as the substituent of the above-mentioned $R_1$. $R_2$ is preferably a halogen atom (e.g., fluorine, chlorine, bromine), an alkyl group (e.g., methyl, isopropyl, t-butyl), an aryl group (e.g., phenyl, naphthyl), an alkoxy group (e.g., methoxy, isopropyloxy), an aryloxy group (e.g., phenoxy), an alkylthio group (e.g., methylthio, octylthio), an arylthio group (e.g., phenylthio, 2-methoxyphenylthio), an acyloxy group (e.g., acetyloxy), an amino group (e.g., dimethylamino, morpholino), an acylamino group (e.g., acetamido), a sulfonamido group (e.g., methanesulfonamido, benzenesulfonamido), an alkoxycarbonyl group (e.g., methoxycarbonyl), an aryloxycarbonyl group (e.g., phenoxycarbonyl), a carbamoyl group (e.g., N-methylcarbamoyl, N,N-diethylcarbamoyl), a sulfamoyl group (e.g., N-methylsulfamoyl, N,N-diethylsulfamoyl), an alkylsulfonyl group (e.g., methane sulfonyl), an arylsulfonyl group (e.g., benzene sulfonyl), a cyano group, a carboxyl group, or a sulfo group. More preferable examples of the substituent include an alkyl group, an aryl group, an alkoxy group, and an aryloxy group.

The total number of carbon atoms of $R_2$ is preferably in the range of 0 to 60, more preferably in the range of 0 to 50, and further more preferably in the range of 0 to 40.

In formula (IA), m represents an integer of 0 or more and 4 or less. When m is 2 or more, $R_2$s may be the same or different, and they may bond together to form a ring. In view of the effects of the present invention, m is preferably 0 or 1.

In formula (IA), $R_{41}$ represents a secondary or tertiary alkyl group, and it may have a substituent. Examples of the substituent are the same as those of the substituent of $R_1$ described above. For example, i-propyl, s-butyl, t-butyl, t-amyl, t-hexyl, t-octyl, and t-dodecyl groups are exemplified. The carbon atoms of the alkyl group are preferably in the range of 3 to 30, and more preferably in the range of 3 to 20. In view of effects of the present invention, a tertiary alkyl group is more preferable than a secondary alkyl group.

In formula (IA), X represents a hydrogen atom, or a group capable of being split-off upon a coupling reaction with an oxidized product of a developing agent. Examples of the group capable of being split-off upon a coupling reaction with an oxidized product of a developing agent include a group that splits off with a nitrogen, oxygen, or sulfur atom (a splitting-off atom); a halogen atom (e.g., chlorine, bromine), and the like.

Examples of the group that splits off with a nitrogen atom include a heterocyclic group (preferably a 5- to 7-membered substituted or unsubstituted, saturated or unsaturated aromatic (herein the term "aromatic" is used to embrace a substance that has (4n+2) cyclic conjugated electrons) or non-aromatic, monocyclic or condensed heterocyclic group; more preferably a 5- or 6-membered heterocyclic group having ring-forming atoms selected from carbon, nitrogen, oxygen and sulfur atoms and having at least one hetero atom selected from nitrogen, oxygen and sulfur atoms; specific examples of the heterocyclic group include succinimido, maleinimido, phthalimido, diglycolimido, pyrrole, pyrazole, imidazole, 1,2,4-triazole, tetrazole, indole, benzopyrazole, benzimidazole, benzotriazole, imidazoline-2,4-dione, oxazolidine-2,4-dione, thiazolidine-2-one, benzimidazoline-2-one, benzoxazoline-2-one, benzothiazoline-2-one, 2-pyrroline-5-one, 2-imidazoline-5-one, indoline-2,3-dione, 2,6-dioxypurine parabanic acid, 1,2,4-triazolidine-3,5-dione, 2-pyridone, 4-pyridone, 2-pyrimidone, 6-pyridazone, 2-pyrazone, 2-amino-1,3,4-thiazolidine-4-one), a carbonamido group (e.g., acetamido, trifluoroacetamido), a sulfonamido group (e.g., methanesulfonamido, benzenesulfonamido), an arylazo group (e.g., phenylazo, naphthylazo), and a carbamoylamino group (e.g., N-methyl carbamoylamino).

Preferred of the group that splits off with a nitrogen atom is a heterocyclic group, and more preferably it is an aromatic heterocyclic group having 1, 2, 3 or 4 ring-forming nitrogen atoms, or a heterocyclic group represented by the following formula (L):

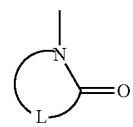

formula (L)

wherein L represents a moiety that forms a 5- to 6-membered nitrogen-containing heterocycle with the —NC(═O)—.

Examples of the moiety are enumerated in the explanation of the above-mentioned heterocyclic group, and such moieties as enumerated above are more preferred.

Particularly preferably L is a moiety that forms a 5-membered nitrogen-containing heterocycle.

Examples of the group that splits off with an oxygen atom include an aryloxy group (e.g., phenoxy, 1-naphthoxy), a heterocyclic oxy group (e.g., pyridyloxy, pyrazolyloxy), an acyloxy group (e.g., acetoxy, benzoyloxy), an alkoxy group (e.g., methoxy, dodecyloxy), a carbamoyloxy group (e.g., N,N-diethylcarbamoyloxy, morpholinocarbamoyloxy), an aryloxycarbonyloxy group (e.g., phenoxycarbonyloxy), an alkoxycarbonyloxy group (e.g., methoxycarbonyloxy, ethoxycarbonyloxy), an alkylsulfonyloxy group (e.g., methanesulfonyloxy), and an aryl sulfonyloxy group (e.g., benzenesulfonyloxy, toluenesulfonyloxy).

Preferred of the group that splits off with an oxygen atom are an aryloxy group, an acyloxy group and a heterocyclic oxy group.

Examples of the group that splits off with a sulfur atom include an arylthio group (e.g., phenylthio, naphthylthio), a heterocyclic thio group (e.g., tetrazolylthio, 1,3,4-thiadiazolylthio, 1,3,4-oxazolylthio, benzimidazolyl thio), an alkylthio group (e.g., methylthio, octylthio, hexadecylthio), an alkylsulfinyl group (e.g., methane sulfinyl), an arylsulfinyl group (e.g., benzenesulfinyl), an arylsulfonyl group (e.g., benzenesulfonyl), and an alkylsulfonyl group (e.g., methansulfonyl).

Preferred of the group that splits off with a sulfur atom are an arylthio group and a heterocyclic thio group. A heterocyclic thio group is more preferred.

X may be substituted with a substituent. Examples of the substituent substituting on X include those exemplified as the above-mentioned substituent of $R_1$.

X is preferably a group that splits off with a nitrogen atom, group that splits off with an oxygen atom, or group that splits off with a sulfur atom. More preferably X is a group that splits off with a nitrogen atom, and further preferably X is one of the above-mentioned preferable examples of the group that splits off with a nitrogen atom, and they are preferable in the described order.

X may be a photographically useful group. Examples of the photographically useful group include a development inhibitor, a desilvering accelerator, a redox compound, a dye, a coupler, and precursors of these compounds.

In order to render the coupler immobile in the light-sensitive material, at least one of Q, $R_1$, X, and $R_2$ has preferably 8 to 60 carbon atoms, more preferably 8 to 50 carbon atoms in total respectively, including carbon atoms of substituent(s) thereon.

It is preferable, from the point of the effects of the present invention, that the compound represented by formula (IA) is a compound represented by formula (IIA). Here, the compound represented by formula (IIA) is also referred to as a yellow dye-forming coupler in the present specification. The compound represented by formula (IIA) is explained in detail below.

formula (IIA)

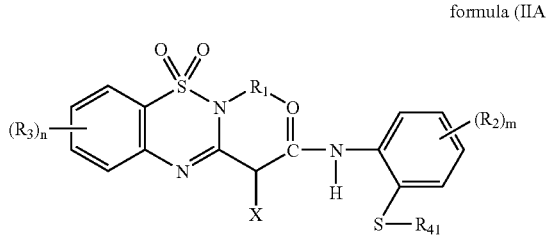

In formula (IIA), $R_1$, $R_2$, $R_{41}$, m, and X each have the same meanings as described in formula (IA). Preferable ranges thereof are also the same.

In formula (IIA), $R_3$ represents a substituent. Examples of the substituent include those groups and atoms exemplified as the above-mentioned substituent of $R_1$. Preferably $R_3$ is a halogen atom (e.g., fluorine, chlorine, bromine), an alkyl group (e.g., methyl, isopropyl), an aryl group (e.g., phenyl, naphthyl), an alkoxy group (e.g., methoxy, isopropyloxy), an aryloxy group (e.g., phenoxy), an acyloxy group (e.g., acetyloxy), an amino group (e.g., dimethylamino, morpholino), an acylamino group (e.g., acetamido), a sulfonamido group (e.g., methanesulfonamido, benzenesulfonamido), an alkoxycarbonyl group (e.g., methoxycarbonyl), an aryloxycarbonyl group (e.g., phenoxycarbonyl), a carbamoyl group (e.g., N-methylcarbamoyl, N,N-diethylcarbamoyl), a sulfamoyl group (e.g., N-methylsulfamoyl, N,N-diethylsulfamoyl), an alkylsulfonyl group (e.g., methane sulfonyl), an arylsulfonyl group (e.g., benzene sulfonyl), a cyano group, a carboxyl group, and a sulfo group.

n represents an integer of 0 or more but 4 or less. When n is 2 or more, the multiple $R_3$s may be the same or different, and the $R_3$s may bond each other to form a ring.

Preferable specific examples of the couplers represented by formula (IA) or (IIA) of the present invention are shown below. However, the present invention is not limited to these compounds. Herein, the present invention also embraces tautomers, in which the hydrogen atom at the coupling site (the hydrogen atom on the carbon atom to which X is substituting) is transferred on the nitrogen atom in the C=N portion bonding to the coupling site (the ring-constituting nitrogen atom that is not bonded with $R_1$).

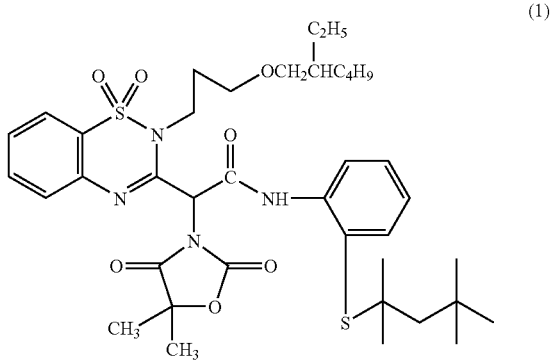

(1)

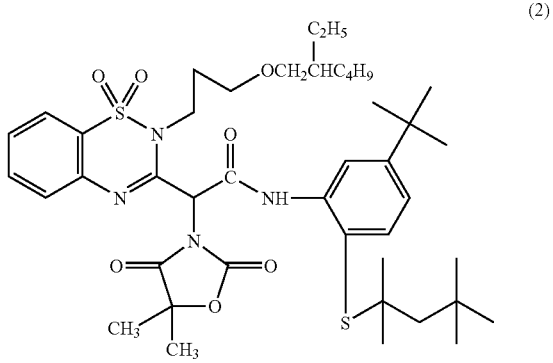

(2)

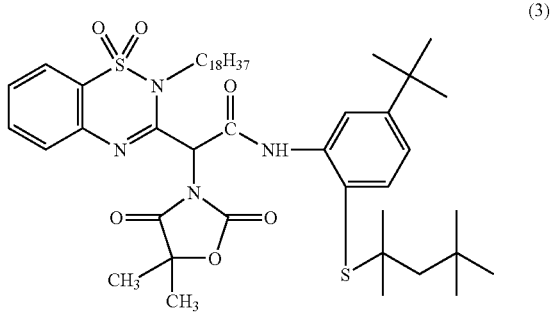

(3)

-continued
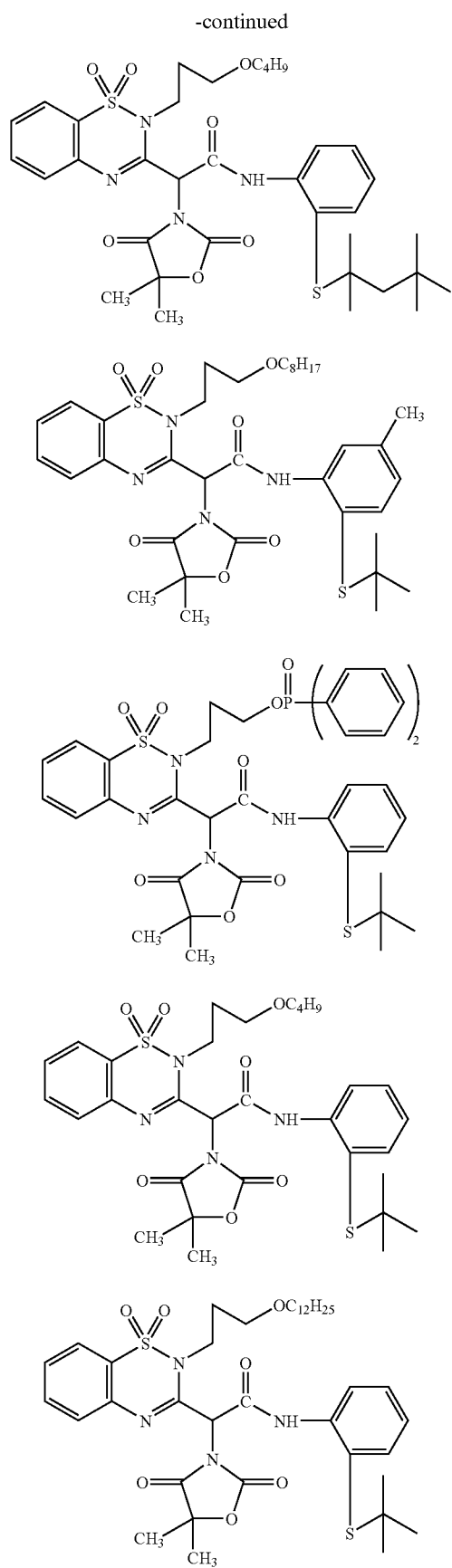
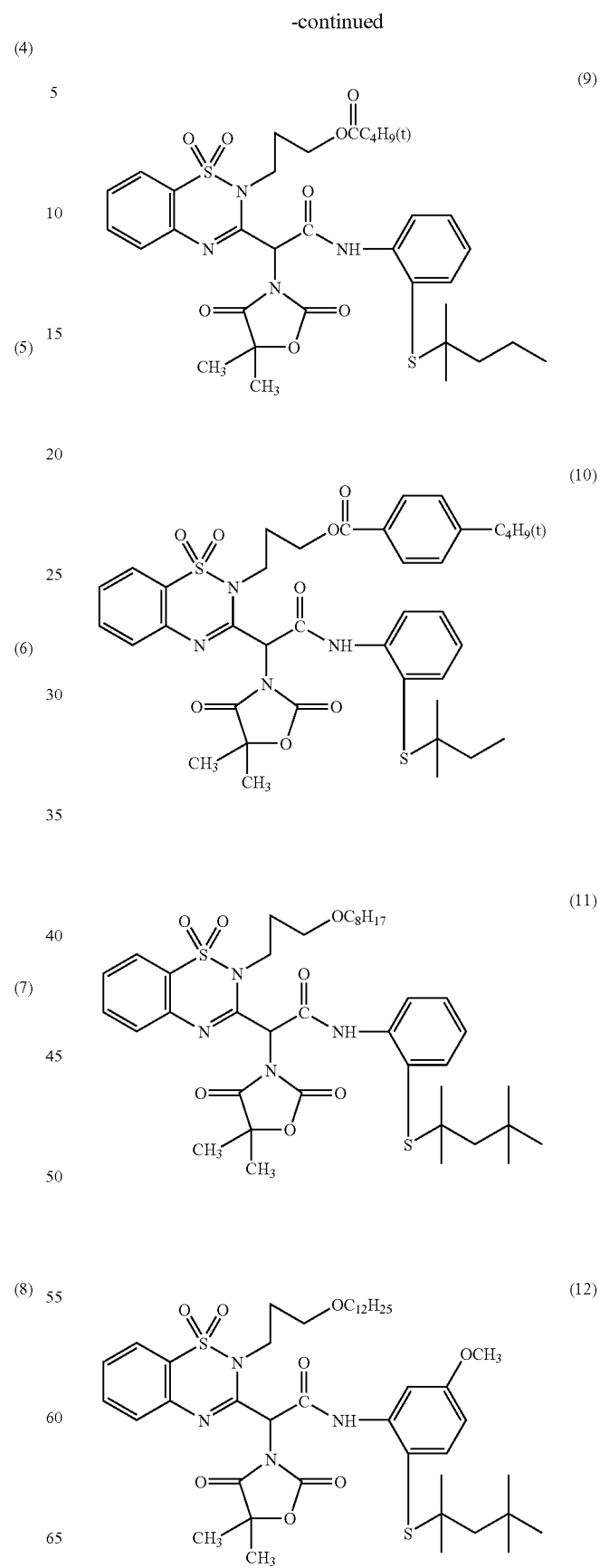

-continued
(13)
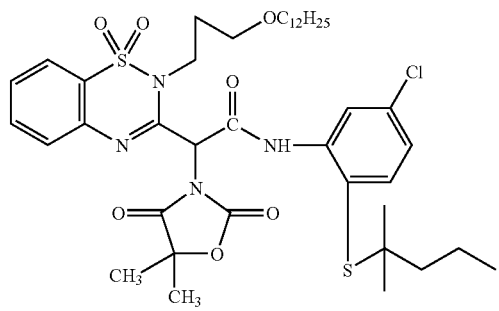
(14)
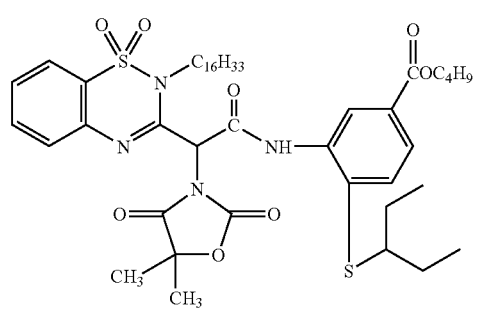
(15)
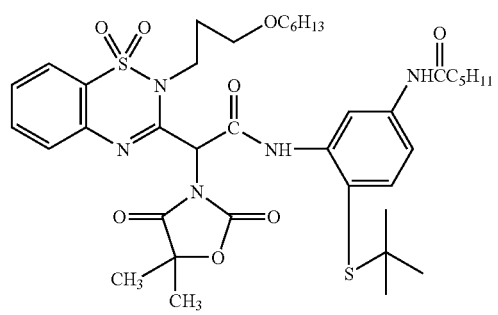
(16)
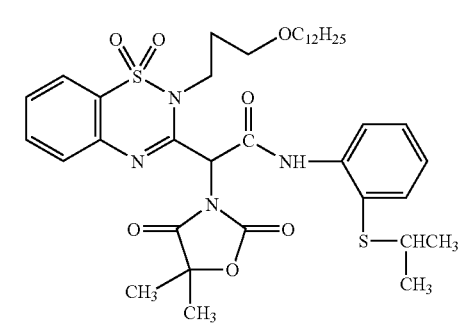
(17)
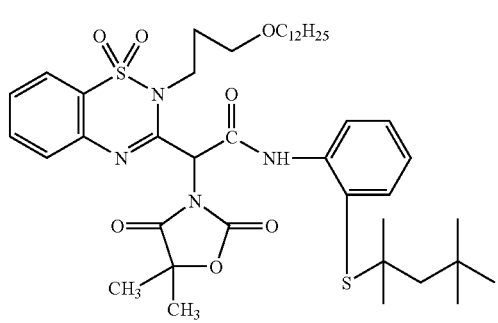
-continued
(18)
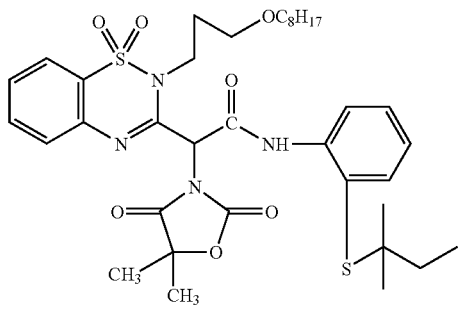
(19)
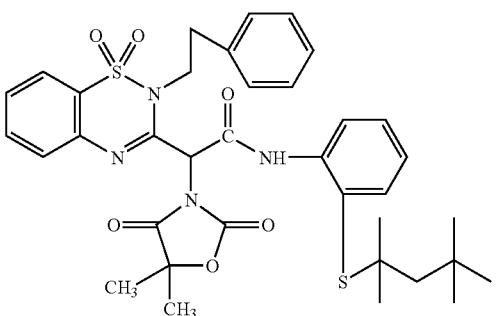
(20)
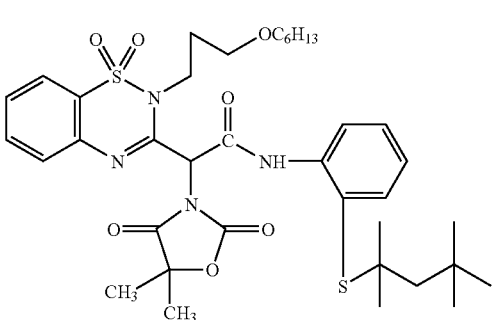
(21)
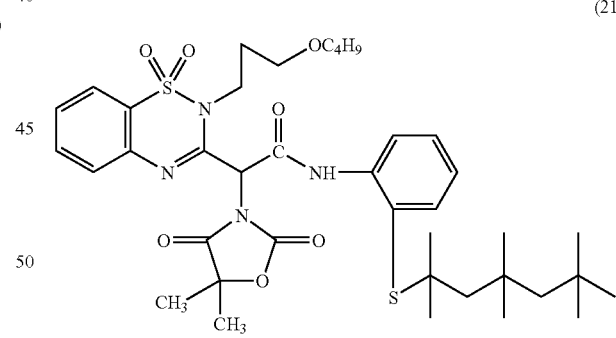
(22)
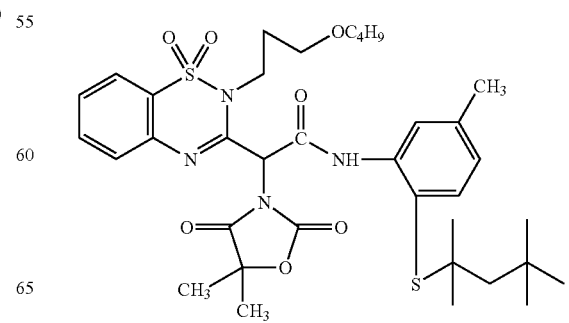

-continued

-continued

(33)
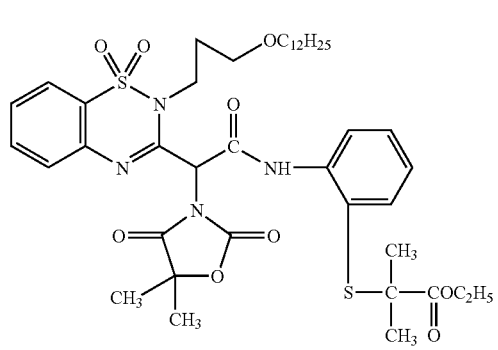

(34)
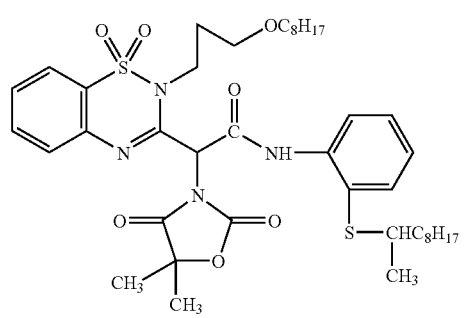

(35)
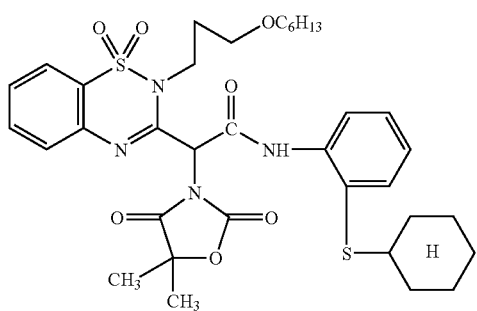

(36)
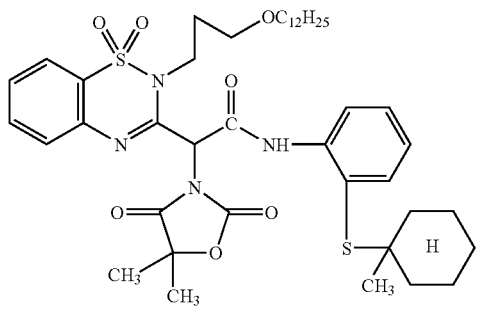

(37)
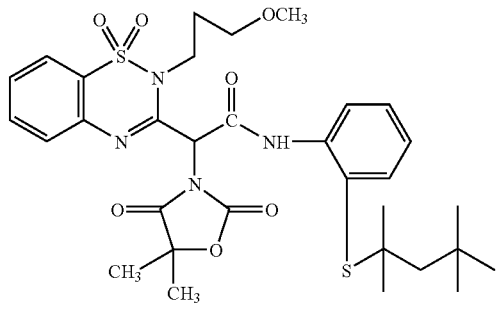

-continued

(38)
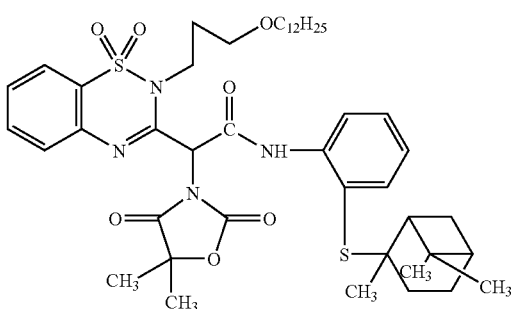

(39)
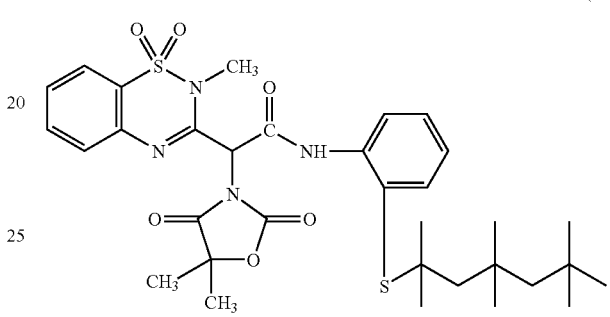

(40)
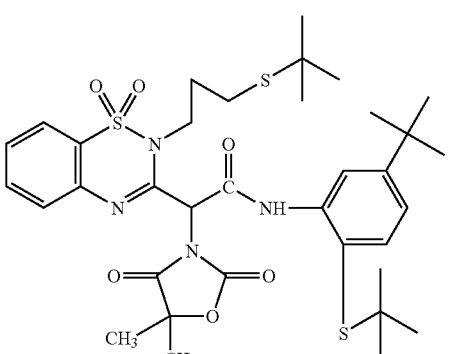

In the following explanation, when the exemplified compounds shown above are referred to, they are expressed as "coupler (x)" or "exemplified compound (x)", with using the number x labeled to each of the exemplified compounds in the parenthesis.

Specific synthetic examples of the compounds represented by the foregoing formula (IA) or (IIA) are described below.

SYNTHETIC EXAMPLE 1

Synthesis of the Coupler (4)

The coupler (4) was synthesized according to the following route:

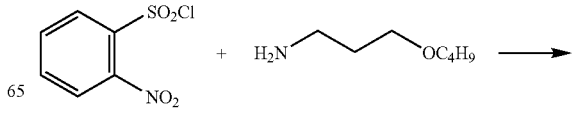

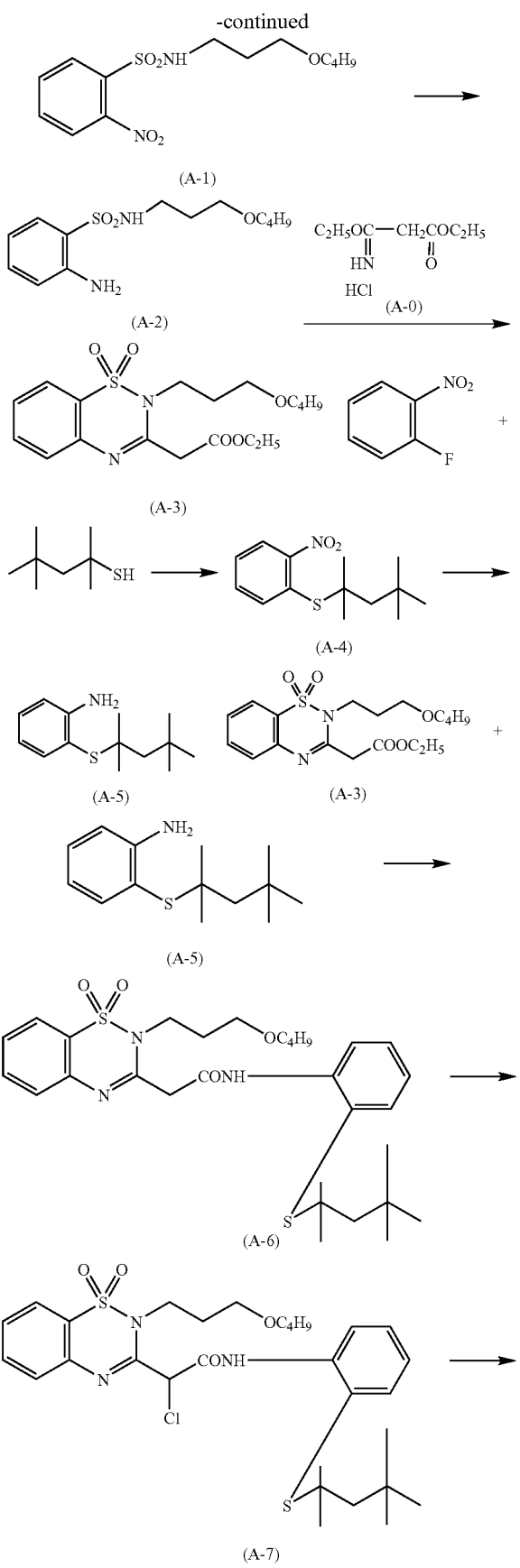

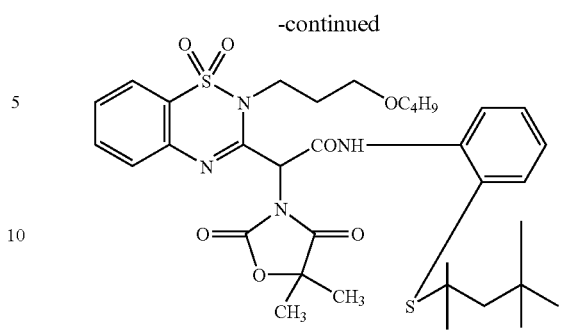

To a solution of 3-butoxypropylamine (150 g), triethylamine (192 ml) and acetonitrile (600 ml) under stirring and ice-cooling, 253 g of orthonitrobenzene sulfonyl chloride was gradually added. After elevating the temperature of the reaction system to room temperature, further agitation was continued for another 1 hour. Ethyl acetate and water were added for separation and extraction. The organic solvent layer was washed with dilute hydrochloric acid and saturated brine. After the organic solvent layer was dried with magnesium sulfate anhydride, the solvent was removed by vacuum distillation, to obtain 362 g of Compound (A-1) as a viscous oily product.

300.0 g of reduced iron and 30.0 g of ammonium chloride were dispersed in a mixture of isopropanol (1540 ml) and water (240 ml), and then stirred for 1 hour with heating under reflux. To the dispersion, 119 g of Compound (A-1) was gradually added. After stirring for another 2 hours with heating under reflux, the reaction mixture was suction-filtered through celite. Ethyl acetate and water were added to the filtrate for separation and extraction. The organic solvent layer was washed with saturated brine. After the organic solvent layer was dried with magnesium sulfate anhydride, the solvent was removed by vacuum distillation to obtain 327 g of Compound (A-2) as an oily product.

A solution of Compound (A-2) (327 g), hydrochloride (268.4 g) of iminoether (A-0), and ethyl alcohol (450 ml) was stirred for 1 hour with heating under reflux. After cooling, the mixture was suction-filtered. To the filtrated, 500 ml of p-xylene was added, and the solution was heated under reflux for 4 hours, with eliminating ethanol by distillation. The reaction solution was poured into 1000 ml of ice water, and then 500 ml of ethyl acetate was added for extraction. The organic solvent layer was washed with saturated brine twice, and then dried with magnesium sulfate anhydride. Magnesium sulfate was separated by filtration, and ethyl acetate and xylene were eliminated by distillation under reduced pressure. Crystallization of the obtained oily product from 1000 ml of n-hexane gave 370.1 g of Compound (A-3).

To t-octanethiol (146 g) were added dimethylformamide (500 ml) and potassium carbonate (138 g), and then ortho-fluoronitrobenzene (141 g) was added drop-wise over 30 minutes while stirring the solution at 80° C. under a nitrogen atmosphere. After heating and stirring at 80° C. for an additional 1 hour, the reaction solution was poured into 1000 ml of ice water, and then extraction was carried out with 700 ml of ethyl acetate. The organic solvent layer was washed with saturated brine twice, and then dried with magnesium sulfate anhydride. Magnesium sulfate was separated by filtration and the solvent was eliminated by vacuum distillation. Thus, 267 g of Compound (A-4) was obtained as an oily product.

300.0 g of reduced iron and 30.0 g of ammonium chloride were dispersed in a mixture of isopropanol (1540 ml) and water (240 ml), and then stirred for 1 hour with heating under reflux. To the dispersion, 267 g of Compound (A-4) was gradually added. After stirring for 2 hours with heating under reflux, the reaction mixture was suction-filtered through celite. Ethyl acetate and water were added to the filtrate for separation and extraction. The organic solvent layer was washed with saturated brine. After the organic solvent layer was dried with magnesium sulfate anhydride, the solvent was removed by vacuum distillation. Crystallization of the residue from a mixed solvent of methanol and water gave 198 g of Compound (A-5).

A mixture of Compound (A-3) (20 g) and Compound (A-5) (13.7 g) were heated and stirred at a temperature of 145 to 150° C. for 6 hours, to obtain a crude product of Compound (A-6). To the resultant crude product, 100 ml of ethyl acetate was added, and then, to the solution under stirring and ice-cooling, 7.1 g of N-chlorosuccinimide was added over 5 minutes. The solution was stirred for 30 minutes under ice cooling, and thereafter water was added for separation and extraction. The organic solvent layer was washed with saturated brine and dried with magnesium sulfate anhydride. Thereafter, the solvent was removed by vacuum distillation, to obtain a crude product of Compound (A-7).

5,5-dimethyloxazolidine-2,4-dione (15.5 g) and triethylamine (16.8 ml) were dissolved in N,N-dimethylacetamide (100 ml). To the solution under stirring at room temperature, a solution containing a whole amount of the previously synthesized crude product of Compound (A-7) dissolved in acetonitrile (30 ml) was added drop-wise over 10 minutes. Thereafter the temperature was elevated up to 80° C., and the reaction mixture was stirred for 3 hours. Ethyl acetate and ice water were added for separation and extraction. The organic solvent layer was washed with 0.1 N potassium hydroxide aqueous solution, diluted hydrochloric acid, and saturated brine. The organic solvent layer was dried with magnesium sulfate anhydride, and then the solvent was eliminated by vacuum distillation. Crystallization of the residue from 60 ml of methanol and recrystallization from 80 ml of methanol gave 23.4 g of Coupler (4). (Melting point, 127° C.)

SYNTHETIC EXAMPLE 2

Synthesis of the Coupler (8)

The coupler (8) was synthesized according to the following route:

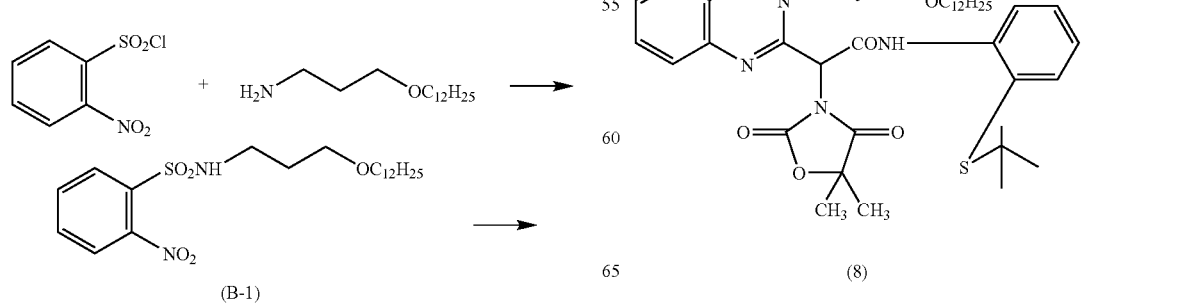

To a solution of 3-dodecyloxypropylamine (139 g), triethylamine (96 ml) and acetonitrile (500 ml), under stirring and ice-cooling, 126 g of ortho-nitrobenzene sulfonyl chloride was gradually added. After elevating the temperature of the reaction system to room temperature, further agitation was continued for 1 hour. Ethyl acetate and water were added to the solution for separation and extraction. The organic solvent layer was washed with dilute hydrochloric acid and saturated brine. After the organic solvent layer was dried with magnesium sulfate anhydride, the solvent was removed by vacuum distillation, to obtain 244 g of Compound (B-1) as a viscous oily product.

150.0 g of reduced iron and 15.0 g of ammonium chloride were dispersed in a mixture of isopropanol (1000 ml) and water (120 ml), and then the dispersion was stirred for 1 hour with heating under reflux. To the dispersion, 244 g of Compound (B-1) was gradually added. After stirring for an additional 2 hours with heating under reflux, the reaction mixture was suction-filtered through celite. Ethyl acetate and water were added to the filtrate for separation and extraction. The organic solvent layer was washed with saturated brine. After the organic solvent layer was dried with magnesium sulfate anhydride, the solvent was removed by vacuum distillation, to obtain 227 g of Compound (B-2) as an oily product.

A solution of Compound (B-2) (227 g), hydrochloride (134.2 g) of iminoether (A-0), and ethyl alcohol (300 ml) was stirred for 1 hour with heating under reflux. After cooling, the mixture was suction-filtered. To the filtrate, 300 ml of p-xylene was added, and heated under reflux for 4 hours, with eliminating ethanol by distillation. The reaction solution was poured into 800 ml of ice water, and then 300 ml of ethyl acetate was added for separation and extraction. The organic solvent layer was washed with saturated brine twice, and dried with magnesium sulfate anhydride. Magnesium sulfate was separated by filtration, and ethyl acetate and xylene were eliminated by vacuum distillation. Crystallization of the obtained oily product from ethyl acetate and methanol gave 181.9 g of Compound (B-3).

102 ml of concentrated sulfuric acid was added to 80 ml of ice water, and then 25.8 g of t-butanol was added drop-wise over 30 minutes under stirring at a temperature of 0 to 2° C. Thereafter, 30 g of 2-aminothiophenol was added drop-wise over 30 minutes at a temperature of 0 to 5° C. After the temperature was elevated up to the range of 20 to 25° C., the reaction mixture was stirred for 8 hours. The reaction mixture was poured into 1000 ml of an aqueous solution containing 150 g of sodium hydroxide dissolved therein, at the temperature of 40° C. or lower, for neutralization, and then separation and extraction was carried out with 500 ml of ethyl acetate. The organic solvent layer was washed with saturated brine twice, and dried with magnesium sulfate anhydride. Magnesium sulfate was separated by filtration and then the solvent was eliminated by vacuum distillation. Purification of thus-obtained oily product by a silica gel chromatography using ethyl acetate and n-hexane as eluants gave 40.8 g of Compound (B-4) as an oily product.

25 g of Compound (B-3) and 11.0 g of Compound (B-4) were heated and stirred at a temperature of 145 to 150° C. for 6 hours, to obtain a crude product of Compound (B-5). To the reaction crude product, 100 ml of ethyl acetate was added, and then 6.8 g of N-chlorosuccinimide was added over 5 minutes under stirring and ice cooling. After stirring the solution for 30 minutes with ice cooling, water was added for separation and extraction. The organic solvent layer was washed with saturated brine, and dried with magnesium sulfate anhydride. The solvent was eliminated by vacuum distillation, to obtain a crude product of Compound (B-6).

5,5-dimethyloxazolidine-2,4-dione (15.5 g) and triethylamine (16.8 ml) were dissolved in N,N-dimethylacetamide (100 ml). To the solution, a solution containing a whole amount of the previously synthesized crude product of Compound (B-6) dissolved in acetonitrile (30 ml), was added drop-wise over 10 minutes, at room temperature. After elevating the temperature up to 80° C., the reaction mixture was stirred for 3 hours. Ethyl acetate and water were added for separation and extraction. The organic solvent layer was washed with 0.1 N potassium hydroxide aqueous solution, diluted hydrochloric acid, and saturated brine. The organic solvent layer was dried with magnesium sulfate anhydride, and thereafter the solvents were eliminated by vacuum distillation. Crystallization of the residue from 50 ml of methanol, and recrystallization from 60 ml of methanol gave 25.3 g of Coupler (8). (Melting point, 87 to 88° C.)

SYNTHETIC EXAMPLE 3

Synthesis of the Coupler (22)

The coupler (22) was synthesized according to the following route:

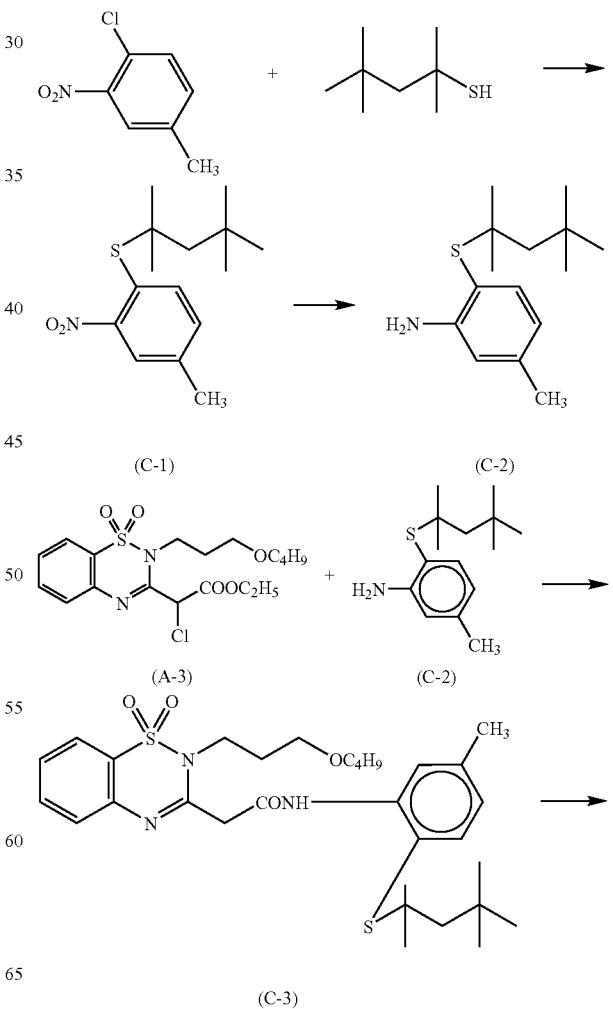

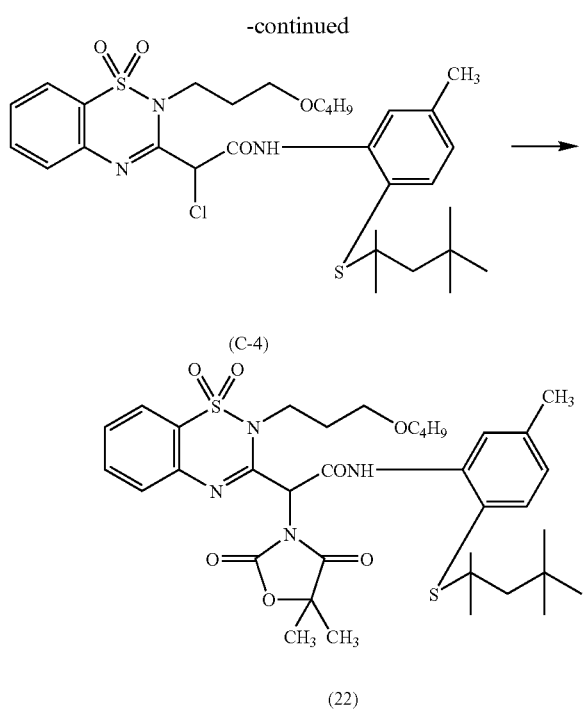

(22)

Dimethylformamide (120 ml) and potassium carbonate (38 g) were added to t-octanethiol (41.2 g). Then, while stirring the solution at 80° C. under a nitrogen atmosphere, 4-chloro-3-nitrotoluene (50 g) was added drop-wise over 30 minutes. After heating and stirring at 80° C. for an additional 1 hour, the reaction mixture was poured into 400 ml of ice water, and then separation and extraction was carried out with 300 ml of ethyl acetate. The organic solvent layer was washed with saturated brine twice, and dried with magnesium sulfate anhydride. After the magnesium sulfate was separated by filtration, the solvent was eliminated by vacuum distillation, to obtain 79.3 g of Compound (C-1) as an oily product.

100.0 g of reduced iron and 10.0 g of ammonium chloride were dispersed in a mixture of isopropanol (540 ml) and water (80 ml), and then stirred for 1 hour with heating under reflux. To the dispersion, 79.3 g of Compound (C-1) was gradually added. After stirring for an additional 2 hours with heating under reflux, the reaction mixture was suction-filtered through celite. Ethyl acetate and water were added to the filtrate for separation and extraction. The organic solvent layer was washed with saturated brine. After the organic solvent layer was dried with magnesium sulfate anhydride, the solvent was removed by vacuum distillation. Purification of the residue by a silica gel chromatography using ethyl acetate and n-hexane as eluants gave 67.5 g of Compound (C-2) as an oily product.

Compound (A-3)(61 g) and Compound (C-2)(40 g) were heated and stirred at a temperature of 145 to 150° C. for 6 hours, to obtain a crude product of Compound (C-3). To the resultant crude product, 200 ml of ethyl acetate was added, and then 21.7 g of N-chlorosuccinimide was added over 25 minutes to the solution under stirring and ice cooling. The solution was stirred for 30 minutes under ice cooling, and thereafter water was added for separation and extraction. The organic solvent layer was washed with saturated brine and dried with magnesium sulfate anhydride. Thereafter, the solvent was removed by vacuum distillation, to obtain a crude product of Compound (C-4).

5,5-dimethyloxazolidine-2,4-dione (38 g) and triethyl amine (41.2 ml) were dissolved in N,N-dimethylacetamide (100 ml). To this solution, a solution containing a whole amount of the previously synthesized crude product of Compound (C-4) dissolved in acetonitrile (30 ml) was added drop-wise over 10 minutes, at room temperature. Thereafter the temperature was elevated up to 80° C., and the reaction mixture was stirred for 3 hours. Ethyl acetate and water were added for separation and extraction. The organic solvent layer was washed with 0.1 N potassium hydroxide aqueous solution, diluted hydrochloric acid, and saturated brine. The organic layer was dried with magnesium sulfate anhydride, and then the solvent was eliminated by vacuum distillation. Crystallization of the residue from 100 ml of methanol and recrystallization from 150 ml of methanol gave 71.4 g of Coupler (22). (Melting point, 148 to 150° C.)

Next, the compound represented by formula (IB), which is the second embodiment of the compound represented by formula (I) of the present invention, is explained in detail. In the present specification, the compound is also referred to as a yellow dye-forming coupler.

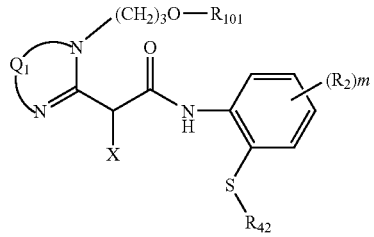

formula (IB)

In formula (IB), $R_{101}$ represents a substituted or unsubstituted alkyl group having 4 to 8 carbon atoms. Examples of the substituent that $R_{101}$ may have include those atoms and groups exemplified as the substituent of the above-mentioned $R_1$ in formula (IA).

The above substituent may be further substituted with another substituent. Examples of this another substituent include those atoms and groups mentioned as the substituent of the above-mentioned $R_{101}$.

$R_{101}$ is preferably an unsubstituted alkyl group having 4 to 6 carbon atoms, and it is more preferably n-butyl group.

In formula (IB), $Q_1$ represents a group of nonmetallic atoms that forms a 5- to 7-membered ring in combination with the —N═C—N((CH$_2$)$_3$O—R$_{101}$)—(Q$_1$ has substantially the same meaning as Q in formula (IA), though the literal explanation of $Q_1$ is different from that of Q in formula (IA).) Preferred examples of $Q_1$ include those rings and groups exemplified for Q in formula (IA). Further, all descriptions on features made for Q in formula (IA) apply to $Q_1$.

In formula (IB), $R_2$ has the same meaning as defined in formula (IA), and its specific examples and preferable range are also the same. However, in the second embodiment of the present invention, $R_2$ is more preferably a t-alkyl group, and furthermore preferably a t-butyl group, and most preferably a t-butyl group in the para-position to —SR$_{42}$.

In formula (IB), m has the same meaning as defined in the formula (IA), and its preferable range is also the same.

In formula (IB), $R_{42}$ represents a primary alkyl group, and this alkyl group may have a substituent. Examples of the substituent that $R_{42}$ may have are the same as those of the substituent on the aforementioned $R_{101}$. A preferable carbon numbers of $R_{42}$ including its substituent(s) is in the range of 3 to 30, more preferably in the range of 3 to 20, and furthermore preferably in the range of 6 to 12. As preferable examples of the substituent, an alkyl group and an aryl group can be exemplified, and an alkyl group is more preferable; and $R_{42}$ is most preferably a 2-ethylhexyl group.

The term "primary alkyl group" in this specification is used to indicate a carbon skeleton of an alkyl group in which, assuming that the carbon bonding to S in formula (IB) is designated as a central carbon, the central carbon has at least two hydrogen atoms.

In formula (IB), X has the same meaning as defined in formula (IA), and its specific examples and preferable range are also the same. However, in the second embodiment of the present invention, X is most preferably 5,5-dimethyloxazolidine-2,4-dione-3-yl group.

In order to render the coupler immobile in the light-sensitive material, at least one of $Q_1$, $R_{101}$, X, and $R_2$ has preferably 8 to 60 carbon atoms, more preferably 8 to 50 carbon atoms in total respectively, including carbon atoms of substituent(s) thereon.

It is preferable, from the point of the effects of the present invention, that the compound represented by formula (IB) is a compound represented by formula (IIB). Here, the compound represented by formula (IIB) is also referred to as a yellow dye-forming coupler in the present specification. The compound represented by formula (IIB) is explained in detail below.

formula (IIB)

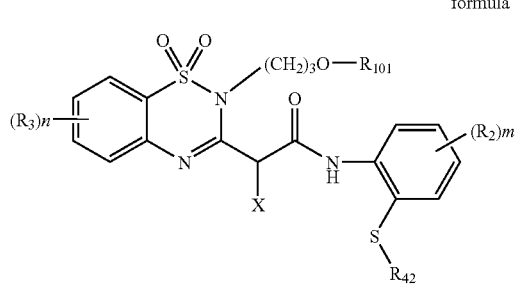

In formula (IIB), $R_{101}$, $R_2$, $R_{42}$, m, and X each have the same meanings as in formula (IB), and preferable ranges thereof are also the same.

In formula (IIB), $R_3$ has the same meaning as in formula (IIA), and preferable ranges thereof are also the same.

n has the same meaning as in formula (IIA), and preferable ranges thereof are also the same.

Preferable specific examples of the couplers represented by formula (IB) or (IIB) of the present invention are shown below. However, the present invention is not limited to these compounds. Herein, the present invention also embraces tautomers, in which the hydrogen atom at the coupling site (the hydrogen atom on the carbon atom to which X is substituting) is transferred on the nitrogen atom in the C=N portion bonding to the coupling site (the ring-constituting nitrogen atom that is not bonded with $(CH_2)_3O-R_{101}$).

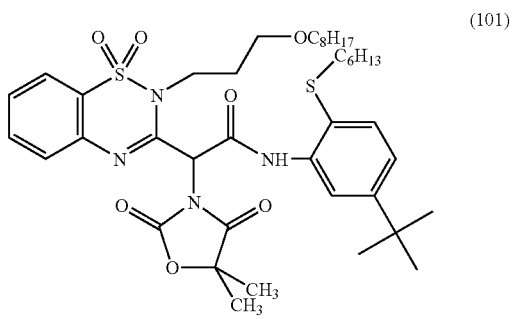

(101)

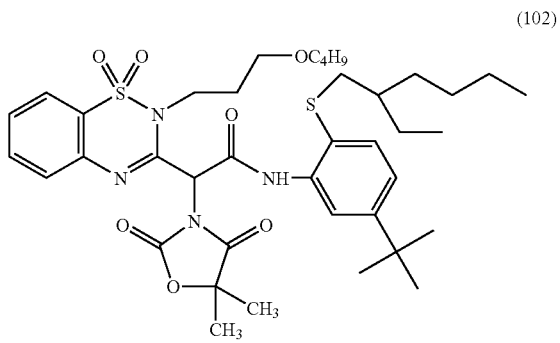

(102)

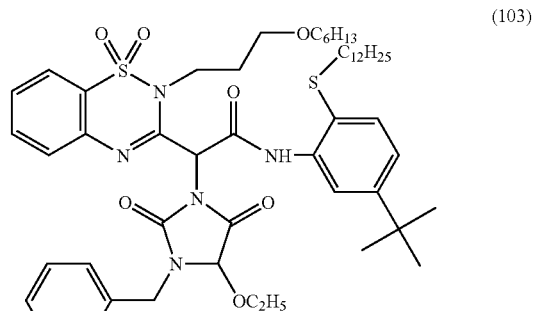

(103)

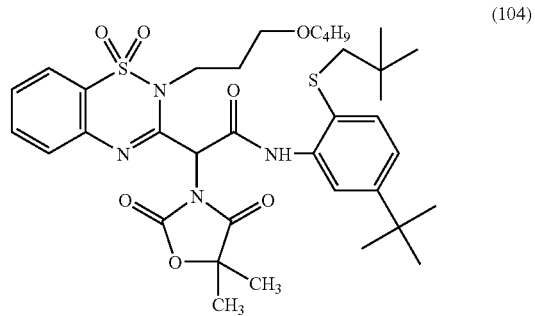

(104)

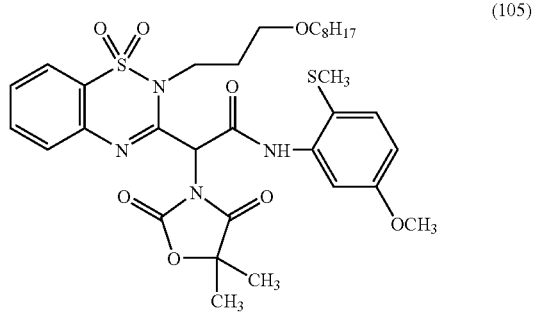

(105)

-continued
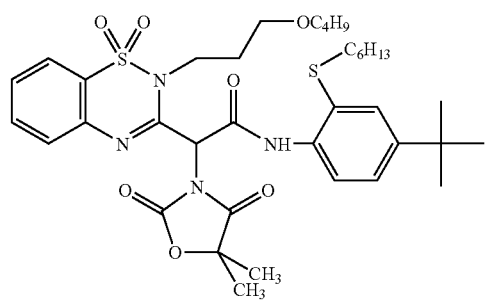
(106)
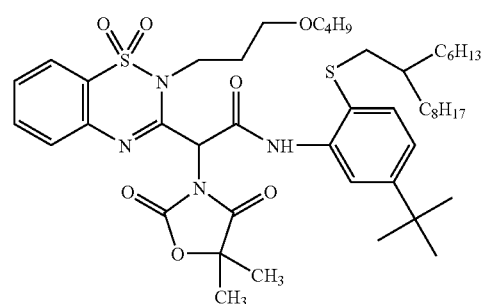
(107)
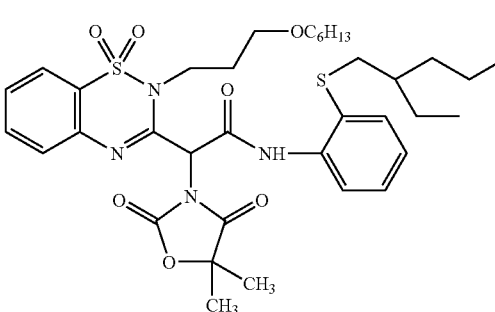
(108)
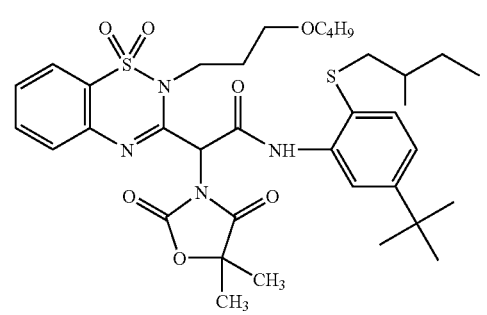
(109)
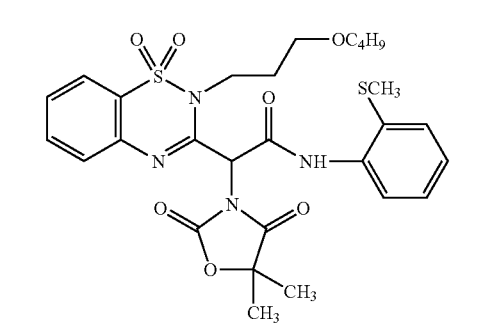
(110)
-continued
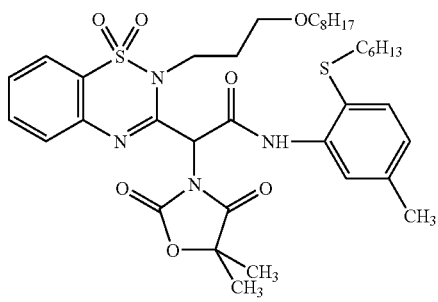
(111)
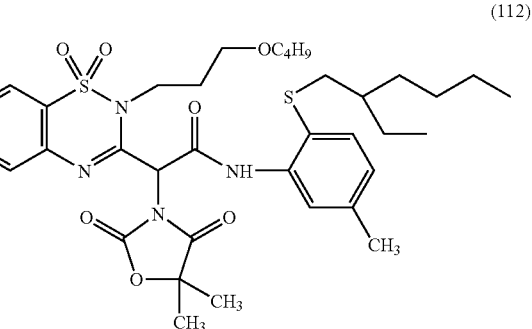
(112)
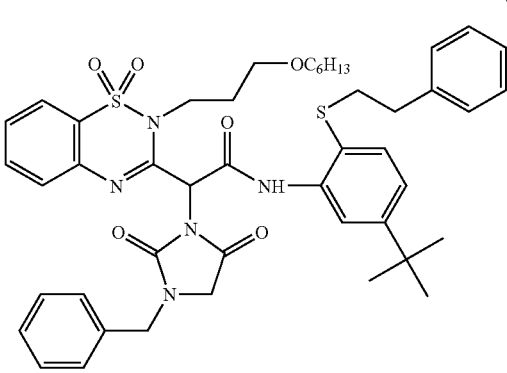
(113)
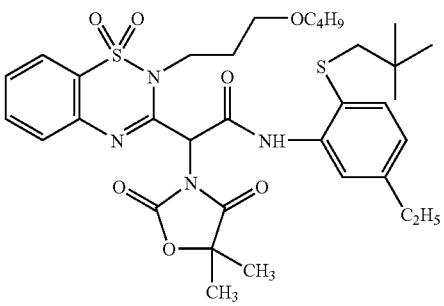
(114)
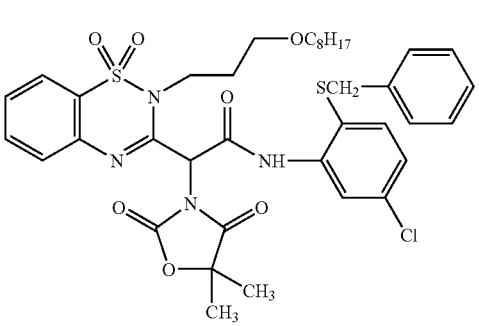
(115)

-continued
(116) 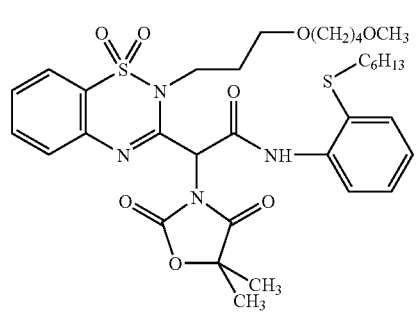
(117) 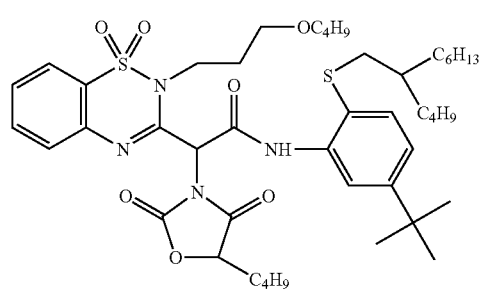
(118) 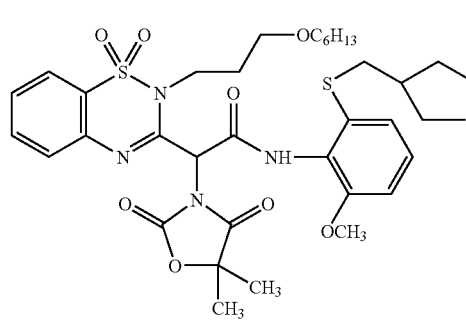
(119) 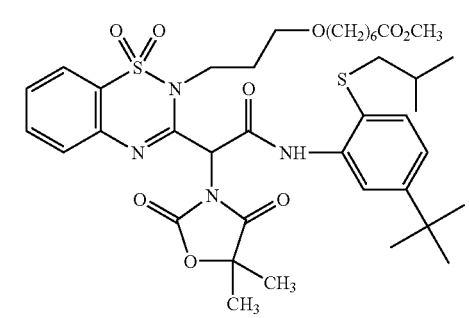
(120) 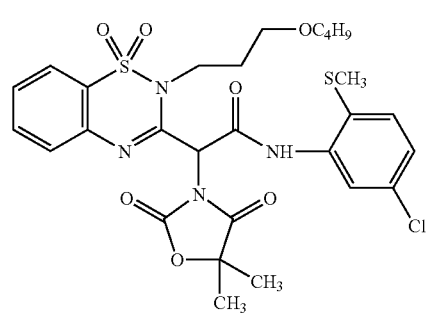
-continued
(121) 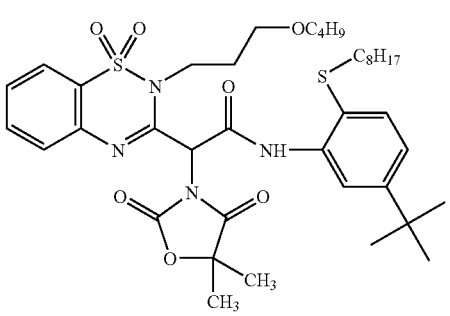
(122) 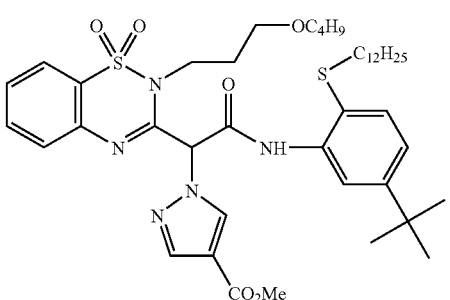
(123) 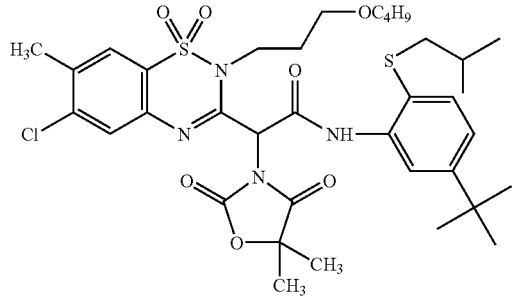
(124) 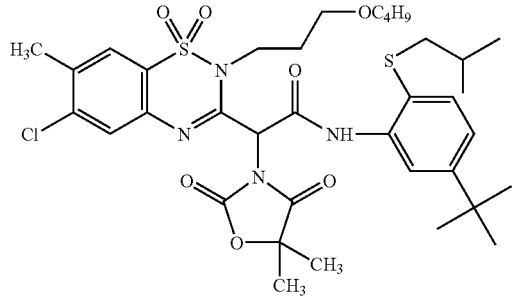
(125) 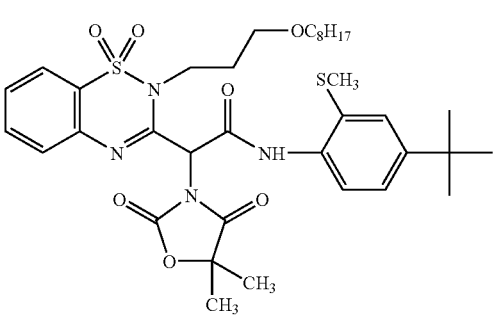

-continued
(126)
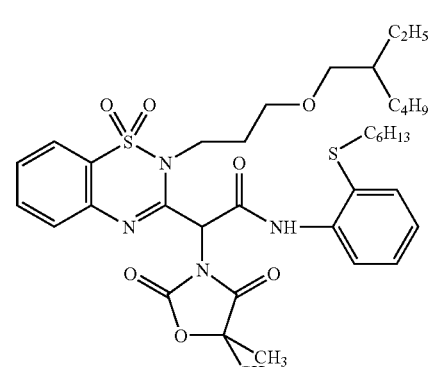
(127)
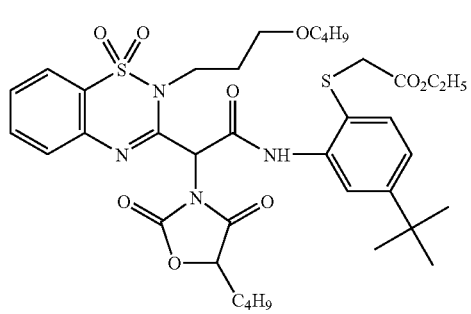
(128)
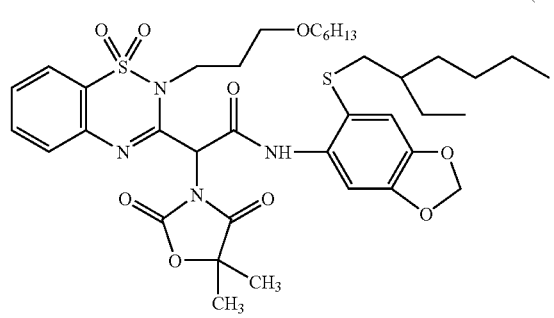
(129)
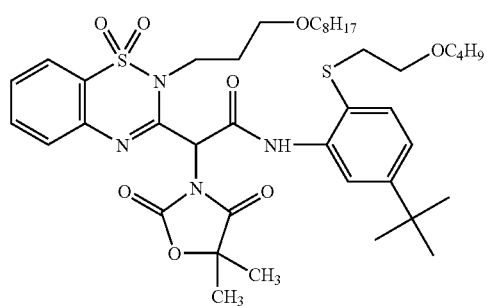
(130)
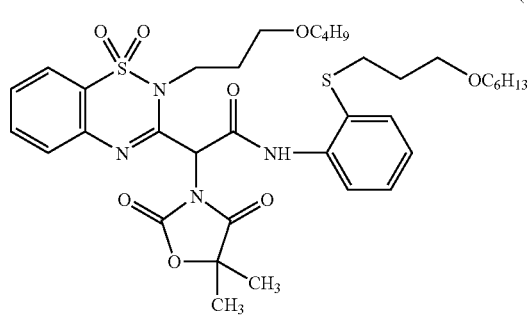
-continued
(131)
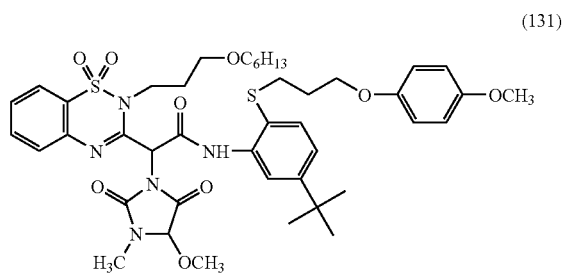
(132)
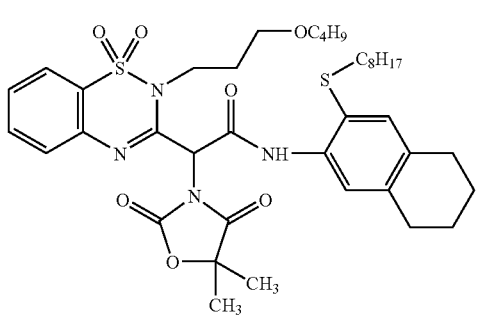
(133)
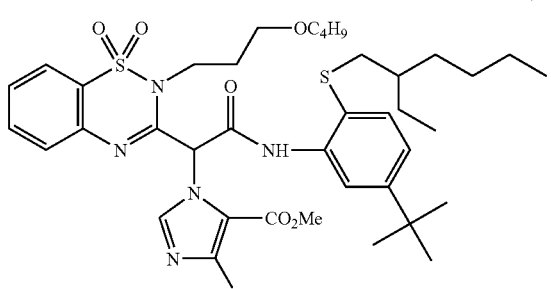
(134)
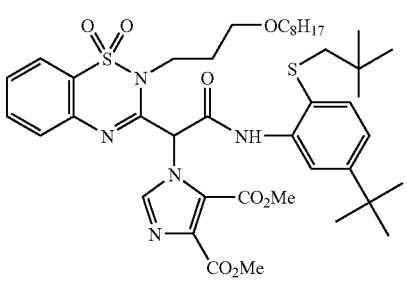
(135)
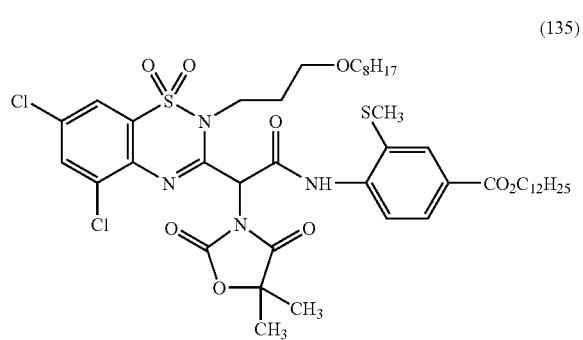

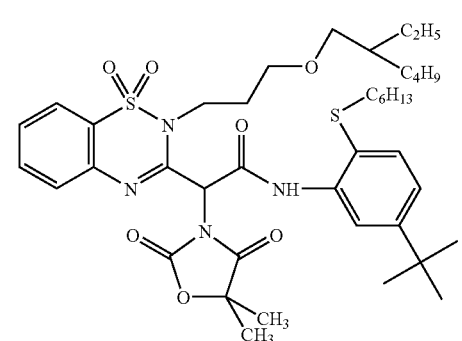
(136)
(137)
(138)
(139)
(140)
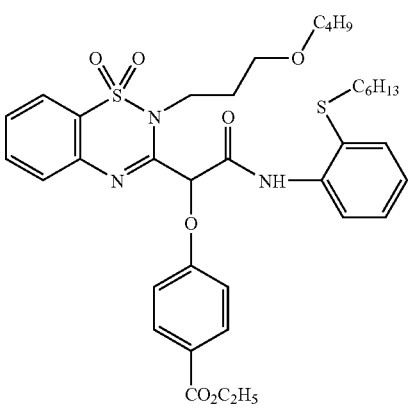
(141)
(142)
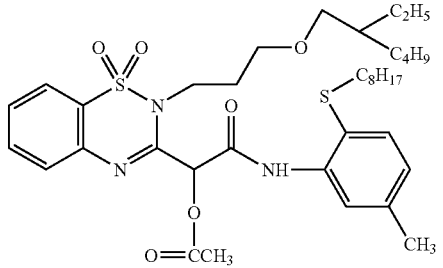
(143)
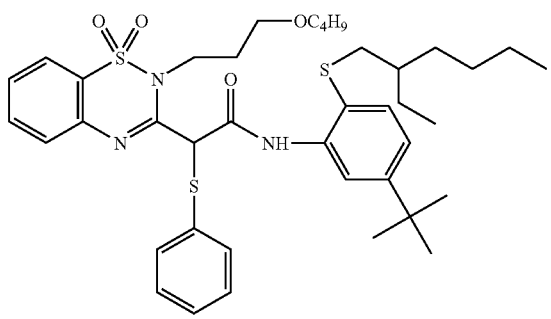
(144)

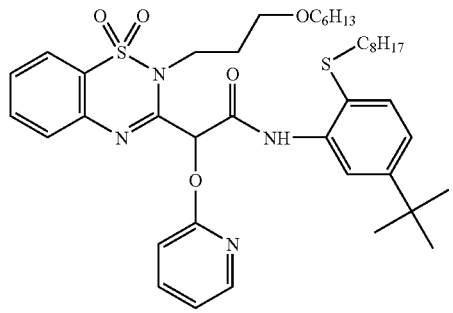

In the following explanation, when the exemplified compounds shown above are referred to, they are expressed as "coupler (x)" or "exemplified compound (x)", with using the number x labeled to each of the exemplified compounds in the parenthesis.

Specific synthetic examples of the compounds represented by the foregoing formula (IB) or (IIB) are described below.

SYNTHETIC EXAMPLE 4

Synthesis of the Coupler (102)

The coupler (102) was synthesized according to the following route:

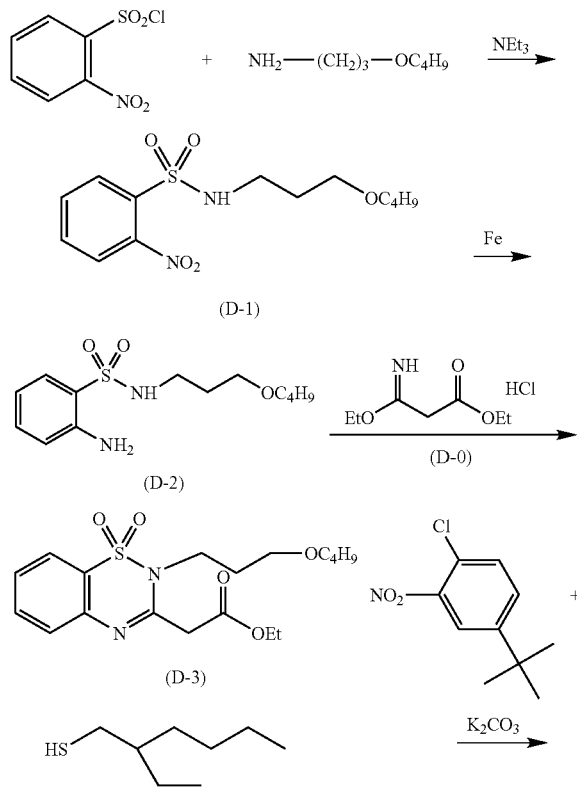

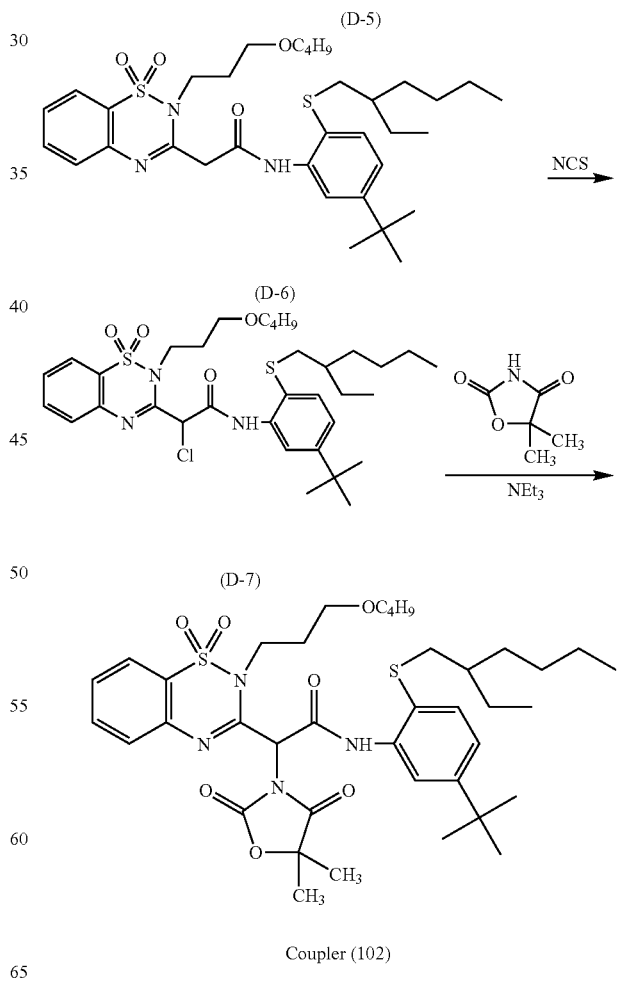

To a solution of 3-butoxypropylamine (150 g), triethylamine (192 ml) and acetonitrile (600 ml) under stirring and ice-cooling, 253 g of ortho-nitrobenzene sulfonyl chloride was gradually added. After the temperature of the reaction system was elevated to room temperature, agitation was continued for another 1 hour. Ethyl acetate and water were added for separation and extraction. The organic solvent layer was washed with dilute hydrochloric acid and saturated brine. After the organic solvent layer was dried with magnesium sulfate anhydride, the solvent was removed by vacuum distillation, to obtain 362 g of Compound (D-1) as a viscous oily product.

300.0 g of reduced iron and 30.0 g of ammonium chloride were dispersed in a mixture of isopropanol (1540 ml) and water (240 ml), and then heated under reflux and stirred for 1 hour. To the dispersion, 119 g of Compound (D-1) was gradually added. After heating under reflux with stirring for 2 hours, the reaction mixture was suction-filtered through celite. Ethyl acetate and water were added to the filtrate for separation and extraction. The organic solvent layer was washed with saturated brine. After the organic solvent layer was dried with magnesium sulfate anhydride, the solvent was removed by vacuum distillation, to obtain 327 g of Compound (D-2) as an oily product.

A solution of Compound (D-2) (327 g), hydrochloride (268.4 g) of iminoether (D-0), and ethyl alcohol (450 ml) was stirred for 1 hour with heating under reflux. After cooling, the mixture was suction-filtered. To the filtrate, 500 ml of p-xylene was added, and the solution was heated under reflux for 4 hours, with eliminating ethanol by distillation. The reaction solution was poured into 1000 ml of ice water, and then 500 ml of ethyl acetate was added for extraction. The organic solvent layer was washed with saturated brine twice, and then dried with magnesium sulfate anhydride. Magnesium sulfate was separated by filtration, and ethyl acetate and xylene were removed by distillation under reduced pressure. Crystallization of the obtained oily product from 1000 ml of n-hexane gave 370.1 g of Compound (D-3).

To a mixture of 2-ethylhexanethiol (343 g), N,N-dimethylacetamide (800 ml) and potassium carbonate (364 g), 4-t-butyl-2-nitrochlorobenzene (470 g) was added under a nitrogen atmosphere and heated and stirred at 90° C. for 2 hours. Thereafter, the reaction mixture was poured into 1000 ml of ice water, and then extraction was carried out with 1000 ml of ethyl acetate. The organic solvent layer was washed with saturated brine twice, and dried with magnesium sulfate anhydride. Magnesium sulfate was separated by filtration, and the solvents were removed by distillation under reduced pressure. Thus, 806 g of Compound (D-4) was obtained as an oily product.

740 g of reduced iron and 74.0 g of ammonium chloride were dispersed in a mixture of isopropanol (2200 ml) and water (370 ml), and then stirred for 1 hour with heating under reflux. To the dispersion, 806 g of Compound (D-4) was gradually added. After stirring for 2 hours with heating under reflux, the reaction mixture was suction-filtered through celite. Ethyl acetate and water were added to the filtrate for separation and extraction. The organic solvent layer was washed with saturated brine. After the organic solvent layer was dried with magnesium sulfate anhydride, the solvent was removed by vacuum distillation, to obtain 671 g of Compound (D-5) as an oily product.

A mixture of Compound (D-3) (110 g) and Compound (D-5) (96.2 g) were heated and stirred at a temperature of 145 to 150° C. for 6 hours, to obtain a crude product of (D-6). To the reaction crude product, 300 ml of ethyl acetate was added, and then 31.2 g of N-chlorosuccinimide was added over 5 minutes to the solution under stirring and ice cooling. After the solution was stirred for 30 minutes under ice cooling, water was added for separation and extraction. The organic solvent layer was washed with saturated brine and dried with magnesium sulfate anhydride. Thereafter, the solvent was removed by vacuum distillation, to obtain a crude product of Compound (D-7).

5,5-dimethyloxazolidine-2,4-dione (112 g) and triethylamine (120 ml) were dissolved in N,N-dimethylacetamide (100 ml). To this solution under stirring at room temperature, a solution containing a whole amount of the previously synthesized crude product of Compound (D-7) dissolved in N,N-dimethylacetamide (150 ml) was added drop-wise over 10 minutes. Thereafter the temperature of the solution was elevated up to 80° C., and the reaction mixture was stirred for 3 hours. Ethyl acetate and ice water were added for separation and extraction. The organic solvent layer was washed with 0.1 N potassium hydroxide aqueous solution, diluted hydrochloric acid, and saturated brine, and dried with magnesium sulfate anhydride. The solvent was eliminated by vacuum distillation. Crystallization of the residue from a mixed solvent of ethyl acetate/hexane gave 88.3 g of Coupler (102). (Melting point, 124 to 125° C.)

SYNTHETIC EXAMPLE 5

Synthesis of the Coupler (108)

The coupler (108) was synthesized according to the following route:

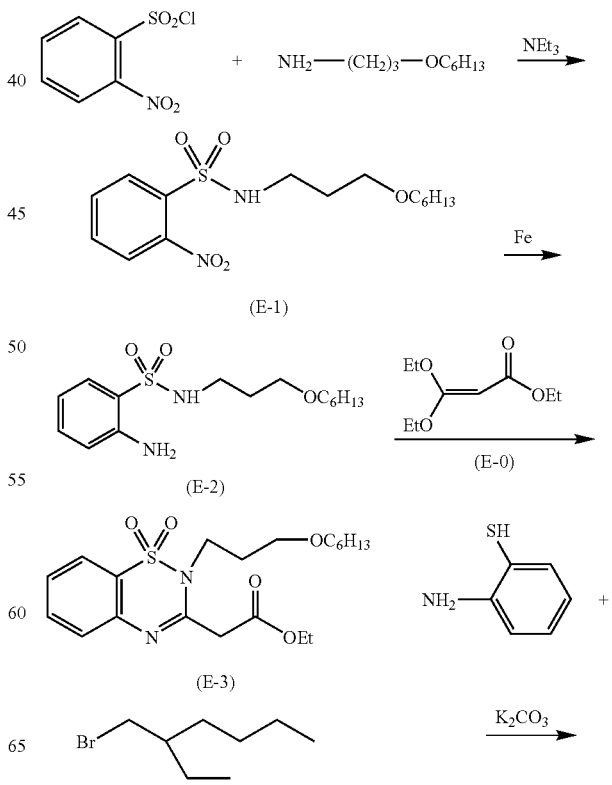

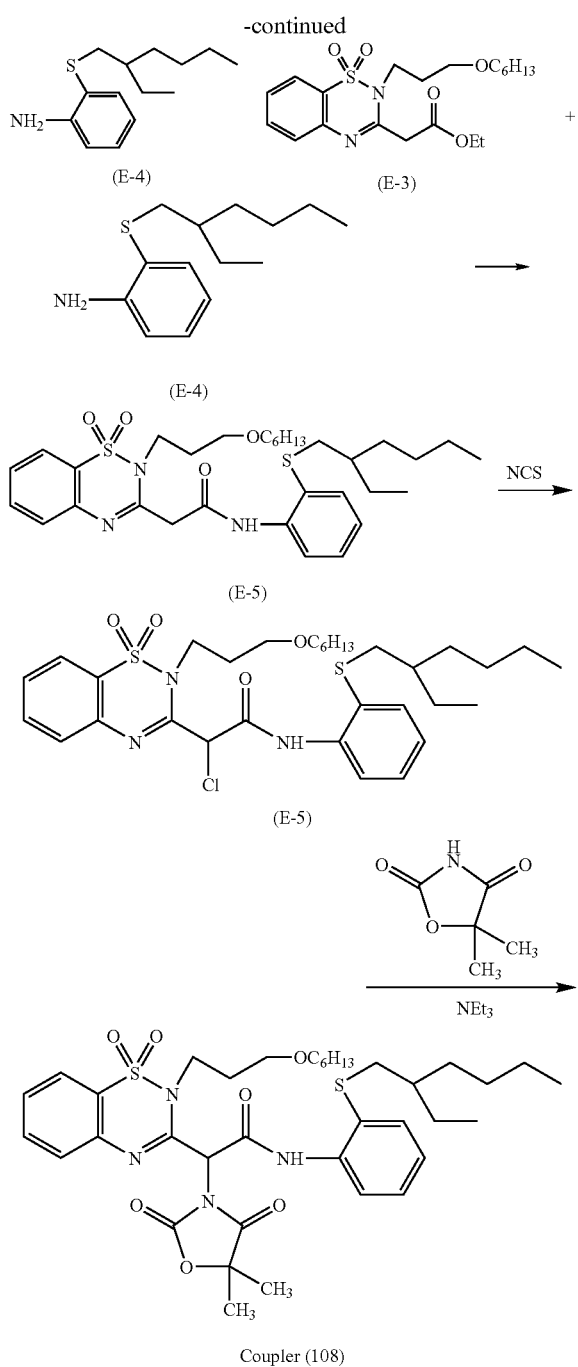

(E-4)

(E-3)

(E-4)

(E-5)

(E-5)

Coupler (108)

To a solution of 3-hexyloxypropylamine (120 g), triethylamine (105 ml) and acetonitrile (500 ml) under stirring and ice-cooling, 166 g of ortho-nitrobenzene sulfonyl chloride was gradually added. After elevating the temperature of the reaction system to room temperature, agitation was continued for further 3 hours. Ethyl acetate and water were added for separation and extraction. The organic solvent layer was washed with dilute hydrochloric acid and saturated brine. After the organic solvent layer was dried with magnesium sulfate anhydride, the solvent was removed by vacuum distillation, to obtain 252 g of Compound (E-1) as a viscous oily product.

396 g of reduced iron and 40.0 g of ammonium chloride were dispersed in a mixture of isopropanol (2600 ml) and water (300 ml), and then stirred for 1 hour with heating under reflux. To the dispersion, 487 g of Compound (E-1) was gradually added. After stirring for an another 2 hours with heating under reflux, the reaction mixture was suction-filtered through celite. Ethyl acetate and water were added to the filtrate for separation and extraction. The organic solvent layer was washed with saturated brine. After the organic solvent layer was dried with magnesium sulfate anhydride, the solvent was removed by vacuum distillation, to obtain 418 g of Compound (E-2) as an oily product.

A solution of Compound (E-2) (418 g), ethyl diethoxyacrylate (E-0) (300 g), p-toluene sulfonic acid monohydrate (2.5 g) and toluene (980 ml) was stirred for 1 hour with heating under reflux. Further 14.9 g of potassium t-butoxide was added, and the solution was heated under reflux for 5 hours, with eliminating ethanol by distillation. The reaction solution was poured into 800 ml of ice water, and then 800 ml of ethyl acetate and 20 ml of hydrochloric acid were added for separation and extraction. The organic solvent layer was washed with saturated brine twice, and dried with magnesium sulfate anhydride. Magnesium sulfate was separated by filtration, and ethyl acetate and toluene were eliminated by distillation under reduced pressure. Crystallization of the obtained oily product from methanol and water gave 323 g of Compound (E-3).

To a mixture comprising 2-ethylhexyl bromide (77.2 g), potassium carbonate (82.8 g) and N,N-dimethylformamide (200 ml), under a stream of $N_2$, 50.1 g of 2-aminothiophenol was added drop-wise over 30 minutes under ice cooling. After elevating the temperature to 40° C., the mixture was stirred for 2 hours. The reaction solution was poured to 500 ml of water, and 500 ml of ethyl acetate was used for separation and extraction. The organic solvent layer was washed with dilute hydrochloric acid and saturated brine, and dried with magnesium sulfate anhydride. After magnesium sulfate was separated by filtration, the solvent was removed by vacuum distillation, to obtain 94.1 g of Compound (E-4) as an oily product.

A mixture of Compound (E-3) (28.7 g), Compound (E-4) (16.6 g) and xylene (20 ml) was heated and stirred for 6 hours at a temperature of 145 to 150° C. After xylene was eliminated by distillation, the residue was purified by a silica gel column chromatography using ethyl acetate and n-hexane as eluents. 29.8 g of Compound (E-5) was obtained as an oily product.

To 100 ml of an ethyl acetate solution containing 28.9 g of Compound (E-5) under stirring and ice-cooling, 6.4 g of N-chlorosuccinimide was added over 5 minutes. After stirring for 30 minutes under ice cooling, water was added for separation and extraction. The organic layer was washed with saturated brine, and dried with magnesium sulfate anhydride. The solvent was eliminated by vacuum distillation, to obtain a crude product of Compound (E-6).

5,5-dimethyloxazolidine-2,4-dione (18.6 g) and triethylamine (20 ml) were dissolved in N,N-dimethylacetamide (100 ml). To this solution, a solution containing a whole amount of the previously synthesized crude product of Compound (E-6) dissolved in N,N-dimethylacetamide (30 ml) was added drop-wise over 10 minutes at room temperature. After elevating the temperature up to 70° C., the reaction mixture was stirred for 3 hours. Ethyl acetate and water were added for separation and extraction. The organic solvent layer was washed with 0.1 N potassium hydroxide aqueous solution, diluted hydrochloric acid, and saturated brine, and dried with magnesium sulfate anhydride. After these solvents were eliminated by vacuum distillation, the residue was purified by a silica gel column chromatography using ethyl acetate and n-hexane as eluents. 18.1 g of Coupler (108) was obtained as an oily product.

SYNTHETIC EXAMPLE 6

Synthesis of the Coupler (122)

The coupler (122) was synthesized according to the following route:

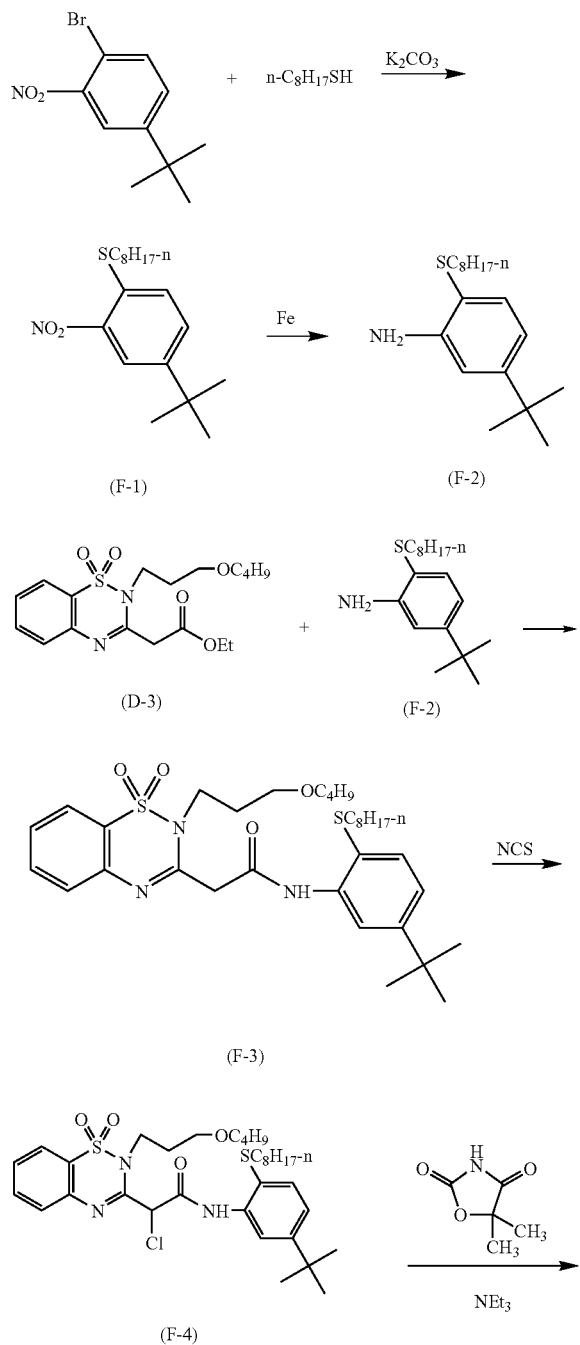

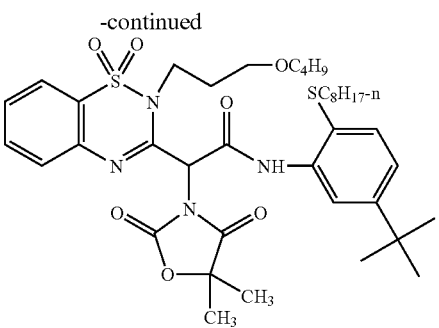

Coupler (122)

To a mixture of n-octanethiol (26.9 g), N,N-dimethylformamide (120 ml) and potassium carbonate (38 g), under a nitrogen atmosphere, 47.5 g of 4-t-butyl-2-nitrobromobenzene was added, and then heated and stirred at 80° C. for 1 hour. Thereafter, the reaction mixture was poured into 400 ml of ice water, and 300 ml of ethyl acetate was used for separation and extraction. The organic solvent layer was washed with saturated brine twice, and dried with magnesium sulfate anhydride. After magnesium sulfate anhydride was separated by filtration, the solvent was removed by distillation under reduced pressure, to obtain 58.0 g of Compound (F-1) as an oily product.

84.0 g of reduced iron and 8.4 g of ammonium chloride were dispersed in a mixture of isopropanol (480 ml) and water (80 ml), and then stirred for 1 hour with heating under reflux. To this dispersion, 58.0 g of Compound (F-1) was gradually added. After further addition of 2 ml of acetic acid and stirring for 2 hours under heating and reflux, the reaction mixture was suction-filtered through celite. Ethyl acetate and water were added to the filtrate for separation and extraction. The organic solvent layer was washed with saturated brine. After the organic solvent layer was dried with magnesium sulfate anhydride, the solvent was removed by vacuum distillation. The residue was purified by a silica gel column chromatography using ethyl acetate and n-hexane as eluents. 43.3 g of Compound (F-2) was obtained as an oily product.

A mixture of Compound (D-3) (53.6 g), Compound (F-2) (43.0 g) and xylene (100 ml) was heated and stirred for 6 hours at a temperature of 145 to 150° C. After xylene was eliminated by distillation, the residue was purified by a silica gel column chromatography using ethyl acetate and n-hexane as eluents. 59.5 g of Compound (F-3) was obtained as an oily product.

To 200 ml of an ethyl acetate solution containing 59.2 g of Compound (F-3), 12.5 g of N-chlorosuccinimide was added over 25 minutes under stirring and ice cooling. After stirring for 30 minutes under ice cooling, water was added for separation. The organic solvent layer was washed with saturated brine, and dried with magnesium sulfate anhydride. The solvent was eliminated by vacuum distillation, to obtain a crude product of Compound (F-4).

5,5-dimethyloxazolidine-2,4-dione (36.4 g) and triethylamine (39 ml) were dissolved in N,N-dimethylacetamide (170 ml). To this solution, a solution containing a whole amount of the previously synthesized crude product of Compound (F-4) in N,N-dimethylacetamide (30 ml) was added drop-wise over 10 minutes with stirring at room temperature. After elevating the temperature up to 70° C., the reaction mixture was stirred for 3 hours. Ethyl acetate and water were added for separation and extraction. The organic solvent layer was washed with 0.1 N potassium hydroxide aqueous solution, diluted hydrochloric acid, and saturated brine, and dried with magnesium sulfate anhydride. After the solvents were eliminated by vacuum distillation, crystallization of the residue from a mixed solvent of isopropanol and hexane gave 59.8 g of Coupler (122). (Melting point, 104 to 106° C.)

SYNTHETIC EXAMPLE 7

Synthesis of the Coupler (102)

In addition to the above Synthetic example 4, the Coupler (102) was synthesized according to the following route.

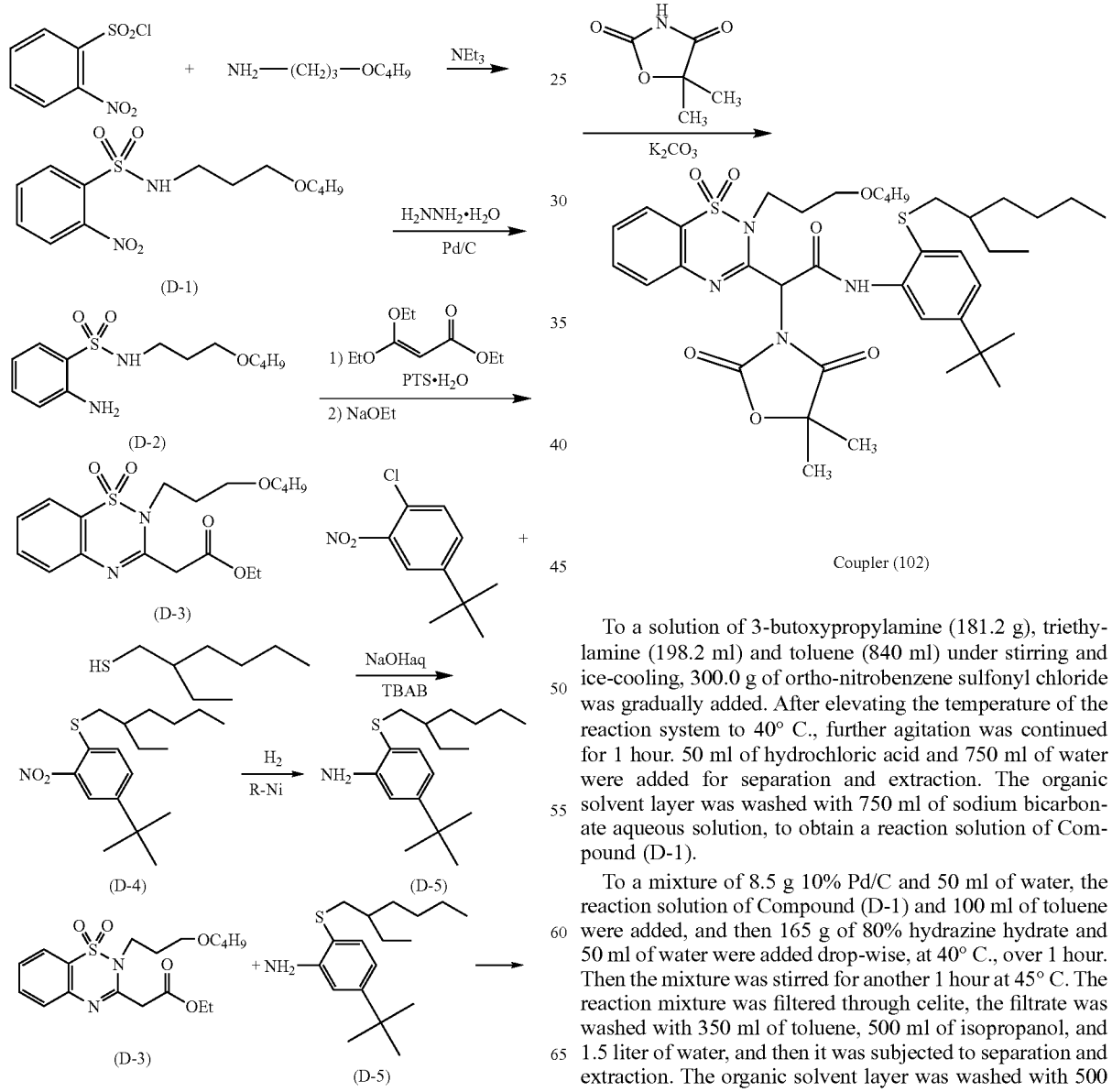

To a solution of 3-butoxypropylamine (181.2 g), triethylamine (198.2 ml) and toluene (840 ml) under stirring and ice-cooling, 300.0 g of ortho-nitrobenzene sulfonyl chloride was gradually added. After elevating the temperature of the reaction system to 40° C., further agitation was continued for 1 hour. 50 ml of hydrochloric acid and 750 ml of water were added for separation and extraction. The organic solvent layer was washed with 750 ml of sodium bicarbonate aqueous solution, to obtain a reaction solution of Compound (D-1).

To a mixture of 8.5 g 10% Pd/C and 50 ml of water, the reaction solution of Compound (D-1) and 100 ml of toluene were added, and then 165 g of 80% hydrazine hydrate and 50 ml of water were added drop-wise, at 40° C., over 1 hour. Then the mixture was stirred for another 1 hour at 45° C. The reaction mixture was filtered through celite, the filtrate was washed with 350 ml of toluene, 500 ml of isopropanol, and 1.5 liter of water, and then it was subjected to separation and extraction. The organic solvent layer was washed with 500 ml of water twice, and the reaction solution of Compound (D-2) was obtained. After the reaction solution was subjected to vacuum concentration to remove 800 ml of the solvent, 400 ml of toluene, 305.7 g of 3,3-diethoxyacrylic acid ethyl, and 2.6 g of p-toluene sulfonic acid monohydrate were added, and stirred for 30 minutes at 85° C. Further, 13.8 g of 90% sodium ethoxide was added, and the solution was heated and stirred for 4 hours at 120° C. After cooling the solution, 25 ml of hydrochloric acid and 500 ml of water were added for separation and extraction. Further, 50 g of p-toluene sulfonic acid monohydrate and 500 ml of water were added to wash the organic layer. The solvent was removed by vacuum concentration. Crystallization was conducted by adding 600 ml of methanol and 30 ml of water, and then 100 ml of methanol and 110 ml of water were added drop-wise, and the system was cooled to 0° C. Suction-filtration was conducted, and the resultant was washed with methanol-water, to obtain 440.1 g of Compound (D-3).

To a solution of 470 g of 4-t-butyl-2-nitrochlorobenzene and 14 g of tetrabutyl ammonium dissolved in 450 ml of toluene, a solution of 132 g of sodium hydroxide dissolved in 450 ml of water was added under nitrogen atmosphere. To this solution, 330 g of 2-ethylhexanethiol was added drop-wise at 70° C. over 1 hour and 30 minutes. Further, the solution was heated and stirred for 1 hour at 70° C., and then 400 ml of toluene was added for separation and extraction. The organic solvent layer was washed with water twice, to obtain a reaction solution of Compound (D-4).

In an autoclave were placed the entire amount of the reaction solution of Compound (D-4) and 10 g of Ranye Nickel, and 1500 ml of methanol, and hydrogen gas was filled therein, to pressurize. The mixture was stirred at 90° C. for 6 hours with hydrogen gas replenished. The solution was suction-filtered through celite, to remove the catalyst. To the filtrate, toluene and water were added for separation and extraction. The organic solvent layer was washed with water. The solvent was removed by vacuum distillation, to obtain 620 g of an oily product of Compound (D-5).

A mixture of 110 g of Compound (D-3), 84.5 g of Compound (D-5) and 200 ml of xylene was heated and stirred at 145 to 150° C. for 6 hours, with intermittent removal of the solvent under reduced pressure, to obtain a crude product of Compound (D-6). To the crude reaction product, 300 ml of toluene was added, and then 43.6 g of 1,3-dibromo-5,5-dimethylhydantoin was added over 15 minutes to the solution under stirring and ice cooling. After stirring for further 1 hour at room temperature, water was added to the solution for separation and extraction. The organic solvent layer was washed with water, to obtain a reaction solution of Compound (D-8).

To a mixture of 39.0 g of 5,5-dimethyloxazolidine-2,4-dione, 41.8 g of potassium carbonate and 150 ml of N,N-dimethylacetamide, under stirring at room temperature, the entire amount of the above prepared reaction solution of Compound (D-8) was added drop-wise, over 30 minutes. Thereafter, the temperature was elevated up to 50° C., and the solution was stirred for 2 hours. The organic solvent layer was separated, and the organic solvent layer was washed with 0.1 N potassium hydroxide aqueous solution, diluted hydrochloric acid, and water. The solvent was removed by vacuum distillation. Crystallization from methanol solvent gave 172.0 g of Coupler (102).

In the present invention, a silver halide color photographic light-sensitive material (hereinafter, sometimes referred to simply as "light-sensitive material") which has, on a support, at least one silver halide emulsion layer containing a yellow dye-forming coupler, at least one silver halide emulsion layer containing a magenta dye-forming coupler, and at least one silver halide emulsion layer containing a cyan dye-forming coupler, is preferably used.

In the present invention, the silver halide emulsion layer containing a yellow dye-forming coupler functions as a yellow color developing layer, the silver halide emulsion layer containing a magenta dye-forming coupler functions as a magenta color developing layer, and the silver halide emulsion layer containing a cyan dye-forming coupler functions as a cyan color developing layer. Preferably, the silver halide emulsions contained in the yellow color developing layer, the magenta color developing layer, and the cyan color developing layer may have photosensitivities to mutually different wavelength regions (for example, light in a blue region, light in a green region and light in a red region).

In addition to the yellow color developing layer, the magenta color developing layer, and the cyan color developing layer, the light-sensitive material of the present invention may have a hydrophilic colloid layer, an antihalation layer, an intermediate layer and coloring layer, as desired.

In the silver halide photographic light-sensitive material of the present invention, the yellow dye-forming coupler of the present invention is added in an amount preferably $1 \times 10^{-3}$ mole to 1 mole, and more preferably $2 \times 10^{-3}$ to $3 \times 10^{-1}$ mole, per mol of silver halide.

It is preferable that the silver halide photographic light-sensitive material of the present invention contains at least one of the above-described yellow dye-forming couplers, in at least one layer on a support.

The silver halide light-sensitive material preferably used in the present invention is explained below in detail.

The silver halide color photographic light-sensitive material preferably used in the present invention is suitable for a light-sensitive material of the type that uses a coupler. Particularly the light-sensitive material is suitable for various color light-sensitive materials, such as color negative films for general purposes or movies, color reversal films for slides or television, color papers, color positive films for general purposes or movies, light-sensitive materials for display, color reversal papers, and color proofs for scanning exposure or area exposure; and black-and-white light-sensitive materials using a coupler. Further, such color negative films are suitable for film unites with a lens, as described in JP-B-2-32615 ("JP-B" means examined Japanese patent publication) and JU-B-3-39784 ("JU-B" means examined Japanese Utility-model Registration Publication).

Among these light-sensitive materials, silver halide color photographic light-sensitive materials with which observers directly observe, such as a color reversal film for slide or television, a color paper (a color photographic paper), a color positive film for general purposes or movies, a light-sensitive material for display, a color reversal paper and color proof for scanning exposure or area exposure are preferable. Further, a color paper (a color photographic paper), a color positive film for general purposes or movies, a light-sensitive material for display, a color reversal paper and a color proof for scanning exposure or area exposure are more preferable. Particularly a color paper (a color photographic paper), a light-sensitive material for display, and a color proof for scanning exposure are most preferable.

Silver halide grains in the silver halide emulsion for use in the present invention, are preferably cubic or tetradecahedral crystal grains substantially having {100} planes (these grains may be rounded at the apexes thereof and further may have planes of higher order), or octahedral crystal grains. Alternatively, a silver halide emulsion in which the proportion of tabular grains having an aspect ratio of 2 or more and composed of {100} or {111} planes account for 50% or more in terms of the total projected area, can also be preferably used. The term "aspect ratio" refers to the value obtained by dividing the diameter of the circle having an area equivalent to the projected area of an individual grain by the thickness of the grain. In the present invention, cubic grains, or tabular grains having {100} planes as major faces, or tabular grains having {111} planes as major faces are preferably used.

As a silver halide emulsion for use in the present invention, for example, silver chloride, silver bromide, silver iodobromide, or silver chloro(iodo)bromide emulsions may be used. It is preferable for a rapid processing to use a silver chloride, silver chlorobromide, silver chloroiodide, or silver chlorobromoiodide emulsion having a silver chloride content of 90 mol % or greater, and more preferably a silver chloride, silver chlorobromide, silver chloroiodide, or silver chlorobromoiodide emulsion having a silver chloride content of 98 mol % or greater. Preferred of these silver halide emulsions are those having in the shell parts of silver halide grains a silver iodochloride phase with a silver iodide content of 0.01 to 0.50 mol %, more preferably 0.05 to 0.40 mol %, per mol of the total silver, in view of high sensitivity and excellent high illumination intensity exposure suitability. Further, especially preferred of these silver halide emulsions are those containing silver halide grains having on the surface thereof a silver bromide localized phase with a silver bromide content of 0.2 to 5 mol %, more preferably 0.5 to 3 mol %, per mol of the total silver, since both high sensitivity and stabilization of photographic properties are attained.

The silver halide emulsion for use in the present invention preferably contains silver iodide. In order to introduce iodide ions, an iodide salt solution may be added alone, or such an iodide salt solution may be added in combination with both a silver salt solution and a high chloride salt solution. In the latter case, the iodide salt solution and the high chloride salt solution may be added separately or as a mixed solution of these salts of iodide and high chloride. The iodide salt is generally added in the form of a soluble salt, such as alkali or alkali earth iodide salt. Alternatively, iodide ions may be introduced by cleaving iodide ions from an organic molecule, as described in U.S. Pat. No. 5,389,508. Further, as another source of iodide ions, fine silver iodide grains may be used.

The addition of such an iodide salt solution may be concentrated at one time of grain formation process, or it may be performed over a certain period of time. For obtaining an emulsion with high sensitivity and low fog, the position of the introduction of an iodide ion to a high silver chloride emulsion grain is restricted. The deeper in the emulsion grain the iodide ion is introduced, the smaller is the increment of sensitivity. Therefore, the addition of an iodide salt solution is preferably started at 50% or outer side of the volume of a grain, more preferably 70% or outer side, and most preferably 80% or outer side. Moreover, the addition of an iodide salt solution is preferably finished at 98% or inner side of the volume of a grain, more preferably 96% or inner side. An emulsion having higher sensitivity and lower fog can be obtained, by finishing the addition of an iodide salt solution at a little inner side from the grain surface.

The distribution of an iodide ion concentration in the depth direction inside a grain can be measured according to an etching/TOF-SIMS (Time of Flight-Secondary Ion Mass Spectrometry) method by means of, for example, a TRIFT II Model TOF-SIMS apparatus (trade name, manufactured by Phi Evans Co.). A TOF-SIMS method is specifically described in Nippon Hyomen Kagakukai edited, *Hyomen Bunseki Gijutsu Sensho Niji Ion Shitsuryo Bunsekiho* (*Surface Analysis Technique Selection—Secondary Ion Mass Analytical Method*), Maruzen Co., Ltd. (1999). When an emulsion grain is analyzed by the etching/TOF-SIMS method, it is confirmed that iodide ions ooze toward the surface of the grain, even if the addition of an iodide salt solution is finished at an inner side of the grain. It is preferred that, when an emulsion for use in the present invention contains silver iodide, grains of the emulsion have the maximum concentration of iodide ions at the surface of grain, and the iodide ion concentration decreases inwardly in grain, in the analysis by etching/TOF-SIMS.

The silver halide grains of the silver halide emulsion in the light-sensitive material of the present invention preferably have a silver bromide localized phase.

When the silver halide grains for use in the present invention contain a silver bromide localized phase, the silver bromide localized phase is preferably formed by epitaxial growth of the localized phase having a silver bromide content of at least 10 mol % on the grain surface. In addition, the emulsion grains preferably have the outermost shell portion having a silver bromide content of 1 mol % or more in the vicinity of the surface of the grains.

The silver bromide content of the silver bromide localized phase is preferably in the range of 1 to 80 mol %, and most preferably in the range of 5 to 70 mol %. The silver bromide localized phase is preferably composed of silver having population of 0.1 to 30 mol %, more preferably 0.3 to 20 mol %, to the molar amount of the entire silver which constitutes silver halide grains for use in the present invention. The silver bromide localized phase is preferably doped with complex ions of a metal of the Group VIII, such as iridium ion. The amount of these compounds to be added can be varied in a wide range depending on the purposes, and it is preferably in the range of $10^{-9}$ to $10^{-2}$ mol per mol of silver halide.

In the present invention, a metal ion is preferably added in the course of grain formation and/or growth of the silver halide grains, to include the metal ion in the inside and/or on the surface of the silver halide grains. The metal ion to be used is preferably a transition metal ion. Preferable examples of the transition metal are iron, ruthenium, iridium, osmium, lead, cadmium or zinc. It is more preferable that these metal ions are used, together with ligands, in the form of a six-coordination complex of octahedron-type. When an inorganic compound is employed as a ligand, cyanide ion, halide ion, thiocyanato, hydroxide ion, peroxide ion, azide ion, nitrite ion, water, ammonia, nitrosyl ion, or thionitrosyl ion is preferably used. Such a ligand is preferably coordinated to any metal ion selected from a group consisting of the above-mentioned iron, ruthenium, iridium, osmium, lead, cadmium and zinc. Two or more kinds of these ligands are also preferably used in one complex molecule.

Among them, the silver halide grains of the silver halide emulsion for use in the present invention particularly preferably contain an iridium ion having at least one organic ligand, for the purpose of improving high intensity reciprocity law failure.

When an organic compound is used as a ligand, preferable examples of the organic compound include chain compounds having a main chain of 5 or less carbon atoms and/or heterocyclic compounds of 5- or 6-membered ring; and this is also applicable to the transition metals other than iridium. More preferable examples of the organic compound are those having a nitrogen, phosphorus, oxygen, or sulfur atom in their molecule as an atom which is capable of coordinating to a metal. Most preferred organic compounds are furan, thiophene, oxazole, isooxazole, thiazole, isothiazole, imidazole, pyrazole, triazole, furazane, pyran, pyridine, pyridazine, pyrimidine and pyrazine. Further, organic compounds which have a substituent introduced into a basic skeleton of the above-mentioned compounds are also preferred.

Among these compounds, 5-methylthiazole among thiazole ligands is particularly preferably used as the ligand preferable for iridium ion.

Preferable combinations of a metal ion and a ligand are those of iron or ruthenium ion and cyanide ion. Preferred of these compounds are those in which the number of cyanide ions accounts for the majority of the coordination number intrinsic to the iron or ruthenium, the central metal. The remaining coordination site(s) are preferably occupied by thiocyan, ammonia, water, nitrosyl ion, dimethylsulfoxide, pyridine, pyrazine, or 4,4'-bipyridine. Most preferably each of 6 coordination sites of the central metal is occupied by a cyanide ion, to form a hexacyano iron complex or a hexacyano ruthenium complex. These metal complexes having cyanide ion ligands are preferably added, during grain formation, in an amount of $1\times10^{-8}$ mol to $1\times10^{-2}$ mol, most preferably $1\times10^{-6}$ mol to $5\times10^{-4}$ mol, per mol of silver.

In the case of the iridium ion, preferable ligands are fluoride, chloride, bromide and iodide ions, not only the organic ligands. Among these ligands, chloride and bromide ions are more preferably used. The following specific compounds can be used as iridium complexes, in addition to the above mentioned complexes having organic ligand(s): $[IrCl_6]^{3-}$, $[IrCl_6]^{2-}$, $[IrCl_5(H_2O)]^{2-}$, $[IrCl_5(H_2O)]^-$, $[IrCl_4(H_2O)_2]^-$, $[IrCl_4(H_2O)_2]^0$, $[IrCl_3(H_2O)_3]^0$, $[IrCl_3(H_2O)_3]^+$, $[IrBr_6]^{3-}$, $[IrBr_6]^{2-}$, $[IrBr_5(H_2O)]^{2-}$, $[IrBr_5(H_2O)]^-$, $[IrBr_4(H_2O)_2]^-$, $[IrBr_4(H_2O)_2]^0$, $[IrBr_3(H_2O)_3]^0$, and $[IrBr_3(H_2O)_3]^+$. These iridium complexes are preferably added during grain formation in an amount of $1\times10^{-10}$ mol to $1\times10^{-3}$ mol, most preferably $1\times10^{-8}$ mol to $1\times10^{-5}$ mol, per mol of silver.

In the case of employing ruthenium or osmium as a central metal, nitrosyl ion, thionitrosyl ion, water molecule and chloride ion are preferably used as ligands, singly or in combination. More preferably these ligands form a pentachloronitrosyl complex, a pentachlorothionitrosyl complex, or a pentachloroaquo complex. To form a hexachloro complex is also preferred. These complexes are preferably added during grain formation in an amount of $1\times10^{-10}$ mol to $1\times10^{-6}$ mol, more preferably $1\times10^{-9}$ mol to $1\times10^{-6}$ mol, per mol of silver.

In the present invention, the above-mentioned complexes are preferably added directly to the reaction solution at the time of silver halide grain formation, or indirectly to the grain-forming reaction solution via addition to an aqueous halide solution for forming silver halide grains or other solutions, so that they are doped to the inside of the silver halide grains. Further, these methods are preferably combined to incorporate the complex into the inside of the silver halide grains.

In the case where these complexes are doped to the inside of the silver halide grains, they are preferably uniformly distributed in the inside of the grains. Alternatively, as disclosed in JP-A-4-208936, JP-A-2-125245 and JP-A-3-188437, they are also preferably distributed only in the grain surface layer. Further, they are also preferably distributed only in the inside of the grain while the grain surface is covered with a layer free from the complex. Further, as disclosed in U.S. Pat. Nos. 5,252,451 and 5,256,530, it is also preferred that the silver halide grains are subjected to physical ripening to modify the grain surface layer, in the presence of fine grains having such complexes incorporated therein. Further, these methods may be used in combination. Two or more kinds of complexes may be incorporated in the inside of an individual silver halide grain. The halogen composition at the position (portion) where the complexes are incorporated, is not particularly limited, but they are preferably incorporated in any of a silver chloride layer, a silver chlorobromide layer, a silver bromide layer, a silver iodochloride layer and a silver iodobromide layer.

The silver halide grains contained in the silver halide emulsion for use in the present invention have an average grain size (the term "grain size" herein refers to the diameter of the circle equivalent to the projected area of the grain, and the number average thereof is taken as the average grain size) of preferably from 0.01 μm to 2 μm.

With respect to the distribution of sizes of these grains, so called monodisperse emulsion having a variation coefficient (the value obtained by dividing the standard deviation of the grain size distribution by the average grain size) of 20% or less, more preferably 15% or less, and further preferably 10% or less, is preferred. For obtaining a wide latitude, it is also preferred to blend the above-described monodisperse emulsions in the same layer or to form a multilayer structure by multilayer-coating of the monodisperse emulsions.

Various compounds or precursors thereof can be included in the silver halide emulsion for use in the present invention, to stabilize photographic performance or to prevent fogging from occurring, during manufacture, storage or photographic processing of the light-sensitive material. Specific examples of compounds useful for the above purposes are disclosed in JP-A-62-215272, pages 39 to 72, and they can be preferably used. In addition, 5-arylamino-1,2,3,4-thiatriazole compounds (the aryl residual group has at least one electron-attractive group) disclosed in EP No. 0 447 647 are also preferably used.

Further, in order to enhance storage stability of the silver halide emulsion for use in the present invention, it is also preferred in the present invention to use hydroxamic acid derivatives described in JP-A-11-109576; cyclic ketones having a double bond adjacent to a carbonyl group, both ends of said double bond being substituted with an amino group or a hydroxyl group, as described in JP-A-11-327094 (particularly compounds represented by formula (S1); the description at paragraph Nos. 0036 to 0071 of JP-A-11-327094 is incorporated herein by reference); sulfo-substituted catecols and hydroquinones described in JP-A-11-143011 (for example, 4,5-dihydroxy-1,3-benzenedisulfonic acid, 2,5-dihydroxy-1,4-benzenedisulfonic acid, 3,4-dihydroxybenzenesulfonic acid, 2,3-dihydroxybenzenesulfonic acid, 2,5-dihydroxybenzenesulfonic acid, 3,4,5-trihydroxybenzenesulfonic acid and salts of these acids); water-soluble reducing agents represented by formula (I), (II), or (III) of JP-A-11-102045.

Spectral sensitization can be carried out for the purpose of imparting spectral sensitivity in a desired light wavelength region to the light-sensitive emulsion in each layer of the light-sensitive material for use in the present invention.

Examples of spectral sensitizing dyes, which can be used in the light-sensitive material of the present invention, for spectral sensitization of blue, green and red light regions include, for example, those disclosed by F. M. Harmer, in *Heterocyclic compounds—Cyanine dyes and related compounds*, John Wiley & Sons, New York, London (1964). Specific examples of such compounds and spectral sensitization processes that are preferably used in the present invention include those described in JP-A-62-215272, from page 22, right upper column to page 38. In addition, the spectral sensitizing dyes described in JP-A-3-123340 are very preferred as red-sensitive spectral sensitizing dyes for silver halide emulsion grains having a high silver chloride content, from the viewpoint of stability, adsorption strength and temperature dependence of exposure, and the like.

The amount of these spectral sensitizing dyes to be added can be varied in a wide range depending on the occasion, and it is preferably in the range of $0.5 \times 10^{-6}$ mole to $1.0 \times 10^{-2}$ mole, more preferably in the range of $1.0 \times 10^{-6}$ mole to $5.0 \times 10^{-3}$ mole, per mole of silver halide.

The silver halide emulsions for use in the present invention are generally chemically sensitized. Chemical sensitization can be performed by utilizing a sulfur sensitization, represented by the addition of an unstable sulfur compound, noble metal sensitization represented by gold sensitization, and reduction sensitization, each singly or in combination thereof. Compounds that are preferably used for chemical sensitization include those described in JP-A-62-215272, from page 18, right lower column to page 22, right upper column. Of these, gold-sensitized silver halide emulsions are particularly preferred, since a change in photographic properties which occurs when scanning exposure with laser beams or the like is conducted, can be further reduced by gold sensitization.

In order to conduct gold sensitization to the silver halide emulsion for use in the present invention, various inorganic gold compounds, gold (I) complexes having an inorganic ligand, and gold (I) compounds having an organic ligand may be used. Inorganic gold compounds, such as chloroauric acid or salts thereof; and gold (I) complexes having an inorganic ligand, such as dithiocyanato gold compounds (e.g., potassium dithiocyanatoaurate (I)), and dithiosulfato gold compounds (e.g., trisodium dithiosulfatoaurate (I)), are preferably used.

As the gold (I) compounds having an organic ligand, the bis gold (I) mesoionic heterocycles described in JP-A-4-267249, for example, gold (I) tetrafluoroborate bis(1,4,5-trimethyl-1,2,4-triazolium-3-thiolate), the organic mercapto gold (I) complexes described in JP-A-11-218870, for example, potassium bis(1-[3-(2-sulfonatobenzamido)phenyl]-5-mercaptotetrazole potassium salt) aurate (I) pentahydrate, and the gold (I) compound with a nitrogen compound anion coordinated therewith described in JP-A-4-268550, for example, gold (I) bis(1-methylhydantoinate) sodium salt tetrahydrate may be used. Also, the gold (I) thiolate compound described in U.S. Pat. No. 3,503,749, the gold compounds described in JP-A-8-69074, JP-A-8-69075 and JP-A-9-269554, and the compounds described in U.S. Pat. No. 5,620,841, U.S. Pat. No. 5,912,112, U.S. Pat. No. 5,620,841, U.S. Pat. No. 5,939,245, and U.S. Pat. No. 5,912,111 may be used.

The amount of these compounds to be added can be varied in a wide range depending on the occasion, and it is generally in the range of $5 \times 10^{-7}$ mole to $5 \times 10^{-3}$ mole, preferably in the range of $5 \times 10^{-6}$ mole to $5 \times 10^{-4}$ mole, per mole of silver halide.

The silver halide emulsion for use in the present invention is preferably subjected to gold sensitization using a colloidal gold sulfide. A method of producing the colloidal gold sulfide is described in, for example, *Research Disclosure*, No. 37154, *Solid State Tonics*, Vol. 79, pp. 60 to 66 (1995), and *Compt. Rend. Hebt. Seances Acad. Sci. Sect. B*, Vol. 263, p. 1328 (1966). Colloidal gold sulfides of various grain sizes can be used, and even those having a grain diameter of 50 nm or less are also usable. The amount of these compounds to be added can be varied in a wide range depending on the occasion, and it is generally in the range of $5 \times 10^{-7}$ mol to $5 \times 10^{-3}$ mol, preferably in the range of $5 \times 10^{-6}$ mol to $5 \times 10^{-4}$ mol, per mol of silver halide.

In the present invention, gold sensitization may be used in combination with other sensitizing method(s), for example, sulfur sensitization, selenium sensitization, tellurium sensitization, reduction sensitization, and noble metal sensitization using a noble metal compound other than gold compounds.

The light-sensitive material of the present invention preferably contains, in their hydrophilic colloid layers, dyes (particularly oxonole dyes and cyanine dyes) capable of being discolored by processing, as described in European Patent No. 0337490 A2, pages 27 to 76, in order to prevent irradiation or halation or to enhance safelight safety (immunity) or the like. Further, dyes described in European Patent No. 0819977 are also preferably used in the present invention. Among these water-soluble dyes, some deteriorate color separation or safelight safety when used in an increased amount. Preferable examples of the dye that can be used without deteriorating color separation, include water-soluble dyes described in JP-A-5-127324, JP-A-5-127325 and JP-A-5-216185.

In the present invention, use can be made of a colored layer capable of being discolored during processing, in place of the water-soluble dye, or in combination with the water-soluble dye. The colored layer capable of being discolored by a processing, to be used, may be arranged so as to contact with a light-sensitive emulsion layer directly, or indirectly through an interlayer containing an agent for preventing color-mixing during processing, such as gelatin and hydroquinone. The colored layer is preferably provided as a lower layer (closer to the support) with respect to an emulsion layer which develops the same primary color as the color of the colored layer. It is possible to provide colored layers corresponding to respective primary colors, independently. Alternatively, any one or more layers selected from the above colored layers may be provided. In addition, it is possible to provide a colored layer subjected to coloring so as to match a plurality of primary-color regions. About the optical reflection density of the colored layer, it is preferred that, in a range of wavelengths used for exposure (a visible light region from 400 nm to 700 nm for an ordinary printer exposure, and wavelengths in accordance to wavelengths of the light source to be used in the case of scanning exposure), the optical density at a wavelength which provides the highest optical density is within the range of 0.2 to 3.0, more preferably 0.5 to 2.5, and particularly preferably 0.8 to 2.0.

The colored layer described above may be formed by a known method. For example, there are a method of incorporating a dye in a state of a dispersion of solid fine particles into a hydrophilic colloid layer, as described in JP-A-2-282244, from page 3, upper right column to page 8, and JP-A-3-7931, from page 3, upper right column to page 11, left under column; a method of mordanting an anionic dye in a cationic polymer, a method of allowing a dye to be adsorbed onto fine grains of silver halide or the like and fixed in the layer, and a method of using a colloidal silver as described in JP-A-1-239544. As to a method of dispersing fine-powder of a dye in solid state, for example, JP-A-2-308244, pages 4 to 13 describes a method of incorporating fine particles of a dye which is substantially water-insoluble at least at the pH of 6 or less, but is substantially water-soluble at least at the pH of 8 or more. The method of mordanting anionic dyes in a cationic polymer is described, for example, in JP-A-2-84637, pages 18 to 26. U.S. Pat. Nos.

2,688,601 and 3,459,563 disclose a method of preparing a colloidal silver to be used as a light absorber. Among these methods, preferred are the methods of incorporating fine particles of dye and the methods of using a colloidal silver.

When the present invention is applied to a color photographic paper, it is preferable that the material has at least one yellow color-forming silver halide emulsion layer, at least one magenta color-forming silver halide emulsion layer, and at least one cyan color-forming silver halide emulsion layer. Generally, these silver halide emulsion layers are in the order, from the support, of the yellow color-forming silver halide emulsion layer, the magenta color-forming silver halide emulsion layer and the cyan color-forming silver halide emulsion layer.

However, other layer arrangements which are different from the above, may be adopted.

In the light-sensitive material of the present invention, a yellow coupler-containing silver halide emulsion layer may be disposed at any position on a support. However, in the case where silver halide tabular grains are contained in the yellow coupler-containing layer, it is preferable that the yellow coupler-containing layer be positioned more apart from the support than at least one of a magenta coupler-containing silver halide emulsion layer and a cyan coupler-containing silver halide emulsion layer. Further, it is preferable that the yellow coupler-containing silver halide emulsion layer be positioned most apart from the support than other silver halide emulsion layers, from the viewpoint of color-development acceleration, desilvering acceleration, and reduction of residual color due to a sensitizing dye. Further, it is preferable that the cyan coupler-containing silver halide emulsion layer be disposed in the middle of other silver halide emulsion layers, from the viewpoint of reducing blix fading. It is preferable that the cyan coupler-containing silver halide emulsion layer be the lowest layer, from the viewpoint of reducing light fading. Further, each of the yellow-color-forming layer, the magenta-color-forming layer and the cyan-color-forming layer may be composed of two or three layers. It is also preferable that a color forming layer be formed by disposing a silver halide emulsion-free layer containing a coupler in adjacent to a silver halide emulsion layer, as described in, for example, JP-A-4-75055, JP-A-9-114035, JP-A-10-246940, and U.S. Pat. No. 5,576,159.

In this connection, hydrophilic colloid layers are generally provided between respective color-forming silver halide emulsion layers; and over a color-forming silver halide emulsion layer remotest from the support, on the side opposite to the support side. Besides, it is also a preferable embodiment of the present invention to provide a hydrophilic colloid layer between the support and a color-forming silver halide emulsion layer nearest to the support. These layers are preferably coated simultaneously by the method described, for example, in U.S. Pat. No. 5,393,571 (more preferably by curtain coating method).

Preferred examples of silver halide emulsions, other materials (additives and the like), and photographic constitutional layers (arrangement of the layers and the like) for use in the present invention, and processing methods for processing the light-sensitive materials and additives for processing are disclosed in JP-A-62-215272, JP-A-2-33144 and European Patent No. 0355660 A2. Particularly, those disclosed in European Patent No. 0355660 A2 are preferably used. Further, it is also preferred to use silver halide color photographic light-sensitive materials and processing methods thereof disclosed in, for example, JP-A-5-34889, JP-A-4-359249, JP-A-4-313753, JP-A-4-270344, JP-A-5-66527, JP-A-4-34548, JP-A-4-145433, JP-A-2-854, JP-A-1-158431, JP-A-2-90145, JP-A-3-194539, JP-A-2-93641 and European Patent Publication No. 0520457 A2.

In particular, as reflective supports and silver halide emulsions, as well as different kinds of metal ions to be doped in silver halide grains, storage stabilizers or antifogging agents of silver halide emulsions, methods of chemical sensitization (sensitizers), methods of spectral sensitization (spectral sensitizers), cyan, magenta, and yellow couplers and emulsifying and dispersing methods thereof, image stability-improving agents (stain inhibitors and discoloration inhibitors), dyes (coloring layers), kinds of gelatin, layer structures of light-sensitive materials, and film pH of light-sensitive materials, those described in the patent publications as shown in the following tables are particularly preferably used in the present invention.

| Element | JP-A-7-104448 | JP-A-7-77775 | JP-A-7-301895 |
|---|---|---|---|
| Reflective-type supports | Column 7, line 12 to Column 12, line 19 | Column 35, line 43 to Column 44, line 1 | Column 5, line 40 to Column 9, line 26 |
| Silver halide emulsions | Column 72, line 29 to Column 74, line 18 | Column 44, line 36 to Column 46, line 29 | Column 77, line 48 to Column 80, line 28 |
| Different metal ion species | Column 74, lines 19 to 44 | Column 46, line 30 to Column 47, line 5 | Column 80, line 29 to Column 81, line 6 |
| Storage stabilizers or antifoggants | Column 75, lines 9 to 18 | Column 47, lines 20 to 29 | Column 18, line 11 to Column 31, line 37 (Especially, mercaptoheterocyclic compounds) |
| Chemical sensitizing methods (Chemical sensitizers) | Column 74, line 45 to Column 75, line 6 | Column 47, lines 7 to 17 | Column 81, lines 9 to 17 |
| Spectrally sensitizing methods (Spectral sensitizers) | Column 75, line 19 to Column 76, line 45 | Column 47, line 30 to Column 49, line 6 | Column 81, line 21 to Column 82, line 48 |
| Cyan couplers | Column 12, line 20 to Column 39, line 49 | Column 62, line 50 to Column 63, line 16 | Column 88, line 49 to Column 89, line 16 |
| Yellow couplers | Column 87, line 40 to Column 88, line 3 | Column 63, lines 17 to 30 | Column 89, lines 17 to 30 |
| Magenta couplers | Column 88, lines 4 to 18 | Column 63, line 3 to Column 64, line 11 | Column 31, line 34 to Column 77, line 44 and column 88, lines 32 to 46 |
| Emulsifying and dispersing methods of couplers | Column 71, line 3 to Column 72, line 11 | Column 61, lines 36 to 49 | Column 87, lines 35 to 48 |
| Dye-image-preservability improving agents (antistaining agents) | Column 39, line 50 to Column 70, line 9 | Column 61, line 50 to Column 62, line 49 | Column 87, line 49 to Column 88, line 48 |
| Anti-fading agents | Column 70, line 10 to Column 71, line 2 | | |
| Dyes (coloring agents) | Column 77, line 42 to Column 78, | Column 7, line 14 to Column 19, | Column 9, line 27 to Column 18, |

-continued

| Element | JP-A-7-104448 | JP-A-7-77775 | JP-A-7-301895 |
|---|---|---|---|
| | line 41 | line 42, and Column 50, line 3 to Column 51, line 14 | line 10 |
| Kinds of gelatins | Column 78, lines 42 to 48 | Column 51, lines 15 to 20 | Column 83, lines 13 to 19 |
| Layer construction of light-sensitive materials | Column 39, lines 11 to 26 | Column 44, lines 2 to 35 | Column 31, line 38 to Column 32, line 33 |
| Film pH of light-sensitive materials | Column 72, lines 12 to 28 | | |
| Scanning exposure | Column 76, line 6 to Column 77, line 41 | Column 49, line 7 to Column 50, line 2 | Column 82, line 49 to Column 83, line 12 |
| Preservatives in developing solution | Column 88, line 19 to Column 89, line 22 | | |

As cyan, magenta and yellow couplers which can be used in the present invention, besides the above mentioned ones, those disclosed in JP-A-62-215272, page 91, right upper column, line 4 to page 121, left upper column, line 6, JP-A-2-33144, page 3, right upper column, line 14 to page 18, left upper column, bottom line, and page 30, right upper column, line 6 to page 35, right under column, line 11, European Patent No. 0355,660 (A2), page 4, lines 15 to 27, page 5, line 30 to page 28, bottom line, page 45, lines 29 to 31, page 47, line 23 to page 63, line 50, are also advantageously used.

Further, it is also preferred for the present invention to add compounds represented by formula (II) or (III) in WO 98/33760 and compounds represented by formula (D) described in JP-A-10-221825.

As the cyan dye-forming coupler (hereinafter also referred to as "cyan coupler") which can be used in the present invention, pyrrolotriazole-series couplers are preferably used, and more specifically, couplers represented by any of formulae (I) and (II) in JP-A-5-313324 and couplers represented by formula (I) in JP-A-6-347960 are preferred. Exemplified couplers described in these publications are particularly preferred. Further, phenol-series or naphthol-series cyan couplers are also preferred. For example, cyan couplers represented by formula (ADF) described in JP-A-10-333297 are preferred. As cyan couplers other than the foregoing cyan couplers, there are pyrroloazole-type cyan couplers described in European Patent Nos. 0 488 248 and 0 491 197 (A1), 2,5-diacylamino phenol couplers described in U.S. Pat. No. 5,888,716, and pyrazoloazole-type cyan couplers having an electron-withdrawing group or a group bonding via hydrogen bond at the 6-position, as described in U.S. Pat. Nos. 4,873,183 and 4,916,051, and particularly preferred are pyrazoloazole-type cyan couplers having a carbamoyl group at the 6-position, as described in JP-A-8-171185, JP-A-8-311360 and JP-A-8-339060.

In addition, the cyan dye-forming coupler for use in the present invention can also be a diphenylimidazole-series cyan coupler described in JP-A-2-33144; as well as a 3-hydroxypyridine-series cyan coupler (particularly a 2-equivalent coupler formed by allowing a 4-equivalent coupler of coupler (42) to have a chlorine split-off group, and couplers (6) and (9), enumerated as specific examples are particularly preferable) described in EP 0333185 A2; a cyclic active methylene-series cyan coupler (particularly couplers 3, 8, and 34 enumerated as specific examples are particularly preferable) described in JP-A-64-32260; a pyrrolopyrozole-type cyan coupler described in European Patent No. 0456226 A1; and a pyrroloimidazole-type cyan coupler described in European Patent No. 0484909.

Among these cyan couplers, pyrroloazole-series cyan couplers represented by formula (I) described in JP-A-11-282138 are particularly preferable. The descriptions of the paragraph Nos. 0012 to 0059 including exemplified cyan couplers (1) to (47) of the above JP-A-11-282138 can be entirely applied to the present invention, and therefore they are preferably incorporated in the present specification by reference.

The magenta dye-forming couplers (which may be referred to simply as a "magenta coupler" hereinafter) that can be used in the present invention are 5-pyrazolone-series magenta couplers and pyrazoloazole-series magenta couplers, as described in the above-mentioned patent publications in the above tables. Among these, preferred are pyrazolotriazole couplers in which a secondary or tertiary alkyl group is directly bonded to the 2-, 3- or 6-position of the pyrazolotriazole ring, as described in JP-A-61-65245; pyrazoloazole couplers having a sulfonamido group in their molecules, as described in JP-A-61-65246; pyrazoloazole couplers having an alkoxyphenylsulfonamido ballasting group, as described in JP-A-61-147254; and pyrazoloazole couplers having an alkoxy or aryloxy group at the 6-position, as described in European Patent Nos. 226,849 A and 294,785 A, in view of hue and stability of image to be formed therefrom and color-forming property of the couplers. Particularly as the magenta coupler, pyrazoloazole couplers represented by formula (M-I) described in JP-A-8-122984 are preferred. The descriptions of paragraph Nos. 0009 to 0026 of the patent publication JP-A-8-122984 are entirely applied to the present invention and therefore are incorporated in the present specification as a part thereof by reference. In addition, pyrazoloazole couplers having a steric hindrance group at both the 3- and 6-positions, as described in European Patent Nos. 854384 and 884640, can also be preferably used.

Further, the yellow dye-forming couplers of the present invention can be used singly or in combination with other yellow dye-forming coupler(s). Examples of the yellow dye-forming coupler (which may be referred to simply as a "yellow coupler" hereinafter) that can be used in combination with the yellow dye-forming coupler of the present invention, include acylacetamide-type yellow couplers in which the acyl group has a 3- to 5-membered cyclic structure, as described in European Patent No. 0447969 A1; malondianilide-type yellow couplers having a cyclic structure, as described in European Patent No. 0482552 A1; pyrrol-2 or 3-yl or indol-2 or 3-yl carbonyl acetic anilide-series couplers, as described in European Patent (laid open to public) Nos. 953870 A1, 953871 A1, 953872 A1, 953873 A1, 953874 A1 and 953875 A1; acylacetamide-type yellow couplers having a dioxane structure, as described in U.S. Pat. No. 5,118,599, in addition to the compounds described in the above-mentioned tables. Above all, acylacetamide-type yellow couplers in which the acyl group is a 1-alkyl-cyclopropane-1-carbonyl group, and malondianilide-type yellow couplers in which one anilide constitutes an indoline ring are especially preferably used.

It is preferred that couplers for use in the present invention, including the yellow dye-forming couplers of the present invention, are pregnated into a loadable latex polymer (as described, for example, in U.S. Pat. No. 4,203,716)

in the presence (or absence) of a high-boiling organic solvent, which will be explained later, or they are dissolved in the presence (or absence) of the foregoing high-boiling organic solvent with a polymer insoluble in water but soluble in an organic solvent, and then emulsified and dispersed into an aqueous hydrophilic colloid solution. Examples of the water-insoluble but organic solvent-soluble polymer which can be preferably used, include the homopolymers and co-polymers as disclosed in U.S. Pat. No. 4,857,449, from column 7 to column 15 and WO 88/00723, from page 12 to page 30. Use of methacrylate-series or acrylamide-series polymers, especially acrylamide-series polymers are more preferable in view of color-image stability and the like.

Examples of a high-boiling organic solvent that can be used in a water-in-oil dispersion method include phthalic acid esters (e.g., dibutyl phthalate, dioctyl phthalate, di-2-ethylhexyl phthalate), esters of phosphoric acid or phosphonic acid (e.g., triphenyl phosphate, tricresyl phosphate, tri-2-ethylhexyl phosphate), fatty acid esters (e.g., di-2-ethylhexyl succinate, tributyl citrate), benzoic acid esters (e.g., 2-ethylhexyl benzoate, dodecyl benzoate), amides (e.g., N,N-diethyldodecane amide, N,N-dimethylolein amide), alcohols or phenols (e.g., iso-stearyl alcohol, 2,4-di-tert-amyl phenol), anilines (e.g., N,N-dibutyl-2-butoxy-5-tert-octylaniline), chlorinated paraffins, hydrocarbons (e.g., dodecyl benzene, diisopropyl naphthalene), and carboxylic acids (e.g., 2-(2,4-di-tert-amyl phenoxy)butyrate). Further, the high-boiling organic solvent may be used in combination with, as an auxiliary solvent, an organic solvent having a boiling point of 30° C. or more and 160° C. or less, such as ethyl acetate, butyl acetate, methyl ethyl ketone, cyclohexanone, methylcellosolve acetate, or dimethylformamide. The high-boiling organic solvent is preferably used in an amount of 0 to 10 times (more preferably 0 to 4 times) that of a coupler, in terms of mass ratio.

All or a part of the auxiliary solvent may be removed from an emulsified dispersion by means of a vacuum distillation, a noodle washing, an ultrafiltration, or the like, as occasion demands, for the purpose of improving storage stability with the lapse of time in the state of an emulsified dispersion, or inhibiting fluctuation in photographic properties or improving stability with the lapse of time of the final coating composition in which the emulsified dispersion is mixed with a silver halide emulsion.

The average particle size of the oleophilic fine particle dispersion thus obtained is preferably in the range of 0.04 to 0.50 μm, more preferably in the range of 0.05 to 0.30 μm, and most preferably in the range of 0.08 to 0.20 μm. The average particle size can be determined with a measuring device such as Coulter submicron particle analyzer model N4 (trade name, manufactured by Coulter Electronics Co., Ltd.).

In the present invention, arbitrary color mixing-inhibitors can be used. Among these, those described in the following patent publications are preferred.

For example, high molecular mass redox compounds described in JP-A-5-333501; phenidone- or hydrazine-series compounds as described in, for example, WO 98/33760 and U.S. Pat. No. 4,923,787; and white couplers as described in, for example, JP-A-5-249637, JP-A-10-282615 and German Patent No. 19629142 A1, may be used. Particularly, in order to accelerate developing speed by increasing the pH of a developing solution, redox compounds described in, for example, German Patent No. 19618786 A1, European Patent Nos. 839623 A1 and 842975 A1, German Patent No. 19806846 A1 and French Patent No. 2760460 A1, are also preferably used.

In the present invention, as an ultraviolet ray absorbent, it is preferred to use a compound having a high molar extinction coefficient and a triazine skeleton. For example, those described in the following patent publications can be used. These compounds are preferably added to light-sensitive layers or/and light-nonsensitive layers. For example, use can be made of compounds described, in JP-A-46-3335, JP-A-55-152776, JP-A-5-197074, JP-A-5-232630, JP-A-5-307232, JP-A-6-211813, JP-A-8-53427, JP-A-8-234364, JP-A-8-239368, JP-A-9-31067, JP-A-10-115898, JP-A-10-147577, JP-A-10-182621, German Patent No. 19,739,797A, European Patent No. 0,711,804 A and JP-T-8-501291 ("JP-T" means searched and published International patent application), and the like.

As a binder or protective colloid for use in the light-sensitive material according to the present invention, gelatin is used advantageously, but another hydrophilic colloid can be used singly or in combination with gelatin. It is preferable for the gelatin that the content of heavy metals, such as Fe, Cu, Zn and Mn, included as impurities, be reduced to 5 ppm or below, more preferably 3 ppm or below. Further, the amount of calcium contained in the light-sensitive material is preferably 20 mg/m$^2$ or less, more preferably 10 mg/m$^2$ or less, and most preferably 5 mg/m$^2$ or less.

In the present invention, it is preferred to add an antibacterial (fungi-preventing) agent and antimold agent, as described in JP-A-63-271247, in order to destroy various kinds of molds and bacteria which propagate in hydrophilic colloid layers and deteriorate the image. Further, the pH of the film of the light-sensitive material is preferably in the range of 4.0 to 7.0, more preferably in the range of 4.0 to 6.5.

In the present invention, a surface-active agent may be added to the light-sensitive material, in view of improvement in coating-stability, prevention of static electricity from being generated, and adjustment of charge amount. As the surface-active agent, there are anionic, cationic, betaine and nonionic surfactants. Examples thereof include those described in JP-A-5-333492. As the surface-active agent for use in the present invention, a fluorine-containing surface-active agent is particularly preferred. The fluorine-containing surface-active agent may be used singly or in combination with known another surface-active agent. The fluorine-containing surfactant is preferably used in combination with known another surface-active agent. The amount of surface-active agent to be added to the light-sensitive material is not particularly limited, but generally in the range of $1 \times 10^{-5}$ to 1 g/m$^2$, preferably in the range of $1 \times 10^{-4}$ to $1 \times 10^{-1}$ g/m$^2$, and more preferably in the range of $1 \times 10^{-3}$ to $1 \times 10^{-2}$ g/m$^2$.

In the present invention, as a photographic support (base), a transmissive type support or a reflective type support can be used. As the transmissive type support, it is preferred to use a transparent film, such as a cellulose nitrate film or polyethylene terephthalate, as well as a polyester of 2,6-naphthalenedicarboxylic acid (NDCA) and ethylene glycol (EG), or a polyester of NDCA, terephthalic acid, and EG, provided thereon with an information-recording layer such as a magnetic layer. As the reflective type support, it is especially preferable to use a reflective support having a substrate laminated thereon with a plurality of polyethylene or polyester layers, and at least one of these waterproof resin layers (i.e. laminate layers) contains a white pigment such as titanium oxide.

It is preferred for the above-mentioned waterproof resin layer to contain a fluorescent brightening agent. A fluorescent brightening agent may be dispersed in a hydrophilic colloid layer of the light-sensitive material. As the fluorescent brightening agent, preferred are bezoxazole-series agents, coumarine-series agents and pyrazoline-series agents, and more preferred are bezoxazolyl naphthalene-series agents and bezoxazolyl stilbene-series agents. The amount of the fluorescent brightening agent to be used is not particularly limited, and it is preferably in the range of 1 to 100 mg/m$^2$. When the fluorescent brightening agent is mixed with the waterproof resin, a mixing ratio of the fluorescent brightening agent to the waterproof resin is preferably in the range of 0.0005 to 3 mass %, more preferably in the range of 0.001 to 0.5 mass %, based on the resin.

Further, a support prepared by coating a hydrophilic colloid layer containing a white pigment on a transmissive type support or the foregoing reflective type support, may be used as a reflective type support.

Furthermore, a reflective type support having a mirror plate reflective metal surface or a secondary diffusion reflective metal surface may be employed as the reflective type support.

A more preferable reflective support for use in the present invention is a support having a paper substrate provided with a polyolefin layer having fine holes, on the side to which silver halide emulsion layers are to be provided. The polyolefin layer may be composed of multi-layers. In this case, it is preferred that a polyolefin (e.g. polypropylene, polyethylene) layer adjacent to a gelatin layer on the silver halide emulsion layer side is free from microscopic pores, whereas a polyolefin (e.g. polypropylene, polyethylene) layer carrying microscopic pores is arranged on the side close to the paper substrate. The density of the multi or single polyolefin layer(s) arranged between the paper substrate and photographic constituting layers is preferably in the range of 0.40 to 1.0 g/ml, and more preferably in the range of 0.50 to 0.70 g/ml. Further, the thickness of the multi or single polyolefin layer(s) arranged between the paper substrate and photographic constituting layers is preferably in the range of 10 to 100 µm, and more preferably in the range of 15 to 70 µm. Further, the ratio of thickness of the polyolefin layer(s) to the paper substrate is preferably in the range of 0.05 to 0.5, and more preferably in the range 0.1 to 0.2. Further, it is also preferable to provide a polyolefin layer on the side of the foregoing paper substrate opposite to the side of the photographic constituting layers, i.e., on the back surface of the paper substrate, for enhancing rigidity (mechanical strength) of the reflective support. In this case, it is preferable that the polyolefin layer on the back surface be polyethylene or polypropylene, the surface of which is matted, with the polypropylene being more preferable. The thickness of the polyolefin layer on the back surface is preferably in the range of 5 to 50 µm, and more preferably in the range of 10 to 30 µm, and further the density thereof is preferably in the range of 0.7 to 1.1 g/ml. As to the reflective support for use in the present invention, preferable embodiments of the polyolefin layer to be provided on the paper substrate include those described in JP-A-10-333277, JP-A-10-333278, JP-A-11-52513, JP-A-11-65024, European Patent Nos. 0880065 and 0880066.

The light-sensitive material of the present invention can form an image via an exposure step in which the light-sensitive material is irradiated with light according to image information, and a development step in which the light-sensitive material irradiated with light is developed.

The light-sensitive material of the present invention can preferably be used, in addition to the printing system using a general negative printer, in a scanning exposure system using a cathode ray tube (CRT). The cathode ray tube exposure apparatus is simpler and more compact, and therefore less expensive than a laser-emitting apparatus. Further, optical axis and color (hue) can easily be adjusted. In the cathode ray tube for image exposure, use is made of various light-emitting substances that emit a light in spectral regions as required. For example, any one of red-light-emitting substances, green-light-emitting substances, blue-light-emitting substances, or a mixture of two or more of these light-emitting substances may be used. The spectral regions are not limited to the above red, green and blue, and fluorescent substances which can emit a light in a region of yellow, orange, purple or infrared can be used. Particularly, a cathode ray tube that emits a white light by mixing these light-emitting substances is often used.

When the light-sensitive material has a plurality of light-sensitive layers each having different spectral sensitivity distribution, and when a cathode ray tube has fluorescent substances emitting lights in a plurality of spectral regions, a plurality of colors may be exposed at the same time, i.e., image signals of a plurality of colors may be inputted to the cathode ray tube and emitted from the tube surface. Alternatively, an exposure method comprising inputting an image signal of each color successively, and emitting light of each color in order through a filter cutting other colors than the emitted color (i.e., area sequential exposure) may be adopted. In general, such an area sequential exposure is preferred for obtaining a high quality image because a cathode ray tube having high resolution power can be used.

The light-sensitive material of the present invention can preferably be used in the digital scanning exposure system using monochromatic high density light, such as a gas laser, a light-emitting diode, a semiconductor laser, a second harmonic generation light source (SHG) comprising a combination of nonlinear optical crystal with a semiconductor or a solid state laser using a semiconductor laser as an excitation light source. It is preferred to use a semiconductor laser, or a second harmonic generation light source (SHG) comprising a combination of nonlinear optical crystal with a solid state laser or a semiconductor laser, to make a system more compact and inexpensive. In particular, to design a compact and inexpensive apparatus having a longer duration of life and high stability, use of a semiconductor laser is preferable; and it is preferred that at least one of exposure light sources should be a semiconductor laser.

When such a scanning exposure light source is used, the maximum spectral sensitivity wavelength of the light-sensitive material of the present invention can be arbitrarily set up in accordance with the wavelength of a scanning exposure light source to be used. Since oscillation wavelength of a laser can be made half, using a SHG light source obtainable by a combination of a nonlinear optical crystal with a semiconductor laser or a solid state laser using a semiconductor as an excitation light source, blue light and green light can be obtained. Accordingly, it is possible to have the spectral sensitivity maximum of a light-sensitive material in normal three wavelength regions of blue, green and red. The exposure time in such a scanning exposure is defined as the time necessary to expose the size of the picture element (pixel) with the density of the picture element being 400 dpi, and preferred exposure time is 10$^{-4}$ sec or less and more preferably 10$^{-6}$ sec or less.

The silver halide color photographic light-sensitive material of the present invention is preferably used in combination with the exposure and development systems described in the following known materials. Example of the development system include the automatic print and development system described in JP-A-10-333253, the light-sensitive material transporting apparatus described in JP-A-2000-10206, the recording system including an image reading apparatus, described in JP-A-11-215312, the exposure systems with a color image recording method described in JP-A-11-88619 and JP-A-10-202950, the digital photo print system including a remote diagnosis method described in JP-A-10-210206, and the photo print system including an image recording apparatus, described in Japanese patent application No. 10-159187.

The preferred scanning exposure methods that can be applied to the present invention are described in detail in the publications in the tables shown above.

It is preferred to use a band stop filter, as described in U.S. Pat. No. 4,880,726, when the light-sensitive material of the present invention is subjected to exposure with a printer. Color mixing of light can be excluded and color reproducibility is remarkably improved by the above means.

In the present invention, a yellow microdot pattern may be previously formed by pre-exposure before giving an image information, to thereby perform a copy restraint, as described in European Patent Nos. 0789270 A1 and 0789480 A1.

With respect to the processing of the light-sensitive material of the present invention, processing materials and processing methods, as disclosed in JP-A-2-207250, from page 26, right under column, line 1 to page 34, right upper column, line 9, and JP-A-4-97355, from page 5, left upper column, line 17 to page 18, right under column, line 20, can be preferably applied. Further, as preservatives which can be used in the developing solution, compounds described in the patent publications shown in the above tables can be preferably used.

The present invention is preferably applied to a light-sensitive material having rapid processing suitability. In the case of conducting rapid processing, the color-developing time is preferably 60 sec or less, more preferably from 50 sec to 6 sec, and further preferably from 30 sec to 6 sec. Likewise, the blix time is preferably 60 sec or less, more preferably from 50 sec to 6 sec, and further preferably from 30 sec to 6 sec. Further, the washing or stabilizing time is preferably 150 sec or less, and more preferably from 130 sec to 6 sec.

Herein, the term "color-developing time" as used herein means a period of time required from the beginning of dipping a light-sensitive material into a color developing solution until the light-sensitive material is dipped into a blix solution in the subsequent processing step. In the case where a processing is carried out using, for example, an autoprocessor, the color developing time is the sum total of a time in which a light-sensitive material has been dipped in a color developing solution (so-called "time in the solution") and a time in which the light-sensitive material has left the solution and been conveyed in air toward a bleach-fixing bath in the step subsequent to color development (so-called "time in the air"). Likewise, the term "blix time" as used herein means a period of time required from the beginning of dipping a light-sensitive material into a blix solution until the light-sensitive material is dipped into a washing bath or a stabilizing bath in the subsequent processing step. Further, the term "washing or stabilizing time" as used herein means a period of time required from the beginning of dipping a light-sensitive material into a washing solution or a stabilizing solution until the end of the dipping toward a drying step (so-called "time in the solution").

Examples of a development method applicable to the light-sensitive material of the present invention after exposure, include a conventional wet system, such as a development method using a developing solution containing an alkali agent and a developing agent, and a development method wherein a developing agent is incorporated in the light-sensitive material, and an activator solution, e.g., a developing agent-free alkaline solution, is employed for the development, as well as a heat development system using no processing solution. In particular, the activator method is preferred over the other methods, because the processing solutions contain no developing agent, thereby it enables easy management and handling of the processing solutions and reduction in waste disposal load to make for environmental preservation.

Examples of the preferable developing agents or their precursors incorporated in the light-sensitive materials in the case of adopting the activator method, include the hydrazine-type compounds described in, for example, JP-A-8-234388, JP-A-9-152686, JP-A-9-152693, JP-A-9-211814 and JP-A-9-160193.

Further, it is also preferable to employ a processing method in which a light-sensitive material reduced in a coating amount of silver is subjected to an image amplification processing using hydrogen peroxide (intensification processing). In particular, it is preferable to apply this processing method to the activator method. Specifically, the image-forming methods utilizing an activator solution containing hydrogen peroxide, as disclosed in JP-A-8-297354 and JP-A-9-152695 can be preferably used. In the above activator method, the processing with an activator solution is generally followed by a desilvering step. However, the desilvering step can be omitted in the case of applying the image amplification processing method to photographic materials having a reduced silver amount. In this case, washing or stabilization processing can follow the processing with an activator solution, to result in simplification of the processing process. On the other hand, when a system of reading image information from light-sensitive materials by means of a scanner or the like is employed, the processing mode requiring no desilvering step can be employed, even if use is made of light-sensitive materials having a high silver amount, such as photographic materials for shooting.

As the processing materials and processing methods of the activator solution, desilvering solution (bleach/fixing solution), washing solution and stabilizing solution, which can be used in the present invention, known ones can be used. Preferably, those described in *Research Disclosure*, Item 36544, pp. 536-541 (September 1994), and JP-A-8-234388 can be used in the present invention.

In the case where the embodiment of the present invention is applied to a color reversal film, the descriptions (contents) described in JP-A-2001-142181 can be preferably applied thereto, and therefore the descriptions are incorporated herein by reference.

The dye-forming coupler of the present invention overcomes conventionally known problems, and it is high in coloring property and forms a dye that is excellent in hue and storage stability. Further the silver halide photographic light-sensitive material of the present invention uses the above dye-forming coupler, and is capable of forming images that have high density and high storage stability without causing both discoloration and fading of a white background and a dye image over a long period of time. The silver halide photographic light-sensitive material of the present invention is capable of forming images that are excellent in hue and density, and low in fog and color mixing, and that further have durability of color images for a long time, and that moreover are low in reduction of density even for long storage after coating. Further the silver halide color photographic light-sensitive material of the present invention is excellent in hue and density, and has no discoloration of color images for a long time, moreover is excellent in development processing stability.

According to the present invention, it is possible to provide, at a low cost, a silver halide color photographic light-sensitive material that is excellent in hue, density (coloring property), and that further has high storage stability without both discoloration and fading of a white background and a dye image, over a long period of time. The silver halide photographic light-sensitive material of the present invention is low in fog and less in color mixing, and moreover low in reduction of density, even for long storage after coating, and in addition it is excellent in development processing stability.

Hereinafter, the present invention will be described in more detail based on the following examples, but the present invention should not be limited thereto.

EXAMPLES

Example 1

Preparation of Sample 001

(Preparation of Blue-sensitive Layer Emulsion A)

Silver halide cubic grains having a halide composition of 98.9 mol % of silver chloride, 1 mol % of silver bromide, and 0.1 mol % of silver iodide, and having the average side length of 0.65 μm with the variation coefficient of side length of 8%, were prepared. Spectral sensitizing dyes-1 and -2 were added thereto in an amount of $2.5 \times 10^{-4}$ mole/Ag mole and $2.0 \times 10^{-4}$ mole/Ag mole, respectively.

At the step of grain formation, $K_3IrCl_5(H_2O)$, $K_4Ru(CN)_6$, $K_4Fe(CN)_6$, thiosulfonic acid compound-1, sodium thiosulfate, gold sensitizer-1, and mercapto compounds-1 and -2 were used in an optimal amount respectively.

Thus, a high-sensitive emulsion A-1 was prepared.

Similarly, cubic grains having an average side length of 0.50 μm, and the variation coefficient of the side length of 9%, were prepared.

Spectral sensitization and chemical sensitization were carried out in the same manner as the above, except for correcting the sensitization amounts so as to adjust the specific surface area (according to side length ratio 0.65/0.50=1.3 times). Thus, a low-sensitive emulsion A-2 was prepared.

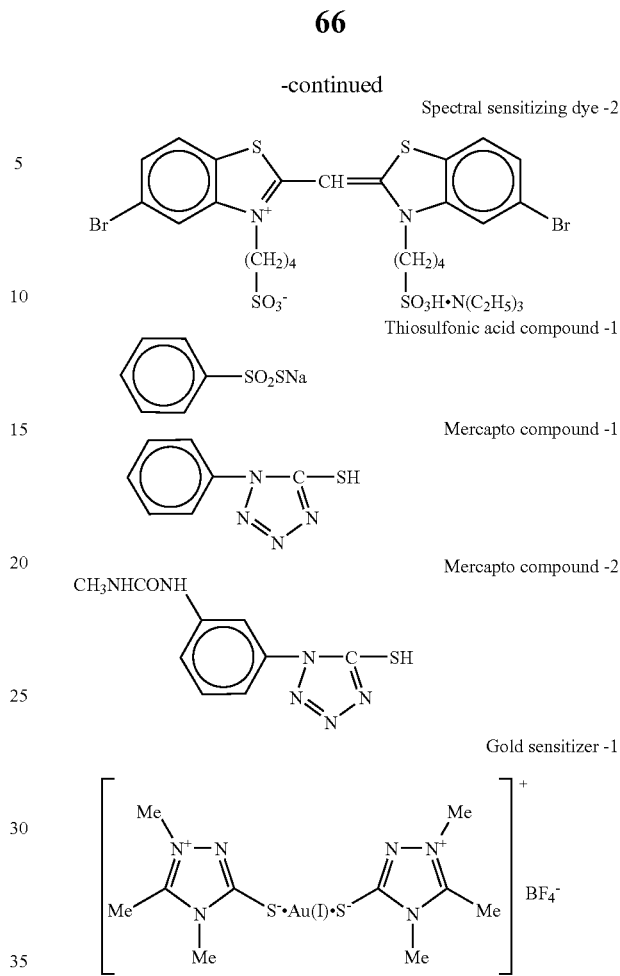

(Preparation of Green-sensitive Layer Emulsion C)

A high-sensitive green-sensitive emulsion C-1 and a low-sensitive green-sensitive emulsion C-2 were prepared in the same manner as Emulsion A-1 and Emulsion A-2 respectively, except that the temperature at the grain formation was lowered and kinds of the sensitizing dyes were changed as shown below.

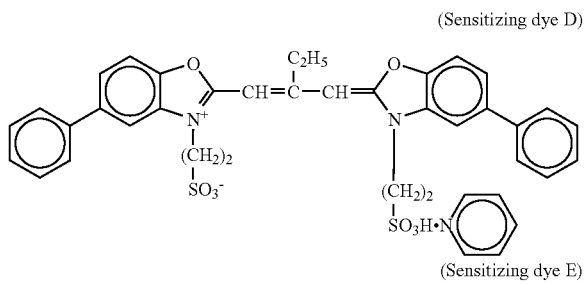

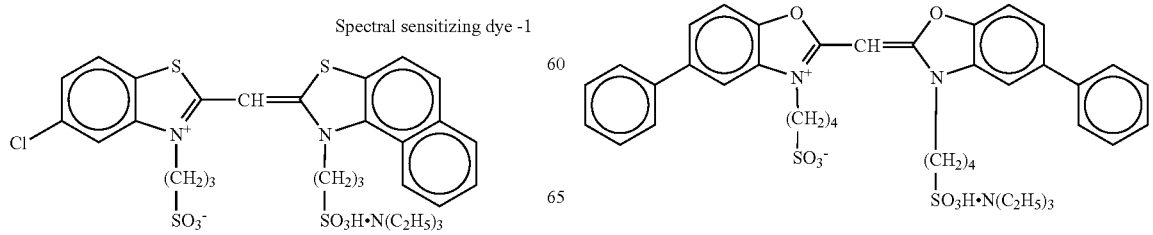

The grain size of the high-sensitive emulsion and the low-sensitive emulsion were 0.40 μm and 0.30 μm in terms of average side length respectively. The variation coefficient of the side length in the emulsions was each 8%.

Sensitizing dye D was added to the large grain size emulsion in an amount of $3.0 \times 10^{-4}$ mole, and to the small grain size emulsion in an amount of $3.6 \times 10^{-4}$ mole, per mole of silver halide respectively. Further, sensitizing dye E was added to the large grain size emulsion in an amount of $4.0 \times 10^{-5}$ mole, and to the small grain size emulsion in an amount of $7.0 \times 10^{-5}$ mole, per mole of silver halide respectively.

(Preparation of Red-sensitive Layer Emulsion E)

A high-sensitive red-sensitive emulsion E-1 and a low-sensitive red-sensitive emulsion E-2 were prepared in the same manner as Emulsion A-1 and Emulsion A-2 respectively, except that the temperature at the grain formation was lowered and kinds of the sensitizing dyes were changed as shown below.

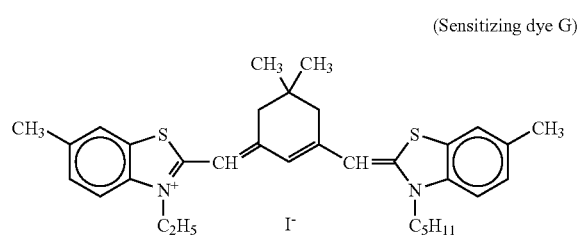
(Sensitizing dye G)

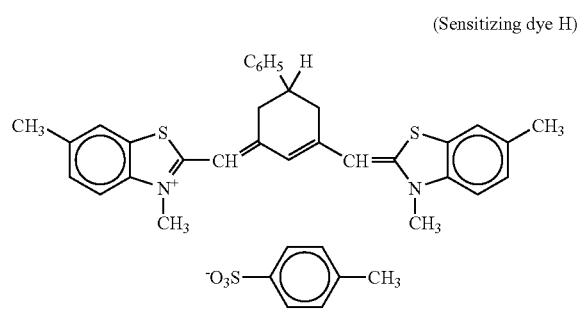
(Sensitizing dye H)

The grain size of the high-sensitive emulsion and the low-sensitive emulsion were 0.38 μm and 0.32 μm in terms of average side length, respectively. The variation coefficient of the side length in the emulsions was 9% and 10%, respectively.

Sensitizing dyes G and H were each added to the large grain size emulsion in an amount of $8.0 \times 10^{-5}$ mole, and to the small grain size emulsion in an amount of $10.7 \times 10^{-5}$ mole, per mole of silver halide respectively.

Further, the following compound I was added to the red-sensitive emulsion layer, in an amount of $3.0 \times 10^{-3}$ mole, per mole of silver halide.

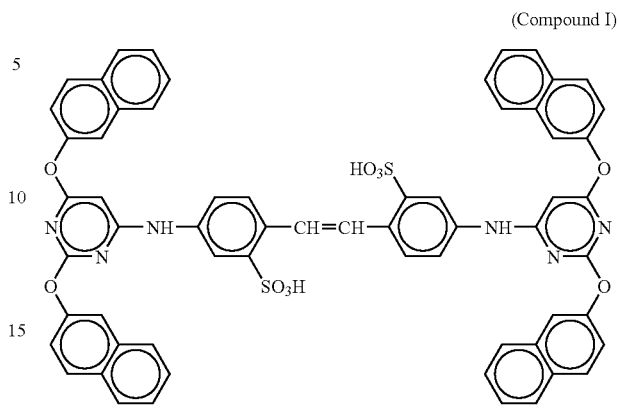
(Compound I)

Preparation of Coating Solution for First Layer 57 g of a yellow coupler (ExY), 7 g of Color-image stabilizer (Cpd-1), 4 g of Color-image stabilizer (Cpd-2), 7 g of Color-image stabilizer (Cpd-3), and 2 g of Color-image stabilizer (Cpd-8) were dissolved in 21 g of a solvent (Solv-1) and 80 ml of ethyl acetate. This solution was emulsified and dispersed with a high velocity stirring emulsifier (dissolver) in 220 g of 23.5 mass % gelatin aqueous solution containing 4 g of sodium dodecylbenzene sulfonate, and water was added thereto to obtain 900 g of Emulsified Dispersion A.

On the other hand, the above-described Emulsified Dispersion A and the above-described Emulsion A-1 and Emulsion A-2 were mixed and dissolved, to prepare a coating solution for the first layer having the composition shown below. The coating amount of the emulsion is indicated in terms of silver.

The coating solutions for the second to seventh layers were prepared in the same manner as the coating solution for the first layer. 1-Oxy-3,5-dichloro-s-triazine sodium salt (H-1), and (H-2) and (H-3) were used as gelatin hardening agents in each layer. Further, (Ab-1), (Ab-2), (Ab-3), and (Ab-4) were added to each layer such that their total amounts became 15.0 mg/m², 60.0 mg/m², 5.0 mg/m² and 10.0 mg/m², respectively.

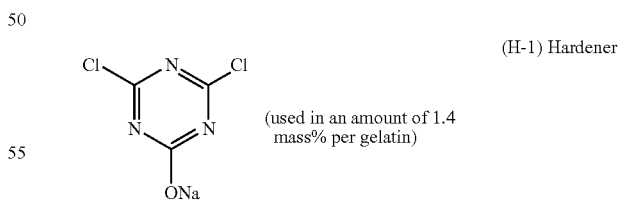
(H-1) Hardener
(used in an amount of 1.4 mass% per gelatin)

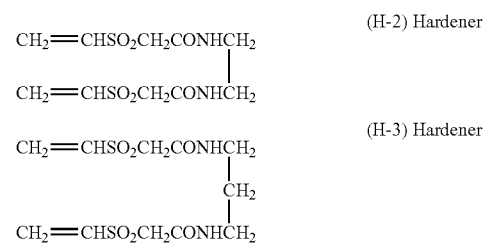
(H-2) Hardener (H-3) Hardener

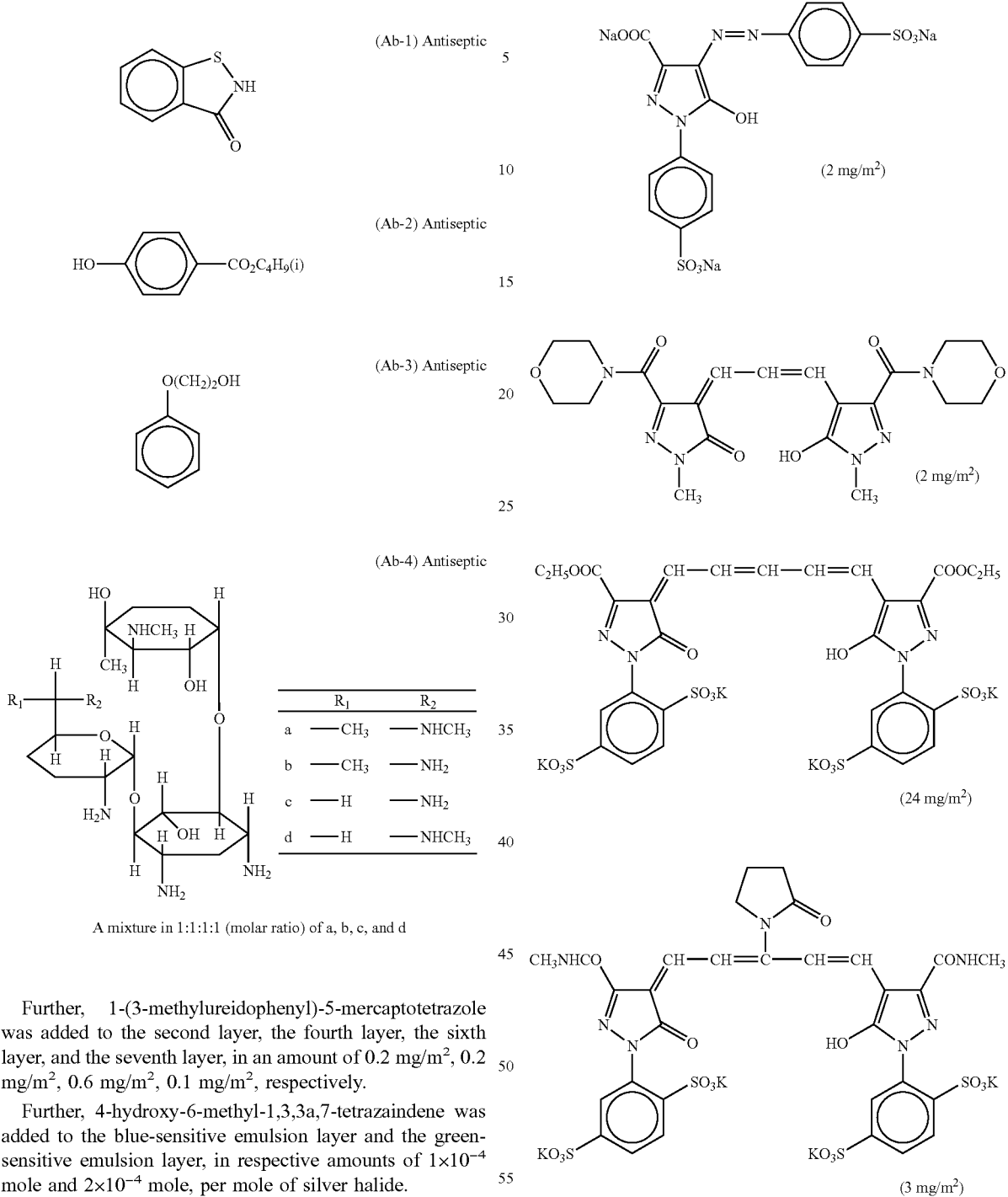

Further, 1-(3-methylureidophenyl)-5-mercaptotetrazole was added to the second layer, the fourth layer, the sixth layer, and the seventh layer, in an amount of 0.2 mg/m², 0.2 mg/m², 0.6 mg/m², 0.1 mg/m², respectively.

Further, 4-hydroxy-6-methyl-1,3,3a,7-tetrazaindene was added to the blue-sensitive emulsion layer and the green-sensitive emulsion layer, in respective amounts of $1 \times 10^{-4}$ mole and $2 \times 10^{-4}$ mole, per mole of silver halide.

Further, to the red-sensitive emulsion layer, added was a latex of a copolymer of methacrylic acid and butyl acrylate (mass ratio 1:1, average molecular mass 200,000 to 400,000) in an amount of 0.05 g/m².

Further, disodium catechol-3,5-disulfonate was added to the second layer, the fourth layer, and the sixth layer, in respective amounts of 6 mg/m², 6 mg/m², and 18 mg/m².

Further, in order to prevent irradiation, the following dyes were added. The numerals in the parentheses indicate respective coating amounts.

(Layer Constitution)

The composition of each layer is shown below. The numbers show coating amounts (g/m²). In the case of a silver halide emulsion, the coating amount is in terms of silver.

Support

Polyethylene resin laminated paper {The polyethylene resin on the first layer side contained white pigments (TiO$_2$, content of 16 mass %; ZnO, content of 4 mass %), a fluorescent whitening agent (4,4'-bis(5-methyl-benzoxazolyl)stilbene, content of 0.03 mass %) and a bluish dye (ultramarine, content of 0.33 mass %); the amount of polyethylene resin was 29.2 g/m}

| First Layer (Blue-Sensitive Emulsion Layer) | |
|---|---|
| A silver chlorobromoiodide emulsion A (gold and sulfur sensitized, cubic, a 3:7 mixture of the large-size emulsion A-1 and the small-size emulsion A-2 (in terms of mol of silver)) | 0.24 |
| Gelatin | 1.25 |
| Yellow coupler (ExY) | 0.57 |
| Color-image stabilizer (Cpd-1) | 0.07 |
| Color-image stabilizer (Cpd-2) | 0.04 |
| Color-image stabilizer (Cpd-3) | 0.07 |
| Color-image stabilizer (Cpd-8) | 0.02 |
| Solvent (Solv-1) | 0.21 |
| Second Layer (Color-Mixing Inhibiting Layer) | |
| Gelatin | 1.15 |
| Color-mixing inhibitor (Cpd-4) | 0.10 |
| Color-image stabilizer (Cpd-5) | 0.018 |
| Color-image stabilizer (Cpd-6) | 0.13 |
| Color-image stabilizer (Cpd-7) | 0.07 |
| Solvent (Solv-1) | 0.04 |
| Solvent (Solv-2) | 0.12 |
| Solvent (Solv-5) | 0.11 |
| Third Layer (Green-Sensitive Emulsion Layer) | |
| A silver chlorobromoiodide emulsion C (gold and sulfur sensitized, cubic, a 1:3 mixture of the large-size emulsion C-1 and the small-size emulsion C-2 (in terms of mol of silver)) | 0.14 |
| Gelatin | 1.21 |
| Magenta coupler (ExM) | 0.15 |
| Ultraviolet absorbing agent (UV-A) | 0.14 |
| Color-image stabilizer (Cpd-2) | 0.003 |
| Color-image stabilizer (Cpd-4) | 0.002 |
| Color-image stabilizer (Cpd-6) | 0.09 |
| Color-image stabilizer (Cpd-8) | 0.02 |
| Color-image stabilizer (Cpd-9) | 0.01 |
| Color-image stabilizer (Cpd-10) | 0.01 |
| Color-image stabilizer (Cpd-11) | 0.0001 |
| Solvent (Solv-3) | 0.09 |
| Solvent (Solv-4) | 0.18 |
| Solvent (Solv-6) | 0.07 |
| Solvent (Solv-9) | 0.10 |
| Fourth Layer (Color-Mixing Inhibiting Layer) | |
| Gelatin | 0.68 |
| Color-mixing inhibitor (Cpd-4) | 0.06 |
| Color-image stabilizer (Cpd-5) | 0.011 |
| Color-image stabilizer (Cpd-6) | 0.08 |
| Color-image stabilizer (Cpd-7) | 0.04 |
| Solvent (Solv-1) | 0.02 |
| Solvent (Solv-2) | 0.07 |
| Solvent (Solv-5) | 0.065 |
| Fifth Layer (Red-Sensitive Emulsion Layer) | |
| A silver chlorobromoiodide emulsion E (gold and sulfur sensitized, cubic, a 5:5 mixture of the large-size emulsion E-1 and the small-size emulsion E-2 (in terms of mol of silver)) | 0.16 |
| Gelatin | 0.95 |
| Cyan coupler (ExC-1) | 0.023 |
| Cyan coupler (ExC-2) | 0.05 |
| Cyan coupler (ExC-3) | 0.17 |
| Ultraviolet absorbing agent (UV-A) | 0.055 |
| Color-image stabilizer (Cpd-1) | 0.22 |
| Color-image stabilizer (Cpd-7) | 0.003 |
| Color-image stabilizer (Cpd-9) | 0.01 |
| Color-image stabilizer (Cpd-12) | 0.01 |
| Solvent (Solv-8) | 0.05 |

-continued

| Sixth Layer (Ultraviolet Absorbing Layer) | |
|---|---|
| Gelatin | 0.46 |
| Ultraviolet absorbing agent (UV-B) | 0.35 |
| Compound (S1-4) | 0.0015 |
| Solvent (Solv-7) | 0.18 |
| Seventh Layer (Protective Layer) | |
| Gelatin | 1.00 |
| Acryl-modified copolymer of polyvinyl alcohol (modification degree: 17%) | 0.4 |
| Liquid paraffin | 0.02 |
| Surface-active agent (Cpd-13) | 0.02 |

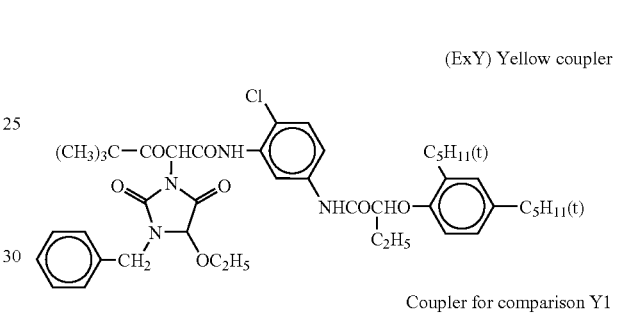

(ExY) Yellow coupler

Coupler for comparison Y1

(The same compound as the above Yellow coupler (ExY))

Coupler for comparison Y2

Coupler for comparison Y3

XV described in U.S. Patent No. 3,841,880

A mixture in 40:40:20 (molar ratio) of

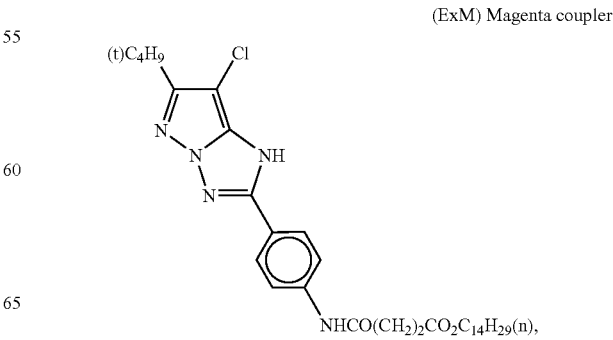

(ExM) Magenta coupler

-continued
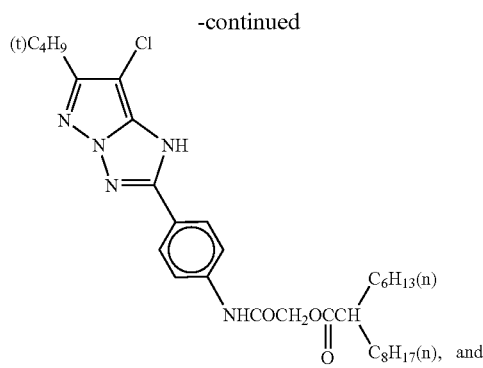
and
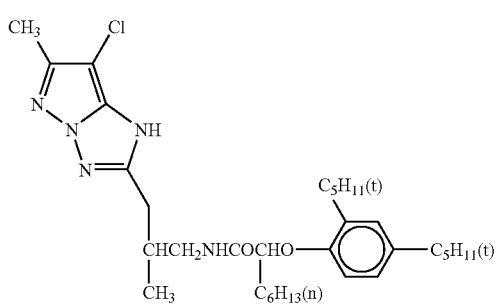
(ExC-1) Cyan coupler
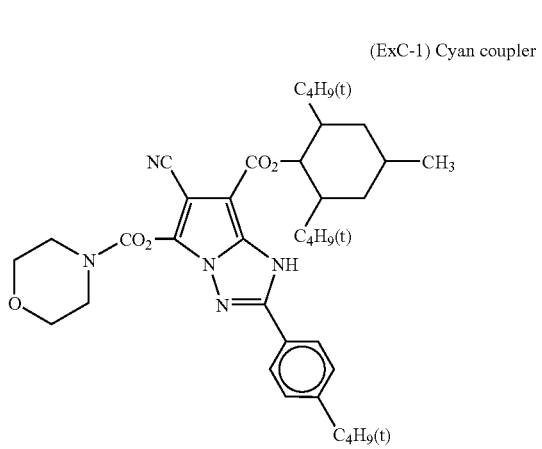
(ExC-2) Cyan coupler
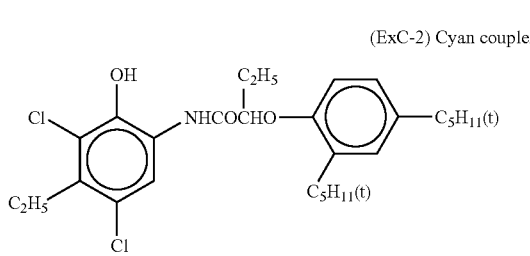
(ExC-3) Cyan coupler
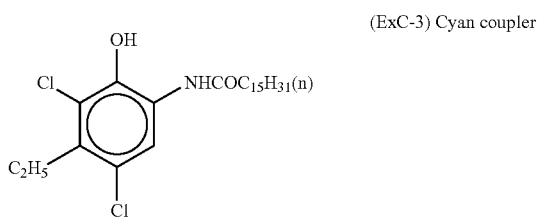
-continued
(ExC-4) Cyan coupler
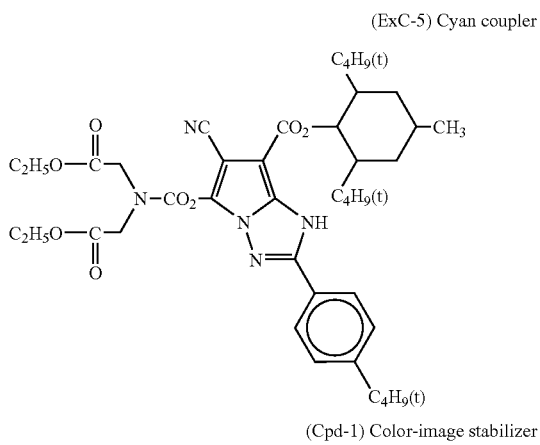
(ExC-5) Cyan coupler
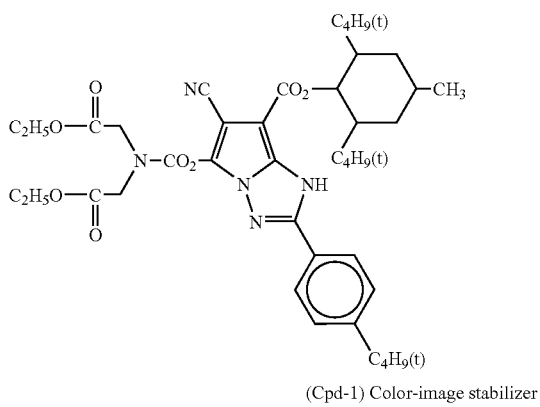
(Cpd-1) Color-image stabilizer
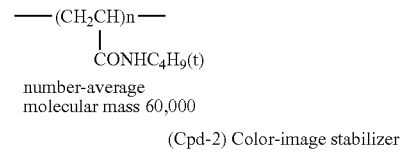
number-average molecular mass 60,000
(Cpd-2) Color-image stabilizer
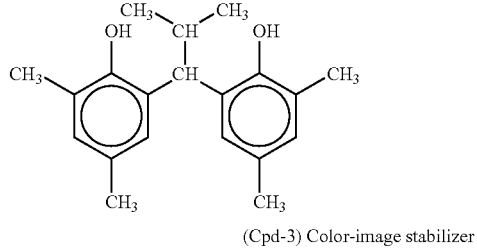
(Cpd-3) Color-image stabilizer
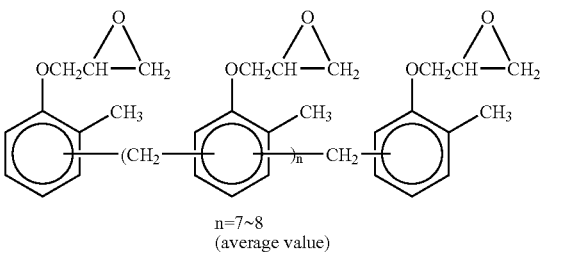
n=7~8 (average value)
(Cpd-4) Color-mixing inhibitor
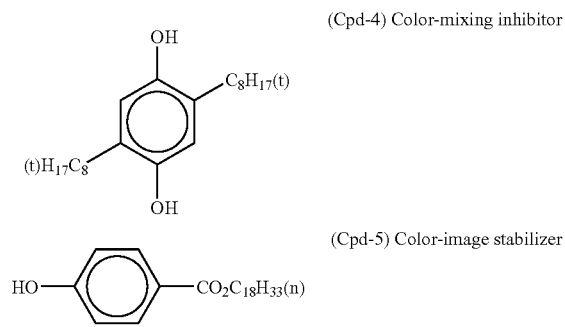
(Cpd-5) Color-image stabilizer

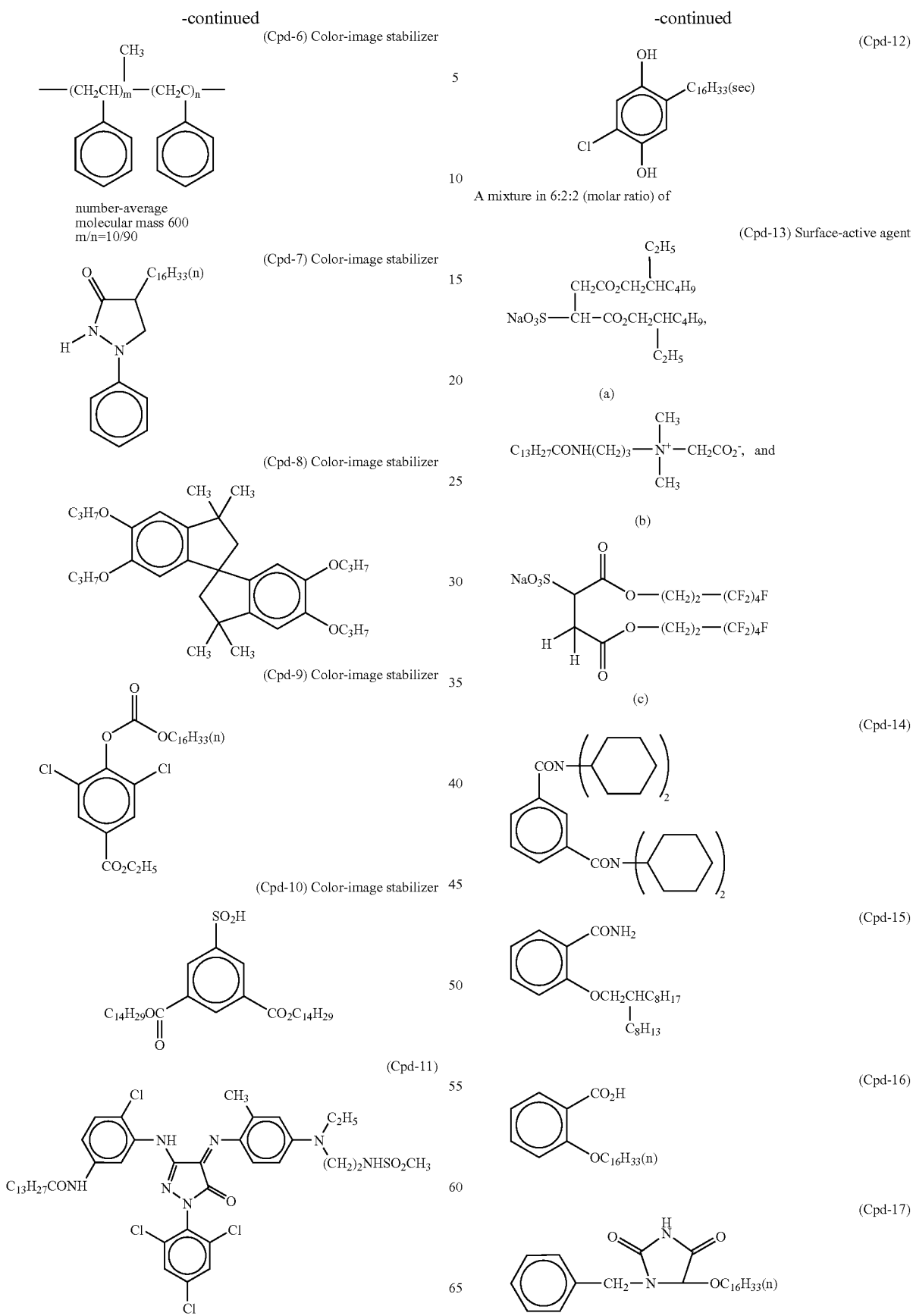

-continued
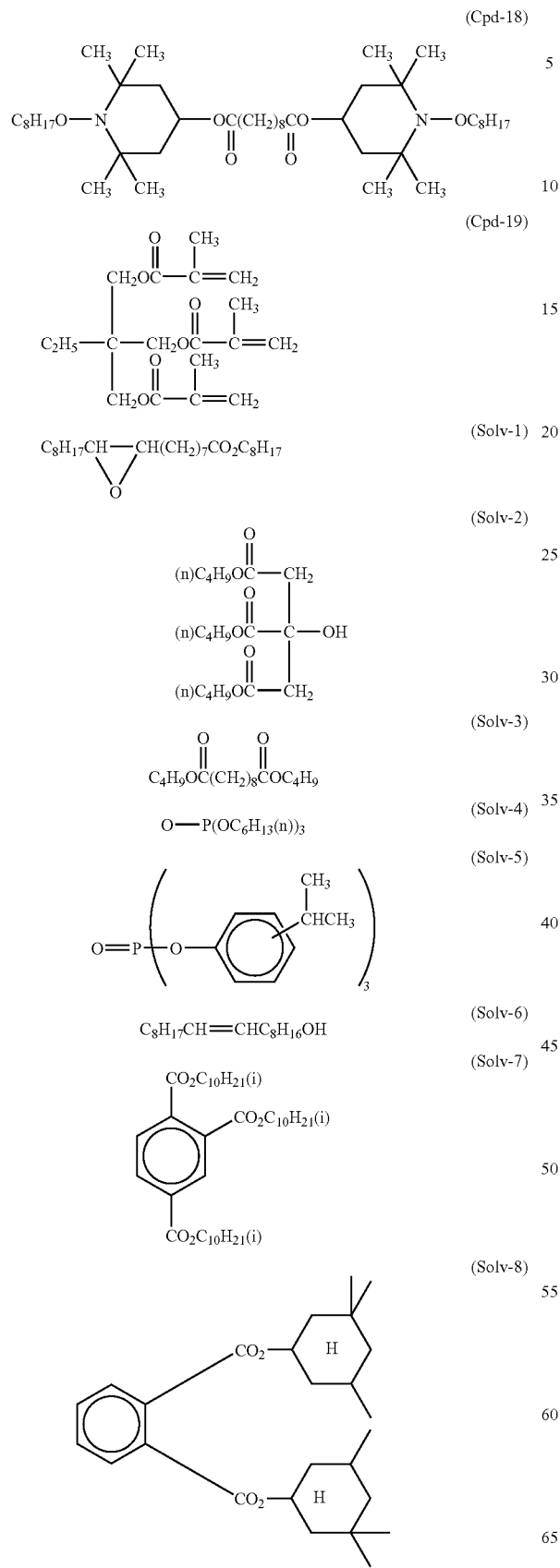
(Cpd-18)
(Cpd-19)
(Solv-1)
(Solv-2)
(Solv-3)
(Solv-4)
(Solv-5)
(Solv-6)
(Solv-7)
(Solv-8)
-continued
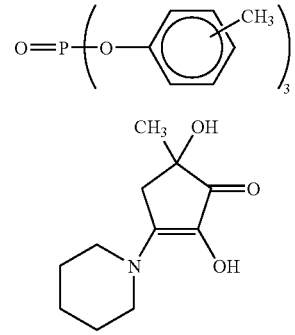
(Solv-9)
(S1-4)
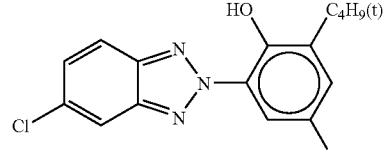
(UV-1) Ultraviolet absorbing agent
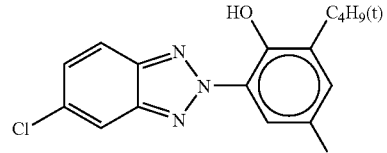
(UV-2) Ultraviolet absorbing agent
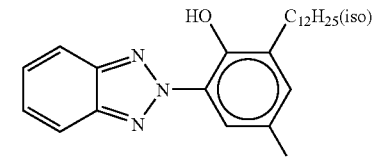
(UV-3) Ultraviolet absorbing agent
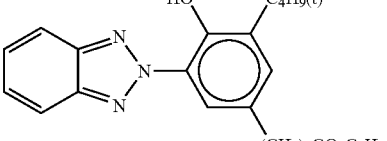
(UV-4) Ultraviolet absorbing agent
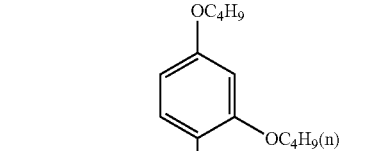
(UV-5) Ultraviolet absorbing agent
UV-A: A mixture of UV-2/UV-3 = 1/8 (mass ratio)
UV-B: A mixture of UV-1/UV-2/UV-3/UV-4 = 1/1/12/1 (mass ratio)

Preparation of Samples 101 to 115

Samples 101 to 115 were prepared in the same manner as the thus-prepared Sample 001, except that the composition of the first layer was changed as shown below.

First layer—Changes made in the constitution of the blue-sensitive emulsion layer Sample 101:

| | |
|---|---|
| A silver chlorobromoiodide emulsion A (gold and sulfur sensitized, cubic, a 3:7 mixture of the large-size emulsion A-1 and the small-size emulsion A-2 (in terms of mol of silver)) | 0.24 |
| Gelatin | 1.20 |
| Yellow coupler (Coupler for comparison Y1) | 0.53 |
| Color-image stabilizer (Cpd-2) | 0.05 |
| Color-image stabilizer (Cpd-8) | 0.05 |
| Color-image stabilizer (Cpd-19) | 0.04 |
| Color-image stabilizer (UV-3) | 0.01 |
| Solvent (Solv-4) | 0.17 |
| Solvent (Solv-9) | 0.17 |
| Solvent (Solv-6) | 0.02 |

Sample 102 was prepared in the same manner as Sample 101, except that the yellow coupler in Sample 101 was replaced by an equimolar amount of Coupler for comparison Y2. The amounts of solvents were adjusted so that the sum total of the yellow coupler, the color-image stabilizers, and the solvents would be a fixed amount. However, the composition of the three kind solvents was not changed.

Sample 103:

| | |
|---|---|
| A silver chlorobromoiodide emulsion A (gold and sulfur sensitized, cubic, a 3:7 mixture of the large-size emulsion A-1 and the small-size emulsion A-2 (in terms of mol of silver)) | 0.18 |
| Gelatin | 1.20 |
| Yellow coupler (Exemplified compound (1)) | 0.33 |
| Color-image stabilizer (Cpd-2) | 0.05 |
| Color-image stabilizer (Cpd-8) | 0.05 |
| Color-image stabilizer (Cpd-19) | 0.04 |
| Color-image stabilizer (UV-3) | 0.01 |
| Solvent (Solv-4) | 0.26 |
| Solvent (Solv-9) | 0.26 |
| Solvent (Solv-6) | 0.04 |

In the above-described sample 103, the coating amounts of the silver halide emulsion and the yellow coupler were reduced to 75% and 67% respectively to those of Sample 101; and the amounts of solvents were regulated so that the total amount of the yellow coupler, the color-image stabilizers, and the solvents would be a fixed amount.

Samples 104 to 115 were prepared in the same manner as sample 103, except that the yellow coupler in Sample 103 was replaced by an equimolar amount of a yellow coupler of the present invention. When the amount of a yellow coupler changes because of its molecular mass, the amounts of solvents were adjusted so that the sum total of the yellow coupler, the color image stabilizers and the solvents would be a fixed amount. However, in doing so, the composition of the three kind solvents was not changed.

The following two processings, which were different in the composition of processing solutions and processing time, were carried out, to evaluate the light-sensitive materials.

Processing A

Each of the aforementioned light-sensitive materials was made into a roll with a width of 127 mm; the resultant samples were exposed to light with a standard photographic image, using Digital Minilab Frontier 330 (trade name, manufactured by Fuji Photo Film Co., Ltd.); and then, the exposed samples were continuously processed (running test) in the following processing steps, respectively, until an accumulated replenisher amount of the color developing solution reached to be equal to twice the color developer tank volume.

A processing with the following running processing solutions was named processing A.

| Processing step | Temperature | Time | Replenisher amount* |
|---|---|---|---|
| Color development | 38.5° C. | 45 sec | 45 ml |
| Bleach-fixing | 38.0° C. | 45 sec | 35 ml |
| Rinse (1)** | 38.0° C. | 20 sec | — |
| Rinse (2)** | 38.0° C. | 20 sec | — |
| Rinse (3)** | 38.0° C. | 20 sec | — |
| Rinse (4)** | 38.0° C. | 20 sec | 121 ml |
| Drying | 80° C. | | |

(Note)
*Replenisher amount per $m^2$ of the light-sensitive material to be processed.
**A rinse cleaning system RC50D (trade name), manufactured by Fuji Photo Film Co., Ltd., was installed in the rinse (3), and the rinse solution was taken out from the rinse (3) and sent to a reverse osmosis membrane module (RC50D) by using a pump. The permeated water obtained in that tank was supplied to the rinse (4), and the concentrated water was returned to the rinse (3). Pump pressure was controlled such that the water to be permeated in the reverse osmosis module would be maintained in an amount of 50 to 300 ml/min, and the rinse solution was circulated under controlled temperature for 10 hours a day. The rinse was made in a four-tank counter-current system from Rinse (1) to Rinse (4).

The composition of each processing solution was as follows.

| (Color developer) | (Tank solution) | (Replenisher) |
|---|---|---|
| Water | 800 ml | 800 ml |
| Fluorescent whitening agent (FL-1) | 2.2 g | 5.1 g |
| Fluorescent whitening agent (FL-2) | 0.35 g | 1.75 g |
| Triisopropanolamine | 8.8 g | 8.8 g |
| Polyethylenegrycol (average molecular mass: 300) | 10.0 g | 10.0 g |
| Ethylenediamine tetraacetic acid | 4.0 g | 4.0 g |
| Sodium sulfite | 0.10 g | 0.20 g |
| Potassium chloride | 10.0 g | — |
| Sodium 4,5-dihydroxybenzene-1,3-disulfonate | 0.50 g | 0.50 g |
| Disodium-N,N-bis(sulfonatoethyl) hydroxylamine | 8.5 g | 14.0 g |
| 4-amino-3-methyl-N-ethyl-N-(β-methanesulfonamidoethyl) aniline · 3/2 sulfate · monohydrate | 4.8 g | 14.0 g |
| Potassium carbonate | 26.3 g | 26.3 g |
| Water to make | 1000 ml | 1000 ml |
| pH (25° C./adjusted using sulfuric acid and KOH) | 10.15 | 12.5 |

| (Bleach-fixing solution) | (Tank solution) | (Replenisher) |
|---|---|---|
| Water | 800 ml | 600 ml |
| Ammonium thiosulfate (750 g/l) | 107 ml | 214 ml |
| m-Carboxybenzenesulfinic acid | 8.3 g | 16.5 g |

-continued

| | (Tank solution) | (Replenisher) |
|---|---|---|
| Ammonium iron (III) ethylenediaminetetraacetate | 47.0 g | 94.0 g |
| Ethylenediamine tetraacetic acid | 1.4 g | 2.8 g |
| Nitric acid (67%) | 16.5 g | 33.0 g |
| Imidazole | 14.6 g | 29.2 g |
| Ammonium sulfite | 16.0 g | 32.0 g |
| Potassium metabisulfite | 23.1 g | 46.2 g |
| Water to make | 1000 ml | 1000 ml |
| pH (25° C./adjusted using nitric acid and aqua ammonia) | 6.5 | 6.5 |
| (Rinse solution) | (Tank solution) | (Replenisher) |
| Sodium chlorinated-isocyanurate | 0.02 g | 0.02 g |
| Deionized water (conductivity: 5 µS/cm or less) | 1000 ml | 1000 ml |
| PH (25° C.) | 6.5 | 6.5 |

Processing B

Each of the samples was processed into a 127-mm width roll form. They were image-wise exposed to light through a negative film having an average density, with a test processor made by remodeling a mini-lab printer processor PP350 (trade name), manufactured by Fuji Photo Film Co., Ltd., so that a processing time and temperature could be changed. A continuous processing (running test) was performed until an accumulated replenisher amount of color developer in the processing steps presented below reached two times the tank volume of color developer. The processing with the resulting running processing solution was named processing B.

| Processing step | Temperature | Time | Replenisher amount* |
|---|---|---|---|
| Color development | 45.0° C. | 17 sec | 45 ml |
| Bleach-fixing | 40.0° C. | 17 sec | 35 ml |
| Rinse (1)** | 40.0° C. | 8 sec | — |
| Rinse (2)** | 40.0° C. | 8 sec | — |
| Rinse (3)** | 40.0° C. | 8 sec | — |
| Rinse (4)** | 38.0° C. | 8 sec | 121 ml |
| Drying | 80° C. | 15 sec | |

(Note)
*Replenisher amount per $m^2$ of the light-sensitive material to be processed.
**A rinse cleaning system RC50D (trade name), manufactured by Fuji Photo Film Co., Ltd., was installed in the rinse (3), and the rinse solution was taken out from the rinse (3) and sent to a reverse osmosis membrane module (RC50D) by using a pump. The permeated water obtained in that tank was supplied to the rinse (4), and the concentrated water was returned to the rinse (3). Pump pressure was controlled such that the water to be permeated in the reverse osmosis module would be maintained in an amount of 50 to 300 ml/min, and the rinse solution was circulated under controlled temperature for 10 hours a day. The rinse was made in a four-tank counter-current system from Rinse (1) to (4).

The composition of each processing solution was as follows.

| | (Tank solution) | (Replenisher) |
|---|---|---|
| (Color developer) | | |
| Water | 800 ml | 800 ml |
| Fluorescent whitening agent (FL-3) | 4.0 g | 8.0 g |
| Residual color reducing agent (SR-1) | 3.0 g | 5.5 g |
| Triisopropanolamine | 8.8 g | 8.8 g |
| Sodium p-toluenesulfonate | 10.0 g | 10.0 g |
| Ethylenediamine tetraacetic acid | 4.0 g | 4.0 g |
| Sodium sulfite | 0.10 g | 0.10 g |
| Potassium chloride | 10.0 g | — |
| Sodium 4,5-dihydroxybenzene-1,3-disulfonate | 0.50 g | 0.50 g |
| Disodium-N,N-bis(sulfonatoethyl)hydroxylamine | 8.5 g | 14.0 g |
| 4-Amino-3-methyl-N-ethyl-N-(β-methanesulfonamidoethyl)aniline.3/2 sulfate.monohydrate | 7.0 g | 19.0 g |
| Potassium carbonate | 26.3 g | 26.3 g |
| Water to make | 1000 ml | 1000 ml |
| pH (25° C./adjusted using sulfuric acid and KOH) | 10.25 | 12.6 |
| (Bleach-fixing solution) | | |
| Water | 800 ml | 600 ml |
| Ammonium thiosulfate (750 g/l) | 107 ml | 214 ml |
| Succinic acid | 29.5 g | 59.0 g |
| Ammonium iron (III) ethylenediaminetetraacetate | 47.0 g | 94.0 g |
| Ethylenediamine tetraacetic acid | 1.4 g | 2.8 g |
| Nitric acid (67%) | 17.5 g | 35.0 g |
| Imidazole | 14.6 g | 29.2 g |
| Ammonium sulfite | 16.0 g | 32.0 g |
| Potassium metabisulfite | 23.1 g | 46.2 g |
| Water to make | 1000 ml | 1000 ml |
| pH (25° C./adjusted using nitric acid and aqua ammonia) | 6.00 | 6.00 |
| (Rinse solution) | | |
| Sodium chlorinated-isocyanurate | 0.02 g | 0.02 g |
| Deionized water (conductivity: 5 µS/cm or less) | 1000 ml | 1000 ml |
| PH (25° C.) | 6.5 | 6.5 |

-continued

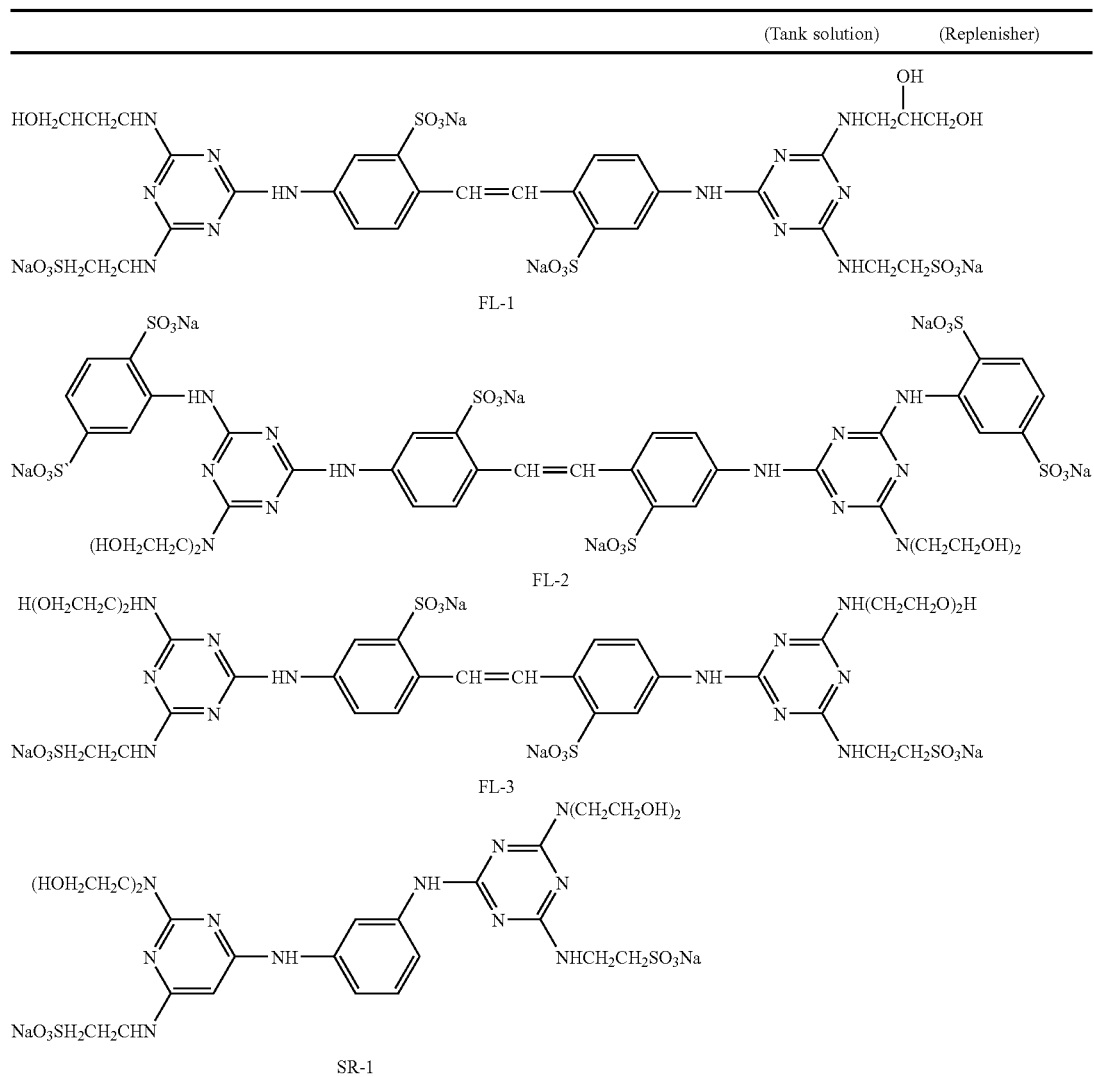

(Evaluation 1: Color Impurity)

Each sample was subjected to exposure of three-color separation, and then color development processing was performed according to the above-described processing A, to obtain monochromatic yellow-, magenta-, and cyan-colored samples respectively.

As light sources, a light source of 688 nm (R light) taken out by using a laser semiconductor, a light source of 532 nm (G light) and a light source of 473 nm (B light) each taken out by combining a semiconductor laser with SHG, respectively, were used. The quantity of R light was modulated by an external modulator, and the laser beams were scan-exposed to a sample moving in the direction vertical to the scanning direction by causing the beams be reflected on a rotating polyhedron. The scanning pitch was 400 dpi and the average exposure time per pixel was $8 \times 10^{-8}$ sec. The temperature of the semiconductor laser was kept constant by using a Peltier device to prevent the quantity of light from being changed by temperature.

A density at a yellow-colored portion of the processed sample was measured. A cyan density at the portion providing 1.6 of yellow density was measured to evaluate color impurity. Measurement was carried out using X-rite 310 (trade name, manufactured by X-rite Company) according to Status A.

(Evaluation 2: Fastness to Light)

A densitometry of the samples prepared in the foregoing Evaluation 1 was carried out before and after exposure to Xe light of 100,000 Lux for 14 days. A relative residual rate was calculated based on a density after storage at a yellow-colored portion provided an initial density of 0.5.

(Evaluation 3: Fastness to Heat and Humidity)

A densitometry of the samples prepared in the foregoing Evaluation 1 was carried out before and after storage under the conditions of 80° C. and 70% R.H. for 21 days. A relative residual rate was calculated based on a density after storage at a yellow-colored portion provided an initial density of 1.5.

(Evaluation 4: Processing Stability in Rapid Processing)

Using the exposure apparatus employed in the foregoing Evaluation 1, exposure conditions for each sample were set so that a gray gradation was obtained in the processing B. A processing was carried out with changing a conveying speed of a light-sensitive material up and down by 15% in the processing B. A fluctuation of density was measured, on an exposed portion that provided a density of 2.0 in the processing according to the standard processing time in the processing B. As a measure of evaluating the processing stability, the following value was calculated: Processing stability=(deviation of density)/(initial density of 2.0)×100.

Evaluation results are shown in Table 1.

TABLE 1

| No. | Coupler in first layer | Color im-purity | Fastness to light (%) | Fastness to heat and humidity (%) | Process-ing stability (%) | Remarks |
|---|---|---|---|---|---|---|
| 101 | Coupler for comparison Y1 | 0.140 | 40 | 70 | 86 | Comparative example |
| 102 | Coupler for comparison Y2 | 0.145 | 35 | 65 | 88 | Comparative example |
| 103 | Exemplified coupler (1) | 0.125 | 70 | 95 | 96 | This invention |
| 104 | Exemplified coupler (2) | 0.120 | 74 | 97 | 93 | This invention |
| 105 | Exemplified coupler (3) | 0.120 | 73 | 96 | 94 | This invention |
| 106 | Exemplified coupler (4) | 0.125 | 72 | 94 | 96 | This invention |
| 107 | Exemplified coupler (5) | 0.120 | 74 | 97 | 93 | This invention |
| 108 | Exemplified coupler (8) | 0.120 | 70 | 95 | 96 | This invention |
| 109 | Exemplified coupler (9) | 0.120 | 72 | 94 | 96 | This invention |
| 110 | Exemplified coupler (11) | 0.120 | 71 | 95 | 96 | This invention |
| 111 | Exemplified coupler (16) | 0.125 | 70 | 95 | 96 | This invention |
| 112 | Exemplified coupler (20) | 0.120 | 72 | 95 | 96 | This invention |
| 113 | Exemplified coupler (32) | 0.120 | 70 | 95 | 97 | This invention |
| 114 | Exemplified coupler (35) | 0.125 | 70 | 95 | 96 | This invention |
| 115 | Exemplified coupler (43) | 0.120 | 74 | 97 | 93 | This invention |

In samples 103 to 115 of the present invention, even though the amount of the respective yellow couplers was reduced to 67% by molar ratio, compared to that of sample 101, the resulting color density was equal to those samples employing the coupler for comparison. Further, it was confirmed that when a yellow coupler of the present invention was used, not only color impurity in the yellow color was reduced, but also both fastness to light and fastness to heat and humidity at a low-density portion of a yellow dye image were improved. Further, light-sensitive materials excellent in density stability at a rapid processing were obtained.

Example 2

Samples 201 to 215 were prepared in the same manner as samples 101 to 115 in Example 1, except that the arrangement of the first layer and the fifth layer was reversed. Evaluations according to Example 1 were carried out, and it was recognized that especially yellow and magenta densities of a gray image were improved compared to the samples in Example 1. Further, it was seen that light-sensitive materials that were low in color impurity and excellent in fastness to light, in fastness to heat and humidity, and in processing stability were obtained by the use of the yellow coupler of the present invention.

Example 3

Samples were prepared in the same manner as in Examples 1 and 2, except that the composition of the respective red-sensitive emulsion layers was changed as follows. Then, evaluations according to Examples 1 and 2 were carried out, and it was confirmed that samples having the constitution according to the present invention reproduced excellent rapid processing suitability, color reproduction and image fastness.

Composition for Red-Sensitive Emulsion Layer

| | |
|---|---|
| A silver chlorobromoiodide emulsion E (gold and sulfur sensitized, cubic, a 5:5 mixture of the large-size emulsion E-1 and the small-size emulsion E-2 (in terms of mol of silver)) | 0.10 |
| Gelatin | 1.11 |
| Cyan coupler (ExC-1) | 0.06 |
| Cyan coupler (ExC-3) | 0.02 |
| Cyan coupler (ExC-4) | 0.01 |
| Cyan coupler (ExC-5) | 0.06 |
| Color-image stabilizer (Cpd-1) | 0.01 |
| Color-image stabilizer (Cpd-6) | 0.05 |
| Color-image stabilizer (Cpd-7) | 0.02 |
| Color-image stabilizer (Cpd-9) | 0.04 |
| Color-image stabilizer (Cpd-10) | 0.01 |
| Color-image stabilizer (Cpd-14) | 0.01 |
| Color-image stabilizer (Cpd-15) | 0.10 |
| Color-image stabilizer (Cpd-16) | 0.01 |
| Color-image stabilizer (Cpd-17) | 0.01 |
| Color-image stabilizer (Cpd-18) | 0.07 |
| Color-image stabilizer (Cpd-19) | 0.01 |
| Ultraviolet absorbing agent (UV-7) | 0.04 |
| Solvent (Solv-5) | 0.15 |

Example 4

Samples were prepared in the same manner as in Examples 1 to 3, except that the respective silver halide emulsions were changed as set forth below, and evaluations according to Example 1 were performed. As a result, it was confirmed that silver halide color photographic light-sensitive materials excellent in color reproduction and rapid processing suitability were obtained according to the present invention.

The 1st layer: a 4:6 mixture of (Emulsion B-H) and (Emulsion B-L) (silver molar ratio)

The 3rd layer: a 5:5 mixture of (Emulsion G-H) and (Emulsion G-L) (silver molar ratio)

The 5th layer: a 6:4 mixture of (Emulsion R-H) and (Emulsion R-L) (silver molar ratio)

(Preparation of Emulsion B-H)

Using a conventional method of simultaneously adding silver nitrate and sodium chloride mixed into an aqueous gelatin solution under stirring, an emulsion of cubic high silver chloride having an equivalent-sphere diameter of 0.55 μm and a variation coefficient of 10% was prepared. In this preparation, at the step of from 80% to 90% addition of the entire silver nitrate amount, potassium bromide (3 mole % per mole of the finished silver halide) and $K_4[Ru(CN)_6]$ were added. Potassium iodide (0.3 mole % per mole of the finished silver halide) was added at the step of completion of 90% addition of the entire silver nitrate amount. Further, $K_2[Ir(5-methylthiazole)Cl_5]$ and $K_2[Ir(H_2O)Cl_5]$ were added at the step of from 92% to 98% addition of the entire silver nitrate amount. After subjecting to a desalting treatment, the resulting emulsion was added with gelatin and re-dispersed. To the emulsion, sodium thiosulfonate and the below shown Sensitizing dye A and Sensitizing dye B were added, and the resulting emulsion was optimally ripened with sodium thiosulfate pentahydrate as a sulfur sensitizer and bis(1,4,5-trimethyl-1,2,4-triazolium-3-thiolato)aurate (I).tetrafluoroborate as a gold sensitizer. Further, 1-phenyl-5-mercaptotetrazole and 1-(5-methylureidophenyl)-5-mercaptotetrazole were added. The thus-obtained emulsion was referred to as Emulsion B-H.

(Preparation of Emulsion B-L)

An emulsion of cubic high silver chloride having an equivalent-sphere diameter of 0.45 µm and a variation coefficient of 10% was prepared in the same manner as Emulsion B-H, except that addition rates of silver nitrate and sodium chloride were changed. The thus-obtained emulsion was referred to as Emulsion B-L.

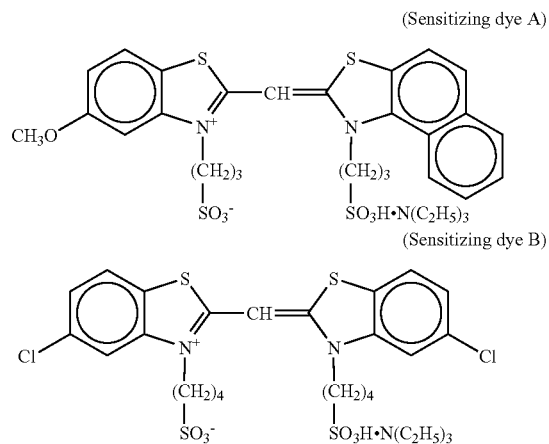

(Sensitizing dye A)

(Sensitizing dye B)

(Preparation of Emulsion G-H)

Using a conventional method of simultaneously adding silver nitrate and sodium chloride mixed into an aqueous gelatin solution under stirring, an emulsion of cubic high silver chloride having an equivalent-sphere diameter of 0.35 µm and a variation coefficient of 10% was prepared. In this preparation, at the step of from 80% to 90% addition of the entire silver nitrate amount, $K_4[Ru(CN)_6]$ was added. At the step of from 80% to 100% addition of the entire silver nitrate amount, potassium bromide (4 mole % per mole of the finished silver halide) was added. Potassium iodide (0.2 mole % per mole of the finished silver halide) was added at the step of completion of 90% addition of the entire silver nitrate amount. $K_2[Ir(5-methylthiazole)Cl_5]$ was added at the step of from 92% to 95% addition of the entire silver nitrate amount. Further, $K_2[Ir(H_2O)Cl_5]$ was added at the step of from 92% to 98% addition of the entire silver nitrate amount. The resulting emulsion was subjected to a desalting treatment, and thereafter added with gelatin and re-dispersed. To the emulsion, sodium thiosulfonate was added, and the resulting emulsion was optimally ripened with sodium thiosulfate pentahydrate as a sulfur sensitizer and bis(1,4,5-trimethyl-1,2,4-triazolium-3-thiolato)aurate (I) tetrafluoroborate as a gold sensitizer. Further, the below shown Sensitizing dye D and 1-phenyl-5-mercaptotetrazole, 1-(5-methyl ureidophenyl)-5-mercaptotetrazole and potassium bromide were added. The thus-obtained emulsion was referred to as Emulsion G-H.

(Preparation of Emulsion G-L)

An emulsion of cubic high silver chloride having an equivalent-sphere diameter of 0.28 µm and a variation coefficient of 10% was prepared in the same manner as Emulsion G-H, except that addition rates of silver nitrate and sodium chloride were changed. The thus-obtained emulsion was referred to as Emulsion G-L.

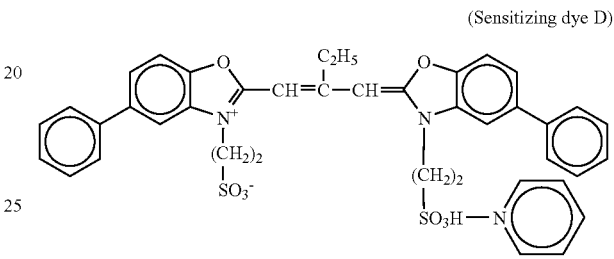

(Sensitizing dye D)

(Preparation of Emulsion R—H)

Using a conventional method of simultaneously adding silver nitrate and sodium chloride mixed into an aqueous gelatin solution under stirring, an emulsion of cubic high silver chloride having an equivalent-sphere diameter of 0.35 µm and a variation coefficient of 10% was prepared. In this preparation, at the step of from 80% to 90% addition of the entire silver nitrate amount, $K_4[Ru(CN)_6]$ was added. At the step of from 80% to 100% addition of the entire silver nitrate amount, potassium bromide (4.3 mole % per mole of the finished silver halide) was added. Potassium iodide (0.15 mole % per mole of the finished silver halide) was added at the step of completing 90% addition of the entire silver nitrate amount. Further, $K_2[Ir(5-methylthiazole)Cl_5]$ was added at the step of from 92% to 95% addition of the entire silver nitrate amount. Further, $K_2[Ir(H_2O)Cl_5]$ was added at the step of from 92% to 98% addition of the entire silver nitrate amount. The resulting emulsion was subjected to a desalting treatment, and was added with gelatin and re-dispersed. To the emulsion, sodium thiosulfonate was added, and the resulting emulsion was optimally ripened with sodium thiosulfate pentahydrate as a sulfur sensitizer and bis(1,4,5-trimethyl-1,2,4-triazolium-3-thiolato)aurate (I)-tetrafluoroborate as a gold sensitizer. Further, Sensitizing dye H shown below, 1-phenyl-5-mercaptotetrazole, 1-(5-methylureidophenyl)-5-mercaptotetrazole, Compound I shown below, and potassium bromide were added. The thus-obtained emulsion was referred to as Emulsion R-H.

(Preparation of Emulsion R-L)

An emulsion of cubic high silver chloride having an equivalent-sphere diameter of 0.28 µm and a variation coefficient of 10% was prepared in the same manner as Emulsion R-H, except that addition rates of silver nitrate and sodium chloride were changed. The thus-obtained emulsion was referred to as Emulsion R-L.

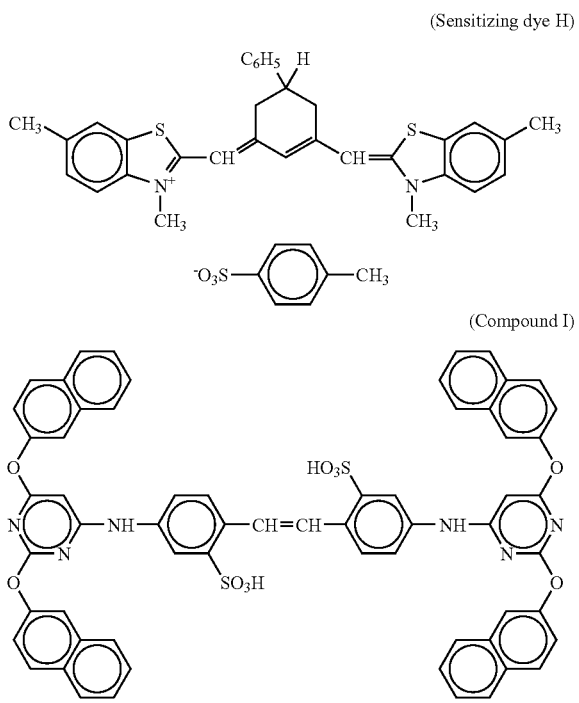

(Sensitizing dye H)

(Compound I)

Example 5

Samples prepared in Examples 1 to 4 were scan-exposed using the apparatus described below, followed by evaluation according to Examples 1 to 4. As a result, it was seen that effects of the present invention, i.e., excellent color reproduction and rapid processability, were particularly remarkably obtained by the use of samples having the composition according to the present invention.

Digital mini-lab FRONTIER 330 (trade name, manufactured by Fuji Photo Film Co., Ltd.), Lambda 130 (trade name, manufactured by Durst Company), LIGHTJET 5000 (trade name, manufactured by Gretag Company)

Example 6

Samples were prepared in the same manner as the samples in Example 1, except for changing coating amounts (sum total of coating amounts in each layer) as set forth below.

Coating amount of the blue light-sensitive silver halide emulsion layer 240%

Coating amount of the green light-sensitive silver halide emulsion layer 250%

Coating amount of the red light-sensitive silver halide emulsion layer 260%

Support: 180 μm thick transparent support of polyethyleneterephthalate

These samples were processed by Processing B as described in Example 1, except that the processing time in each process was prolonged by 2.7 times. Evaluations were carried out according to Example 1. As a result, it was seen that light-sensitive materials less in color impurity and excellent in image fastness were obtained by the use of yellow couplers of the present invention.

Example 7

Preparation of Samples 1101 to 1116

Samples 1101 to 1116 were prepared in the same manner as Sample 001 prepared in Example 1, except that the constitution of the first layer was changed as shown below.

First Layer—Changes made in the constitution of the blue-sensitive emulsion layer Sample 1101

| | |
|---|---|
| A silver chlorobromoiodide emulsion A (gold and sulfur sensitized, cubic, a 3:7 mixture of the large-size emulsion A-1 and the small-size emulsion A-2 (in terms of mol of silver)) | 0.24 |
| Gelatin | 1.20 |
| Yellow coupler (Coupler for comparison Y1) | 0.53 |
| Color-image stabilizer (Cpd-2) | 0.05 |
| Color-image stabilizer (Cpd-8) | 0.05 |
| Color-image stabilizer (Cpd-19) | 0.04 |
| Color-image stabilizer (UV-3) | 0.01 |
| Solvent (Solv-4) | 0.17 |
| Solvent (Solv-9) | 0.17 |
| Solvent (Solv-6) | 0.02 |

Sample 1102 was prepared in the same manner as Sample 1101, except that the yellow coupler in Sample 1101 was replaced by an equimolar amount of Coupler for comparison Y2. Sample 1116 was prepared in the same manner as Sample 1101, except that the yellow coupler in Sample 1101 was replaced by an equimolar amount of Coupler for comparison Y3. In this connection, when preparing these samples, the amount of the respective solvents was adjusted so that the sum total of the yellow coupler, the dye image stabilizers, and the solvents would be a fixed amount. However, the composition of the three kind solvents was not changed.

Sample 1103:

| | |
|---|---|
| A silver chlorobromoiodide emulsion A (gold and sulfur sensitized, cubic, a 3:7 mixture of the large-size emulsion A-1 and the small-size emulsion A-2 (in terms of mol of silver)) | 0.18 |
| Gelatin | 1.20 |
| Yellow coupler (101) | 0.33 |
| Color-image stabilizer (Cpd-2) | 0.05 |
| Color-image stabilizer (Cpd-8) | 0.05 |
| Color-image stabilizer (Cpd-19) | 0.04 |
| Color-image stabilizer (UV-3) | 0.01 |
| Solvent (Solv-4) | 0.26 |
| Solvent (Solv-9) | 0.26 |
| Solvent (Solv-6) | 0.04 |

In the above-described sample 1103, the coating amounts of the silver halide emulsion and the yellow coupler were reduced to 75% and 67% respectively to those of Sample 1101; and the amounts of solvents were regulated so that the total amount of the yellow coupler, the color-image stabilizers, and the solvents became a fixed amount.

Samples 1104 to 1115 were prepared in the same manner as sample 1103, except that the yellow coupler in Sample 1103 was replaced by an equimolar amount of respective yellow couplers of the present invention. When an amount (i.e. coating amount in terms of g/m$^2$) of yellow coupler changed because of its molecular mass, the amounts of solvents were adjusted so that the sum total of the yellow coupler, the color image stabilizers and the solvents became a fixed amount. However, in doing so, the composition of the three kind solvents was not changed.

Each of the light-sensitive materials thus prepared was stored in the conditions of 25° C. and 55% R.H. for 10 days and evaluated in the same manner as in Example 1.

The results are shown in Table 2.

TABLE 2

| No. | Coupler in first layer | Color impurity | Fastness to light (%) | Fastness to heat and humidity (%) | Processing stability (%) | Remarks |
|---|---|---|---|---|---|---|
| 1101 | Coupler for comparison Y1 | 0.140 | 40 | 70 | 86 | Comparative example |
| 1102 | Coupler for comparison Y2 | 0.145 | 35 | 65 | 88 | Comparative example |
| 1103 | Exemplified coupler (1) | 0.123 | 74 | 95 | 95 | This invention |
| 1104 | Exemplified coupler (2) | 0.120 | 77 | 94 | 94 | This invention |
| 1105 | Exemplified coupler (3) | 0.121 | 73 | 96 | 95 | This invention |
| 1106 | Exemplified coupler (4) | 0.124 | 76 | 94 | 96 | This invention |
| 1107 | Exemplified coupler (6) | 0.120 | 74 | 97 | 97 | This invention |
| 1108 | Exemplified coupler (8) | 0.121 | 72 | 96 | 97 | This invention |
| 1109 | Exemplified coupler (9) | 0.120 | 75 | 97 | 96 | This invention |
| 1110 | Exemplified coupler (11) | 0.122 | 72 | 94 | 97 | This invention |
| 1111 | Exemplified coupler (17) | 0.125 | 76 | 95 | 93 | This invention |
| 1112 | Exemplified coupler (21) | 0.123 | 74 | 96 | 93 | This invention |
| 1113 | Exemplified coupler (31) | 0.121 | 74 | 95 | 92 | This invention |
| 1114 | Exemplified coupler (33) | 0.124 | 76 | 93 | 92 | This invention |
| 1115 | Exemplified coupler (39) | 0.120 | 74 | 97 | 96 | This invention |
| 1116 | Coupler for comparison Y3 | 0.138 | 50 | 82 | — | Comparative example |

In samples 1103 to 1115 of the present invention, even though the amount of the respective yellow couplers was reduced to 67% by molar ratio, compared to that of samples 1101 and 1102, the resulting color density was equal to those samples employing the respective comparative couplers. Further, it was confirmed that when the yellow couplers of the present invention were used, not only color impurity in the yellow color was reduced, but also both fastness to light and fastness to heat and humidity at a low-density portion of a yellow dye image were improved. Further, light-sensitive materials excellent in density stability at a rapid processing were obtained.

Example 8

Samples 1201 to 1216 were prepared in the same manner as samples 1101 to 1116 in Example 7, except that the arrangement of the first layer and the fifth layer was reversed.

Evaluations according to Example 7 were carried out, and it was recognized that especially yellow and magenta densities of a gray image were improved compared to the samples in Example 7. Further, it was seen that light-sensitive materials that were low in color impurity and excellent in fastness to light, fastness to heat and humidity, and processing stability were obtained by the use of the yellow coupler of the present invention.

Example 9

Samples were prepared in the same manner as in Examples 7 and 8, except that the composition of the red-sensitive emulsion layer was changed with the red-sensitive emulsion layer composition prepared in Example 3. Then, evaluations according to Examples 7 and 8 were carried out, and it was also confirmed that samples having the constitution according to the present invention reproduced excellent rapid processing suitability, color reproduction and image fastness.

Example 10

Samples were prepared in the same manner as in Examples 7 to 9, except that the silver halide emulsions of the first, third, and fifth layers were changed in the same manner as in Example 4, followed by evaluation according to Example 7. As a result, it was confirmed that silver halide color photographic light-sensitive materials excellent in color reproduction and rapid processing suitability could be obtained according to the present invention.

Example 11

Samples prepared in Examples 7 to 10 were scan-exposed using the apparatus described below, followed by evaluation according to Examples 7 to 10. As a result, it was seen that effects of the present invention, i.e., excellent color reproduction and rapid processability, were particularly remarkably obtained by the use of samples having the composition according to the present invention.

Digital mini-lab FRONTIER 330 (trade name, manufactured by Fuji Photo Film Co., Ltd.), Lambda 130 (trade name, manufactured by Durst Company), LIGHTJET 5000 (trade name, manufactured by Gretag Company)

Example 12

Samples were prepared in the same manner as the samples in Example 7, except for changing coating amounts (sum total of coating amounts in each layer) as set forth below.

Coating amount of the blue light-sensitive silver halide emulsion layer 240%

Coating amount of the green light-sensitive silver halide emulsion layer 250%

Coating amount of the red light-sensitive silver halide emulsion layer 260%

Support: 180 μm thick transparent support of polyethyleneterephthalate

These samples were processed by Processing B as described in Example 1, except that the processing time in each process was prolonged by 2.7 times. Evaluations were carried out according to Example 7. As a result, it was seen that light-sensitive materials that were low in color impurity and excellent in image fastness were obtained by the use of yellow couplers of the present invention.

Example 13

Sample 1701 having the following layer constitution was prepared by applying the layers on the support used in Example 7.

In this connection, as gelatin hardeners, antiseptics, antifoggants, stabilizers, polymer latexes, and irradiation dyes in the second to seventh layers, the respective compounds used in Example 7 were used in the same amounts and were contained in the same layers as in Example 7.

First Layer (Blue-Sensitive Emulsion Layer)

| | |
|---|---|
| Emulsion (a 5:5 mixture of Emulsion BH-1 and Emulsion BL-1 (in terms of mol of silver)) | 0.16 |
| Gelatin | 1.32 |
| Exemplified coupler (1) | 0.34 |
| Color-image stabilizer (Cpd-1) | 0.01 |
| Color-image stabilizer (Cpd-2) | 0.01 |
| Color-image stabilizer (Cpd-8) | 0.08 |
| Color-image stabilizer (Cpd-18) | 0.01 |
| Color-image stabilizer (Cpd-19) | 0.02 |
| Color-image stabilizer (Cpd-20) | 0.15 |
| Color-image stabilizer (Cpd-21) | 0.01 |
| Color-image stabilizer (Cpd-23) | 0.15 |
| Additive (ExC-1) | 0.001 |
| Color-image stabilizer (UV-4) | 0.01 |
| Solvent (Solv-4) | 0.23 |
| Solvent (Solv-6) | 0.04 |
| Solvent (Solv-9) | 0.23 |

Second Layer (Color-Mixing Inhibiting Layer)

| | |
|---|---|
| Gelatin | 0.78 |
| Color-mixing inhibitor (Cpd-4) | 0.05 |
| Color-mixing inhibitor (Cpd-24) | 0.01 |
| Color-image stabilizer (Cpd-5) | 0.006 |
| Color-image stabilizer (Cpd-6) | 0.05 |
| Color-image stabilizer (Cpd-7) | 0.006 |
| Color-image stabilizer (Cpd-25) | 0.006 |
| Color-image stabilizer (UV-C) | 0.06 |
| Solvent (Solv-1) | 0.06 |
| Solvent (Solv-2) | 0.06 |
| Solvent (Solv-5) | 0.07 |
| Solvent (Solv-11) | 0.07 |

Third Layer (Green-Sensitive Emulsion Layer)

| | |
|---|---|
| Emulsion (a 1:3 mixture of GH-1 and GL-1 (in terms of mol of silver)) | 0.12 |
| Gelatin | 0.95 |
| Magenta coupler (ExM) | 0.12 |
| Ultraviolet absorbing agent (UV-C) | 0.03 |
| Color-image stabilizer (Cpd-2) | 0.01 |
| Color-image stabilizer (Cpd-6) | 0.08 |
| Color-image stabilizer (Cpd-7) | 0.005 |
| Color-image stabilizer (Cpd-8) | 0.01 |
| Color-image stabilizer (Cpd-9) | 0.01 |
| Color-image stabilizer (Cpd-10) | 0.005 |
| Color-image stabilizer (Cpd-11) | 0.0001 |
| Color-image stabilizer (Cpd-20) | 0.01 |
| Solvent (Solv-3) | 0.06 |
| Solvent (Solv-4) | 0.12 |
| Solvent (Solv-6) | 0.05 |
| Solvent (Solv-9) | 0.16 |

Fourth Layer (Color-Mixing Inhibiting Layer)

| | |
|---|---|
| Gelatin | 0.65 |
| Color-mixing inhibitor (Cpd-4) | 0.04 |
| Color-mixing inhibitor (Cpd-24) | 0.01 |
| Color-image stabilizer (Cpd-5) | 0.005 |
| Color-image stabilizer (Cpd-6) | 0.04 |
| Color-image stabilizer (Cpd-7) | 0.005 |
| Color-image stabilizer (Cpd-25) | 0.005 |
| Color-image stabilizer (UV-C) | 0.05 |
| Solvent (Solv-1) | 0.05 |
| Solvent (Solv-2) | 0.05 |
| Solvent (Solv-5) | 0.06 |
| Solvent (Solv-11) | 0.06 |

Fifth Layer (Red-Sensitive Emulsion Layer)

| | |
|---|---|
| Emulsion (a 4:6 mixture of RH-1 and RL-1 (in terms of mol of silver)) | 0.10 |
| Gelatin | 1.11 |
| Cyan coupler (ExC-5) | 0.11 |
| Cyan coupler (ExC-4) | 0.01 |
| Cyan coupler (ExC-3) | 0.04 |
| Color-image stabilizer (Cpd-1) | 0.03 |
| Color-image stabilizer (Cpd-7) | 0.01 |
| Color-image stabilizer (Cpd-9) | 0.04 |
| Color-image stabilizer (Cpd-10) | 0.001 |
| Color-image stabilizer (Cpd-14) | 0.001 |
| Color-image stabilizer (Cpd-15) | 0.18 |
| Color-image stabilizer (Cpd-16) | 0.002 |
| Color-image stabilizer (Cpd-17) | 0.001 |
| Color-image stabilizer (Cpd-18) | 0.05 |
| Color-image stabilizer (Cpd-19) | 0.04 |
| Color-image stabilizer (UV-5) | 0.10 |
| Solvent (Solv-5) | 0.19 |

Sixth Layer (Ultraviolet Absorbing Layer)

| | |
|---|---|
| Gelatin | 0.34 |
| Ultraviolet absorbing agent (UV-D) | 0.24 |
| Compound (Sl-4) | 0.0015 |
| Solvent (Solv-10) | 0.11 |

Seventh Layer (Protective Layer)

| | |
|---|---|
| Gelatin | 0.82 |
| Additive (Cpd-22) | 0.03 |
| Liquid paraffin | 0.02 |
| Surface-active agent (Cpd-13) | 0.02 |

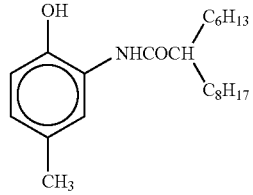

(Cpd-20)

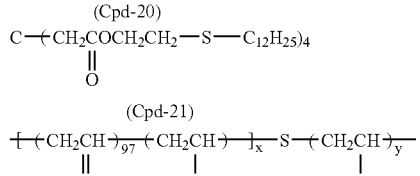

(Cpd-21)

$$\text{—}(CH_2CH)_{97}\text{—}(CH_2CH)_x\text{—}S\text{—}(CH_2CH)_y\text{—}$$
$$\quad\quad\ \ |\quad\quad\quad\ \ |\quad\quad\quad\quad\quad\ \ |$$
$$\quad\quad OH\quad\quad OCOCH_3\quad\quad\quad COOH$$

(Cpd-22)

x:y = 5:1 (mass ratio)

(Cpd-23)
KAYARAD DPCA-30 manufactured by Nippon Kayaku Co., Ltd.
(Cpd-24)
2,5-Bis(1,1-dimethyl-4-hexyloxycarbonylbutyl)hydroquinone
(Cpd-25)
Butyl p-hydroxybenzoate
(Solv-10)
Dioctyl sebacate
(Solv-11)
Diisoundecyl phthalate
(UV-C)
A 1/7/2 mixture of UV-1/UV-6/UV-5 (mass ratio)
(UV-D)
A 1/3/5/1 mixture of UV-1/UV-3/UV-6/UV-5 (mass ratio)

In the above, UV-6 is 2-(2-hydroxy-3,5-di-t-amylphenyl)benzotriazole.

Each of the above emulsions was prepared as shown below.

(Preparation of Blue-Sensitive Layer Emulsion BH-1)

Using a method of simultaneously adding silver nitrate and sodium chloride mixed into stirring deionized distilled water containing deionized gelatin, high silver chloride cubic grains were prepared. In this preparation, at the step of from 60% to 80% addition of the entire silver nitrate amount, $Cs_2[OsCl_5(NO)]$ was added. At the step of from 80% to 90% addition of the entire silver nitrate amount, potassium bromide (1.5 mole % per mole of the finished silver halide) and $K_4[Fe(CN)_6]$ were added. $K_2[IrCl_6]$ was added at the step of from 83% to 88% addition of the entire silver nitrate amount. Further, $K_2[IrCl_5(H_2O)]$ and $K[IrCl_4(H_2O)_2]$ were added at the step of from 92% to 98% addition of the entire silver nitrate amount. Potassium iodide (0.27 mole % per mole of the finished silver halide) was added, with vigorous stirring, at the step of completion of 94% addition of the entire silver nitrate amount. The thus-obtained emulsion grains were monodisperse cubic silver iodobromochloride grains having a side length of 0.54 μm and a variation coefficient of 8.5%. After being subjected to a sedimentation desalting treatment, the following were added to the resulting emulsion: gelatin, antiseptics Ab-1, Ab-2, and Ab-3, and calcium nitrate, and the emulsion was re-dispersed.

The re-dispersed emulsion was dissolved at 40° C., and Spectral sensitizing dye I, Spectral sensitizing dye J, and Spectral sensitizing dye-1 were added for optimal spectral sensitization. Then, the resulting emulsion was ripened by adding sodium benzene thiosulfate, triethylthiourea as a sulfur sensitizer and Compound-1 as a gold sensitizer for optimal chemical sensitization. Further, 1-(5-methyl ureidophenyl)-5-mercaptotetrazole; Compound-2; a mixture whose major components are compounds represented by Compound-3 in which n is 2 or 3 (both ends $X_1$ and $X_2$ are each a hydroxyl group); Compound-4, and potassium bromide were added, to finalize chemical sensitization. The thus-obtained emulsion was referred to as Emulsion BH-1.

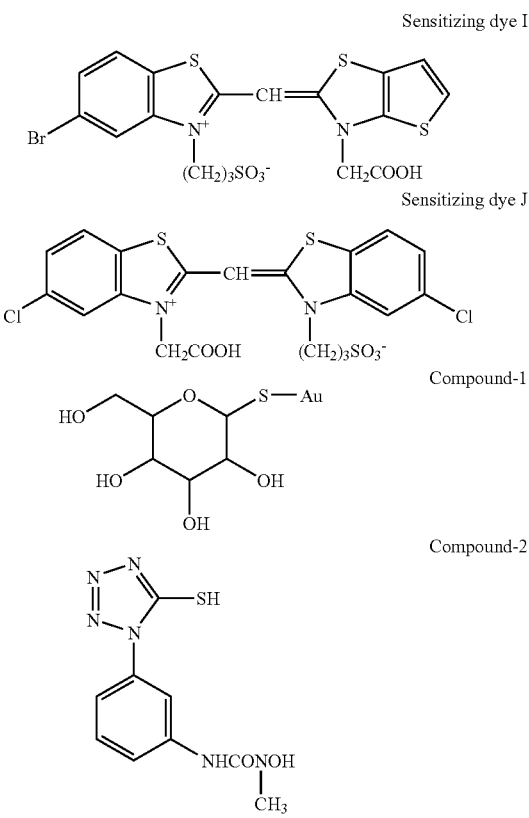

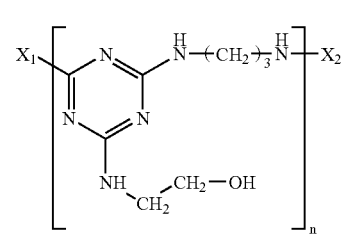

Compound-3

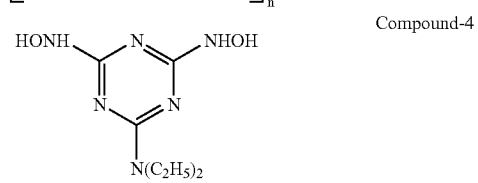

Compound-4

(Preparation of Blue-Sensitive Layer Emulsion BL-1)

Emulsion grains were prepared in the same manner as in the preparation of Emulsion BH-1, except that the temperature and the addition rate at the step of mixing silver nitrate and sodium chloride by simultaneous addition were changed, and the amounts of respective metal complexes that were to be added during the addition of silver nitrate and sodium chloride were changed. The thus-obtained emulsion grains were monodisperse cubic silver iodobromochloride grains having a side length of 0.44 μm and a variation coefficient of 9.5%. After redispersion of this emulsion, Emulsion BL-1 was prepared in the same manner as Emulsion BH-1, except that the amounts of compounds in the preparation of BH-1 were changed.

(Preparation of Green-Sensitive Layer Emulsion GH-1)

Using a method of simultaneously adding silver nitrate and sodium chloride mixed into stirring deionized distilled water containing a deionized gelatin, high chloride content cubic grains were prepared. In this preparation, at the step of from 80% to 90% addition of the entire silver nitrate amount, $K_4[Ru(CN)_6]$ was added. At the step of from 80% to 100% addition of the entire silver nitrate amount, potassium bromide (2 mole % per mole of the finished silver halide) was added. Further, $K_2[IrCl_6]$ and $K_2[RhBr_5(H_2O)]$ were added at the step of from 83% to 88% addition of the entire silver nitrate amount. Potassium iodide (0.1 mole % per mole of the finished silver halide) was added with a vigorous stirring, at the step of completion of 90% addition of the entire silver nitrate amount. $K_2[IrCl_5(H_2O)]$ and $K[IrCl_4(H_2O)_2]$ were added at the step of from 92% to 98% addition of the entire silver nitrate amount. The thus-obtained emulsion grains were monodisperse cubic silver iodobromochloride grains having a side length of 0.42 μm and a variation coefficient of 8.0%. The resulting emulsion was subjected to a sedimentation desalting treatment and re-dispersing treatment in the same manner as described in the above.

The re-dispersed emulsion was dissolved at 40° C., and sodium benzenethiosulfate, p-glutaramidophenyldisulfide, sodium thiosulfate pentahydrate as a sulfur sensitizer, and (bis(1,4,5-trimethyl-1,2,4-triazolium-3-thiolate)aurate (I).tetrafluoroborate) as a gold sensitizer were added, and the emulsion was ripened for optimal chemical sensitization. Thereafter, 1-(3-acetamidophenyl)-5-mercaptotetrazole, 1-(5-methylureidophenyl)-5-mercaptotetrazole, Compound-2, Compound-4, and potassium bromide were added. Further, in a midway of the emulsion preparation step, Spectral sensitizing dye D, Spectral sensitizing dye K, Spectral sensitizing dye L, and Spectral sensitizing dye M were added as sensitizing dyes, to conduct spectral sensitization. The thus-obtained emulsion was referred to as Emulsion GH-1.

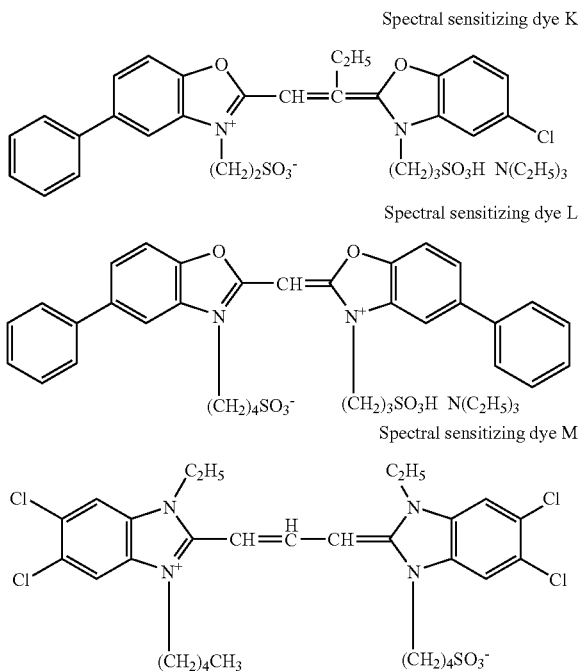

(Preparation of Green-Sensitive Layer Emulsion GL-1)

Emulsion grains were prepared in the same manner as in the preparation of Emulsion GH-1, except that the temperature and the addition rate at the step of mixing silver nitrate and sodium chloride by simultaneous addition were changed, and the amounts of respective metal complexes that were to be added during the addition of silver nitrate and sodium chloride were changed. The thus-obtained emulsion grains were monodisperse cubic silver iodobromochloride grains having a side length of 0.35 μm and a variation coefficient of 9.8%. After this emulsion was subjected to re-dispersion, Emulsion GL-1 was prepared in the same manner as Emulsion GH-1, except that the amounts of compounds in the preparation of GH-1 were changed.

(Preparation of Red-Sensitive Layer Emulsion RH-1)

Using a method of simultaneously adding silver nitrate and sodium chloride mixed into stirring deionized distilled water containing deionized gelatin, high silver chloride cubic grains were prepared. In this preparation, at the step of from 60% to 80% addition of the entire silver nitrate amount, $Cs_2[OsCl_5(NO)]$ was added. At the step of from 80% to 90% addition of the entire silver nitrate amount, $K_4[Ru(CN)_6]$ was added. At the step of from 80% to 100% addition of the entire silver nitrate amount, potassium bromide (1.3 mole % per mole of the finished silver halide) was added. Further, $K_2[IrCl_5(5\text{-methylthiazole})]$ was added at the step of from 83% to 88% addition of the entire silver nitrate amount. Potassium iodide (0.05 mole % per mole of the finished silver halide) was added, with vigorous stirring, at the step of completion of 88% addition of the entire silver nitrate amount. Further, $K_2[IrCl_5(H_2O)]$ and $K[IrCl_4(H_2O)_2]$ were added at the step of from 92% to 98% addition of the entire silver nitrate amount. The thus-obtained emulsion grains were monodisperse cubic silver iodobromochloride grains having a side length of 0.39 μm and a variation coefficient of 10%. The resulting emulsion was subjected to a sedimentation desalting treatment and re-dispersing treatment in the same manner as described in the above.

The re-dispersed emulsion was dissolved at 40° C., and Spectral sensitizing dye H, Compound I, triethylthiourea as a sulfur sensitizer, Compound-1 as a gold sensitizer were added, and the emulsion was ripened for optimal chemical sensitization. Thereafter, 1-(3-acetamidophenyl)-5-mercaptotetrazole, 1-(5-methylureidophenyl)-5-mercaptotetrazole, Compound-2, Compound-4, and potassium bromide were added. The thus-obtained emulsion was referred to as Emulsion RH-1.

(Preparation of Red-Sensitive Layer Emulsion RL-1)

Emulsion grains were prepared in the same manner as in the preparation of Emulsion RH-1, except that the temperature and the addition rate at the step of mixing silver nitrate and sodium chloride by simultaneous addition were changed, and the amounts of respective metal complexes that were to be added during the addition of silver nitrate and sodium chloride were changed. The thus-obtained emulsion grains were monodisperse cubic silver iodobromochloride grains having a side length of 0.29 μm and a variation coefficient of 9.9%. After this emulsion was subjected to a sedimentation desalting treatment and re-dispersion, Emulsion RL-1 was prepared in the same manner as Emulsion RH-1, except that the amounts of compounds in the preparation of RH-1 were changed. The thus-obtained emulsion was referred to as Emulsion RL-1.

Samples 1702 to 1713 were prepared in the same manner as Sample 1701, except that Exemplified coupler (101) in Sample 1701 was changed to Exemplified coupler (102), (103), (104), (106), (108), (109), (111), (117), (121), (131), (133), or (139), in an equimolar amount, respectively. These samples were subjected to exposure to light and development processing in the same manner as in Example 7, followed by evaluation in the same manner as in Example 7. It was confirmed that these samples were excellent in prevention of color impurity, in fastness to light at the low-density portion, and in fastness to humidity and heat. Further, it was confirmed that these samples were excellent in density stability in rapid processing.

Example 14

Samples corresponding to the samples in Examples 7 to 13 were prepared in the same manner as in Examples 7 to 13, except for the following modifications: In preparing samples in Examples 7 to 13, an additional layer was formed, by applying a coating solution having a formulation as described below, at the position nearest to the support (i.e. the position between the support and the first layer), by the following method; and the viscosity of the respective coating solutions of the additional layer, and the rest of layers to be formed thereon, was changed as shown below. In the above, in the case of samples corresponding to Example 8, which had the reversed layer constitutions to those corresponding to Example 7, the respective fifth layers in Example 7 were the first layers. These samples corresponding to Examples 7 to 13 were exposed to light and subjected to development processing, followed by evaluation in the same manner as in Examples 7 to 13. It was confirmed that the couplers of the present invention exhibited superior effects as in Examples 7 to 13.

The coating solution of the additional layer was prepared by allowing an aqueous solution of 5 mass % alkali-treated gelatin to contain Surfactant (Cpd-13) and a viscosity-enhancing agent, as used in working examples of U.S. Pat. No. 5,393,571, in an amount of about 0.1 mass %, respectively, and by adjusting the viscosity of the solution to be 140 mPa·s. The thus-prepared coating solution and the coating solutions of the rest of the layers to be applied thereon, were simultaneously coated according to a curtain coating method described in U.S. Pat. No. 5,393,571. In the coating, the viscosity of the respective coating solutions was adjusted to 140 mPa·s (the additional layer), 350 mPa·s (the first layer in the layer constitution before the modifications), about 120 mPa·s (each of the second to seventh layers in the layer constitution before the modifications), and about 40 mPa·s (the sixth layer of ultraviolet absorbing layer, and the seventh layer of protective layer, each in the layer constitution before the modifications), and these coating solutions were coated at a rate of 350 to 450 m/minute.

Having described our invention as related to the present embodiments, it is our intention that the invention not be limited by any of the details of the description, unless otherwise specified, but rather be construed broadly within its spirit and scope as set out in the accompanying claims.

This nonprovisional application claims priority under 35 U.S.C. § 119 (a) on Patent Application No. 2002-283780 filed in Japan on Sep. 27, 2002 and on Patent Application No. 2002-284156 filed in Japan on Sep. 27, 2003, which are herein incorporated by reference.

What we claim is:

1. A yellow dye-forming coupler represented by formula (I):

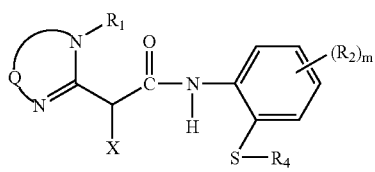

formula (I)

wherein Q represents a group of nonmetallic atoms that form a 5- to 7-membered ring in combination with the —N=C—N($R_1$)—; $R_1$ is —$(CH_2)_3O$—$R_{101}$ in which $R_{101}$ is an alkyl group having 4 to 8 carbon atoms and $R_2$ represents a substituent; $R_4$ represents an alkyl group; m represents an integer of 0 to 4; when m is 2 or more, the multiple $R_2$'s may be the same or different, and the $R_2$'s may bond with each other to form a ring; and X represents a hydrogen atom, or a group capable of being split-off upon a coupling reaction with an oxidized product of a developing agent.

2. The yellow dye-forming coupler as claimed in claim 1, wherein the yellow dye-forming coupler represented by formula (I) is a yellow dye-forming coupler represented by formula (IA):

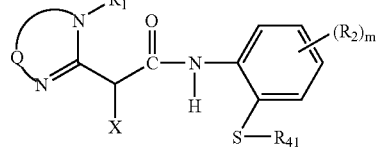

formula (IA)

wherein Q represents a group of nonmetallic atoms that form a 5- to 7-membered ring in combination with the —N=C—N($R_1$)—; $R_1$ is —$(CH_2)_3O$—$R_{101}$ in which $R_{101}$ is an alkyl group having 4 to 8 carbon atoms and $R_2$ represents a substituent; $R_{41}$ represents a secondary or tertiary alkyl group; m represents an integer of 0 to 4; when m is 2 or more, the multiple $R_2$'s may be the same or different, and the $R_2$'s may bond with each other to form a ring; and X represents a hydrogen atom, or a group capable of being split-off upon a coupling reaction with an oxidized product of a developing agent.

3. A yellow dye-forming coupler represented by formula (IB):

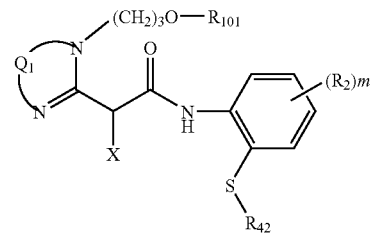

formula (IB)

wherein $Q_1$ represents a group of nonmetallic atoms that form a 5- to 7-membered ring in combination with the —N=C—N(($CH_2)_3O$—$R_{101}$)—; $R_{101}$ represents an alkyl group having 4 to 8 carbon atoms; $R_2$ represents a substituent; $R_{42}$ represents a primary alkyl group; m represents an integer of 0 to 4; when m is 2 or more, the multiple $R_2$'s may be the same or different, and the $R_2$'s may bond with each other to form a ring; and X represents a hydrogen atom, or a group capable of being split-off upon a coupling reaction with an oxidized product of a developing agent.

4. A silver halide color photographic light-sensitive material comprising at least one yellow dye-forming coupler represented by formula (I) in at least one layer provided on a support:

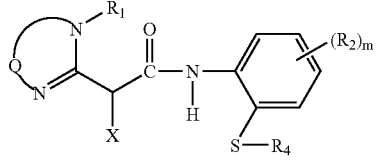

formula (I)

wherein Q represents a group of nonmetallic atoms that form a 5- to 7-membered ring in combination with the —N=C—N($R_1$)—; $R_1$ is —$(CH_2)_3O$—$R_{101}$ in which $R_{101}$ is an alkyl group having 4 to 8 carbon atoms and $R_2$ represents a substituent; $R_4$ represents an alkyl group;

m represents an integer of 0 to 4; when m is 2 or more, the multiple $R_2$'s may be the same or different, and the $R_2$'s may bond with each other to form a ring; and X represents a hydrogen atom, or a group capable of being split-off upon a coupling reaction with an oxidized product of a developing agent.

5. The silver halide color photographic light-sensitive material as claimed in claim 4, wherein the yellow dye-forming coupler represented by formula (I) is a yellow dye-forming coupler represented by formula (IA):

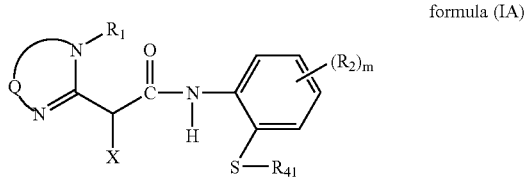

formula (IA)

wherein Q represents a group of nonmetallic atoms that form a 5- to 7-membered ring in combination with the —N═C—N($R_1$)—; $R_1$ is —$(CH_2)_3$O—$R_{101}$ in which $R_{101}$ is an alkyl group having 4 to 8 carbon atoms and $R_2$ represents a substituent; $R_{41}$ represents a secondary or tertiary alkyl group; m represents an integer of 0 to 4; when m is 2 or more, the multiple $R_2$'s may be the same or different, and the $R_2$'s may bond with each other to form a ring; and X represents a hydrogen atom, or a group capable of being split-off upon a coupling reaction with an oxidized product of a developing agent.

6. The silver halide color photographic light-sensitive material as claimed in claim 5, wherein Q in formula (IA) is a group represented by —C(—R11)═C(—R12)—$SO_2$— or —C(—R11)═C(—R12)—CO—, in which R11 and R12 are groups that bond with each other to form a 5- to 7-membered ring together with —C═C—, or they each independently represents a hydrogen atom or a substituent.

7. The silver halide color photographic light-sensitive material as claimed in claim 5, wherein the yellow dye-forming coupler represented by formula (IA) is a yellow dye-forming coupler represented by formula (IIA):

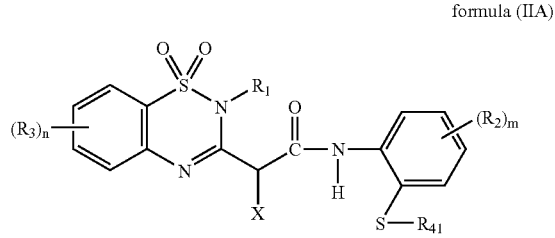

formula (IIA)

wherein $R_1$ is —$(CH_2)_3$O—$R_{101}$ in which $R_{101}$ is an alkyl group having 4 to 8 carbon atoms and $R_2$ each independently represents a substituent; $R_{41}$ represents a secondary or tertiary alkyl group; m represents an integer of 0 to 4; when m is 2 or more, the multiple $R_2$'s may be the same or different, and the $R_2$'s may bond with each other to form a ring; $R_3$ represents a substituent; n represents an integer of 0 to 4; when n is 2 or more, the multiple $R_3$'s may be the same or different, and the $R_3$'s may bond with each other to form a ring; and X represents a hydrogen atom, or a group capable of being split-off upon a coupling reaction with an oxidized product of a developing agent.

8. A silver halide color photographic light-sensitive material, comprising at least one yellow dye-forming coupler represented by formula (IB) in at least one layer provided on a support:

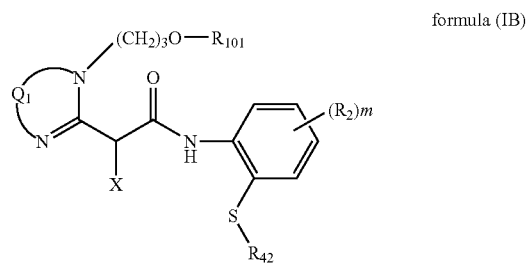

formula (IB)

wherein $Q_1$ represents a group of nonmetallic atoms that form a 5- to 7-membered ring in combination with the —N═C—N(($CH_2)_3$—O—$R_{101}$)—; $R_{101}$ represents an alkyl group having 4 to 8 carbon atoms; $R_2$ represents a substituent; $R_{42}$ represents a primary alkyl group; m represents an integer of 0 to 4; when m is 2 or more, the multiple $R_2$'s may be the same or different, and the $R_2$'s may bond with each other to form a ring; and X represents a hydrogen atom, or a group capable of being split-off upon a coupling reaction with an oxidized product of a developing agent.

9. The silver halide color photographic light-sensitive material as claimed in claim 8, wherein $Q_1$ in formula (IB) is a group represented by —C(—R11)═C(—R12)—$SO_2$— or —C(—R11)═C(—R12)—CO—, in which R11 and R12 are groups that bond with each other to form a 5- to 7-membered ring together with —C═C—, or they each independently represent a hydrogen atom or a substituent.

10. The silver halide color photographic light-sensitive material as claimed in claim 8, wherein the yellow dye-forming coupler represented by formula (IB) is a yellow dye-forming coupler represented by formula (IIB):

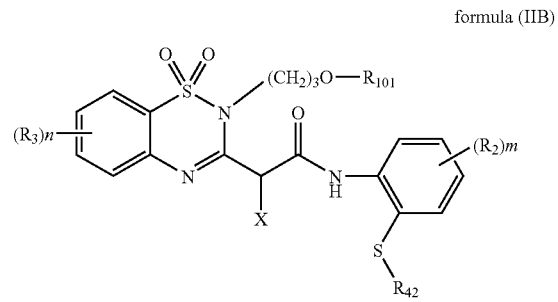

formula (IIB)

wherein $R_{101}$ represents an alkyl group having 4 to 8 carbon atoms; $R_2$ represents a substituent; $R_{42}$ represents a primary alkyl group; m represents an integer of 0 to 4; when m is 2 or more, the multiple $R_2$'s may be the same or different, and the $R_2$'s may bond with each other to form a ring; $R_3$ represents a substituent; n represents an integer of 0 to 4; when n is 2 or more, the multiple $R_3$'s may be the same or different, and the $R_3$'s may bond with each other to form a ring; and X represents a hydrogen atom, or a group capable of being split-off upon a coupling reaction with an oxidized product of a developing agent.

11. The silver halide color photographic light-sensitive material as claimed in claim 8, wherein $R_2$ in formula (IB) represents a t-butyl group.

12. The silver halide color photographic light-sensitive material as claimed in claim 4, wherein the amount of the yellow dye-forming coupler is $1\times10^{-3}$ mole to 1 mole per mole of silver halide.

13. The silver halide color photographic light-sensitive material as claimed in claim 4, wherein an emulsion of the layer containing the yellow dye-forming coupler represented by formula (I) is a silver halide emulsion having silver chloride content of 90 mol % or more.

14. The silver halide color photographic light-sensitive material as claimed in claim 13, wherein the silver halide emulsion is doped with an iridium complex.

15. The silver halide color photographic light-sensitive material as claimed in claim 4, wherein a hydrophilic colloid layer is provided between the support and a color-forming silver halide emulsion layer nearest to the support.

* * * * *